(12) United States Patent
Baumann et al.

(10) Patent No.: US 7,547,763 B2
(45) Date of Patent: Jun. 16, 2009

(54) SEQUENCES OF AN $I_h$ ION CHANNEL AND USE THEREOF

(75) Inventors: Arnd Baumann, Juelich (DE); Wolfgang Bonigk, Juelich (DE); Renate Gauss, Juelich (DE); Alexander Scholten, Dormagen (DE); Reinhard Seifert, Aachen (DE); Benjamin Kaupp, Aachen (DE)

(73) Assignee: Forschungszentrum Julich GmbH, Juelich (DE)

( * ) Notice: Subject to any disclaimer, the term of this patent is extended or adjusted under 35 U.S.C. 154(b) by 45 days.

(21) Appl. No.: 11/497,168

(22) Filed: Aug. 1, 2006

(65) Prior Publication Data

US 2006/0269959 A1  Nov. 30, 2006

Related U.S. Application Data

(60) Division of application No. 09/640,582, filed on Aug. 17, 2000, now Pat. No. 7,112,667, which is a continuation-in-part of application No. PCT/EP99/00942, filed on Feb. 12, 1999.

(30) Foreign Application Priority Data

Feb. 17, 1998 (DE) .................. 198 06 581

(51) Int. Cl.
  *C07K 1/00* (2006.01)
  *C12P 21/06* (2006.01)
(52) U.S. Cl. ..................... 530/350; 435/69.1
(58) Field of Classification Search ............ None
  See application file for complete search history.

(56) References Cited

U.S. PATENT DOCUMENTS

2003/0118988 A1  6/2003  Kandel et al.

FOREIGN PATENT DOCUMENTS

WO  99/18941 A2  4/1999

WO  WO 99/18941 A2  4/1999

OTHER PUBLICATIONS

Bucci et al., *J. Gen. Physiol.*, 120: 1-13 (2002).
Chaplan et al., *J. Neurosci.*, 23(4): 1169-1178 (2003).
Gauss et al., *Nature*, 393(11): 583-587 (1998).
Hiller et al., EMHUM Database Engry HSN72770, Acession No. N72770, XO02109146 (1996).
Jenkins et al., *PCR Methods and Applications*, 3(5): S77-82 (1994).
Ludwig et al., *Nature*, 393(11) 587-591 (1998).
Ludwig et al., *The EMBO Journal*, 18(9): 2323-2329 (1999).
Ludwig et al., *The EMBO Journal*, 22(2): 216-224 (2003).
Santoro et al., *PNAS USA*, 94: 14815-14820 (1997).
Santoro et al., *Cell*, 93: 717-729 (1998).
Seifert et al., *PNAC USA*, 96: 9391-9396 (1999).
Bucci et al., *J. Gen. Physiol.*, 120: 1-13 (2002).
Chaplan et al., *J. Neurosci.*, 23(4):1169-1178 (2003).
Gauss et al., *Nature*, 393(11): 583-587 (1998).
Hiller et al., Emhum Database Engry HSN72770, Accession No. N72770, XO0209146 (1996).
Jenkins et al., *PCR Methods and Applications*, 3(5): S77-82 (1994).
Ludwig et al., *Nature*, 393(11) 587-591 (1998).
Ludwig et al., *The EMBO Journal*, 18(9): 2323-2329 (1999).
Ludwig et al., *The EMBO Journal*, 22(2): 216-224 (2003).
Santoro et al., *PNAS USA*, 94: 14815-14820 (1997).
Santoro et al., *Cell*, 93: 717-729 (1998).
Santoro et al., *GenBank* Accession No. AF064877 (May 29, 1998).
Seifert et al., *PNAS USA*, 96: 9391-9396 (1999).

*Primary Examiner*—Olga N Chernyshev
(74) *Attorney, Agent, or Firm*—Leydig, Voit & Mayer, Ltd.

(57) ABSTRACT

The present invention relates to an isolated or purified human nucleic acid, preferably a DNA, comprising a nucleotide sequence encoding an $I_h$ ion channel. The invention further relates to a vector comprising the isolated or purified nucleic acid, a host cell comprising the vector, and a composition comprising the isolated or purified nucleic acid and a carrier therefore. The invention also provides a polypeptide or protein encoded by the nucleic acid, and a method of treating a mammal for a cardiovascular disorder.

1 Claim, 18 Drawing Sheets

FIG. 1A

```
CGGGAGAATAGTGCACCAAGGGATGCCCGTGAAATATTAATTAAACGTTTTTAAGAACA      -101
TCATCAAACCCGGGCCCCATCATGAAGGAATAACAAGGCCTTCGAAAAGTATGGGAAACT      -41
GGTCGGCAGGACATCAGCATTATTAATTCTAGGAAACTCATTATGGATAACAAGGAAACT       18
                                         M   D   N   K   E   T     6

AACGGAGAGCTAGAGCAGTCTGATGAGGCCGATCCGTCCGGTCAAAACCTTGATGATGGG       78
  N   G   E   L   E   Q   S   D   E   A   D   P   S   G   Q   N   L   D   D   G   26

GAAACCGATAGCAAACAAGAAGAGAATCTCATCAACGTTAGCCCGCCAAAAACACCGCCA      138
  E   T   D   S   K   Q   E   E   N   L   I   N   V   S   P   P   K   T   P   P   46

GGTCCTCCTCCTCCTCTAAAGAATGGAGGAAGGGGTCAGAAACCGCCCAAAATCCCAATA      198
  G   P   P   P   P   L   K   N   G   G   R   G   Q   K   P   P   K   I   P   I   66

TGTCATCAAAATGGAAAGCTCCCCAAGGAAGTTGAATGGACAGAAGACAGAGGCGAAGAC      258
  C   H   Q   N   G   K   L   P   K   E   V   E   W   T   E   D   R   G   E   D   86

AGAAAGGATAGTCTCACTCTTCAATCAAAGCTAGATCACGGGGCATACACGGATGAGAAA      318
  R   K   D   S   L   T   L   Q   S   K   L   D   H   G   A   Y   T   D   E   K  106
                ▲
CAGGATCTTCTAACATATCTTGACCGTCACGGCATCAACAGTCCAGTCAAGCTAACACCA      378
  Q   D   L   L   T   Y   L   D   R   H   G   I   N   S   P   V   K   L   T   P  126

GATGAAACTGGAGGGAGCAGTGCTTTGGATATTCTTGGGATTATTGAAGAGAGGGACACT      438
  D   E   T   G   G   S   S   A   L   D   I   L   G   I   I   E   R   D   T  146

GGTGCACTAGGCTCTGATCCCTCATCCACTATGCAGGCCATGGCTAAACCTGTAGGCTTT      498
  G   A   L   G   S   D   P   S   S   T   M   Q   A   M   A   K   P   V   G   F  166

CTGCAGAGGCAGCTATGGACTGTCCTCCAACCTTCAGACAATAGACTCTCCATGAAACTT      558
  L   Q   R   Q   L   W   T   V   L   Q   P   S   D   N   R   L   S   M   K   L  186
                                                                    •
TTCGGAAGCAAGAAAGGGTTACAAAAGGAAAAATATCGGCTGAGGAAGGCGGGGGTTCTT      618
  F   G   S   K   K   G   L   Q   K   E   K   Y   R   L   R   K   A   G   V   L  206
                                        ─────────────── S1 ───────────────
ATCATTCATCCATGTAGTCATTTCAGATTTTACTGGGATCTACTGATGCTGTGCCTGATC      678
  I   I   H   P   C   S   H   F   R   F   Y   W   D   L   L   M   L   C   L   I  226
────────────────────────────────────
ATGGCAAACGTCATCCTCCTACCCGTCGTCATTACTTTCTTCCACAACAAGGACATGAGT      738
  M   A   N   V   I   L   L   P   V   V   I   T   F   F   H   N   K   D   M   S  246
─────────────────────────────────────────────── S2 ───────────────
ACGGGTTGGCTCATCTTTAATTGCTTCTCAGATACCTTCTTCATTCTCGATCTCATCTGC      798
  T   G   W   L   I   F   N   C   F   S   D   T   F   F   I   L   D   L   I   C  266

AACTTTCGGACCGGCATCATGAATCCGAAGTCGGCCGAACAGGTGATCCTCAACCCCCGT      858
  N   F   R   T   G   I   M   N   P   K   S   A   E   Q   V   I   L   N   P   R  286
                                ─────────────── S3 ───────────────
CAAATCGCCTATCATTATCTCCGTTCATGGTTCATCATCGATCTCGTGTCTTCCATCCCC      918
  Q   I   A   Y   H   Y   L   R   S   W   F   I   I   D   L   V   S   S   I   P  306
```

FIG. 1A (Continued)

```
ATGGACTACATCTTCCTCCTCGCTGGCGGCCAGAACCGTCACTTCCTCGAGGTGTCCCGA   978
 M  D  Y  I  F  L  L  A  G  G  Q  N  R  H  F  L  E  V  S  R    326
─────────────────────────── S4 ───────────────────────────
GCCCTCAAGATACTGCGCTTTGCCAAGCTCCTCAGTCTTCTTCGACTCCTGCGTCTGTCC  1038
 A  L  K  I  L  R  F  A  K  L  L  S  L  L  R  L  L  R  L  S    346

AGGCTCATGCGGTTCGTCAGTCAATGGGAACAGGCCTTCAACGTAGCCAATGCCGTCATC  1098
 R  L  M  R  F  V  S  Q  W  E  Q  A  F  N  V  A  N  A  V  I    366
─────────────────────────── S5 ───────────────────────────
CGGATCTGTAATCTAGTGTGTATGATGCTTCTGATTGGCCATTGGAATGGCTGCCTTCAA  1158
 R  I  C  N  L  V  C  M  M  L  L  I  G  H  W  N  G  C  L  Q    386

TATCTCGTGCCCATGCTGCAAGAATACCCCGACCAATCATGGGTCGCCATTAATGGCCTT  1218
 Y  L  V  P  M  L  Q  E  Y  P  D  Q  S  W  V  A  I  N  G  L    406
────────────────────────────────────── Pore ──────
GAGCACGCTCATTGGTGGGAGCAGTATACATGGGCACTCTTCAAAGCCCTTTCGCACATG  1278
 E  H  A  H  W  W  E  Q  Y  T  W  A  L  F  K  A  L  S  H  M    426

CTCTGTATCGGGTACGGCAAGTTCCCCCCTCAAAGCATCACCGATGTCTGGCTAACGATT  1338
 L  C  I  G  Y  G  K  F  P  P  Q  S  I  T  D  V  W  L  T  I    446
─────────────────────────── S6 ───────────────────────────
GTCAGTATGGTGTCCGGTGCGACCTGCTTCGCCCTGTTCATCGGACACGCTACCAATCTC  1398
 V  S  M  V  S  G  A  T  C  F  A  L  F  I  G  H  A  T  N  L    466

ATCCAGTCCATGGACTCCTCCAGCAGGCAATACCGTGAGAAGTTGAAACAAGTTGAAGAG  1458
 I  Q  S  M  D  S  S  S  R  Q  Y  R  E  K  L  K  Q  V  E  E    486
                        •
TACATGCAGTATCGCAAGCTACCGTCCCACCTACGAAACAAGATCCTCGATTACTACGAG  1518
 Y  M  Q  Y  R  K  L  P  S  H  L  R  N  K  I  L  D  Y  Y  E    506

TACCGATACCGAGGAAAGATGTTTGATGAGAGGCATATCTTTCGAGAAGTGTCGGAGAGT  1578
 Y  R  Y  R  G  K  M  F  D  E  R  H  I  F  R  E  V  S  E  S    526
 *                                                           •
ATACGACAGGATGTCGCAAACTACAATTGTCGCGACCTGGTCGCATCCGTCCCTTTCTTC  1638
 I  R  Q  D  V  A  N  Y  N  C  R  D  L  V  A  S  V  P  F  F    546

GTCGGTGCCGACTCAAACTTCGTCACCCGTGTGGTGACGCTGCTCGAATTCGAGGTCTTC  1698
 V  G  A  D  S  N  F  V  T  R  V  V  T  L  L  E  F  E  V  F    566

CAACCCGCTGACTATGTTATACAGGAAGGTACTTTCGGTGATCGCATGTTCTTCATCCAG  1758
 Q  P  A  D  Y  V  I  Q  E  G  T  F  G  D  R  M  F  F  I  Q    586

CAGGGCATCGTCGACATCATCATGTCCGACGGCGTCATCGCCACGTCACTCAGTGACGGC  1818
 Q  G  I  V  D  I  I  M  S  D  G  V  I  A  T  S  L  S  D  G    606
──────────────────── cNMP binding site ────────────────────
TCATATTTTGGCGAAATCTGCCTGCTTACCCGTGAGCGCCGCGTGGCATCGGTGAAGTGC  1878
 S  Y  F  G  E  I  C  L  L  T  R  E  R  R  V  A  S  V  K  C    626
                                                •
GAGACCTACTGCACGCTCTTCTCGCTCTCCGTCCAGCATTTCAACCAAGTGCTCGACGAG  1938
 E  T  Y  C  T  L  F  S  L  S  V  Q  H  F  N  Q  V  L  D  E    646
```

FIG. 1A (Continued)

```
TTTCCCGCCATGAGGAAAACGATGGAAGAGATAGCCGTTCGTCGTCTGACCCGAATCGGG    1998
 F  P  A  M  R  K  T  W  E  E  I  A  V  R  R  L  T  R  I  G      666
                         A

AAGGAATCGAGCAAGCTGAAATCCCGCCTAGAGAGCCCGACGATCAGGGACACTGCCCCT    2058
 K  E  S  S  K  L  K  S  R  L  E  S  P  T  I  R  D  T  A  P      686

CTCTTTCCGATCCCACCTGATACACCGTCTTTCGTCACCGACATCGAAAAGAACCGGTTC    2118
 L  F  P  I  P  P  D  T  P  S  F  V  T  D  I  E  K  N  R  F      706

TTTGGCGACGACACGGACGATGTACACATCAGGACCCGAGTCGACGTCGAGCGTGGTTCG    2178
 F  G  D  D  T  D  D  V  H  I  R  T  R  V  D  V  E  R  G  S      726

CATGAAAACGTCATCGCCATCATGGATGGGAGTTTATCCGACCTCAGGATGGAAAACGAA    2238
 H  E  N  V  I  A  I  M  D  G  S  L  S  D  L  R  M  E  N  E      746

ATCCAAGCCCGTAAATCGTCTAGCGGAAAACGGAGGAAATTCCAGCAACAAACAACCGAA    2298
 I  Q  A  R  K  S  S  S  G  K  R  R  K  F  Q  Q  Q  T  T  E      766
                   A

CTATGACGACTTGAAACAAACAATGATGGACGCTTACAATTTCCAGTGATTCAATACTTA    2358
 L  -    [SEQ. ID NO. 18]                                          767

CGCAATGCAGACATTAGCTTTTGTACCTGATTGTTTAGAATGTATTGAATTTGTAGATCA    2418
GTCCGGCAAATAAGAAAGCATAATTTGGAATTTCTTTCATTGAGGAAGTACTGAAAACAA    2478
TGTGATAGCAGCCGGTAGAAATTTCTTGTCCATTATCGAGGCTATATTTTTCGCGCTTTC    2538
TTACGAAGTAAATGAAAGGATCAATTAAATTATTGTTCTTTGTCTCGTGCGCTTTGTATC    2598
TGATGCCGAAAGGAATGAAACGTGATTAGAACAGTAATCGATTGAACTACAGAAGTCTT    2658
TTCAAAATGTTGAATGTATGAAGGAGGAGGGGAAGGTTTGATATATGCAAAGAAATGGA    2718
GAAATATTTTTGTAAATTTATCTAGAATGGTACTATTGATGCTGGAAAGGTGTTGAAGTT    2778
GTCCAATATTGTGTCAAATCACCAACTATTTGACATTTGTCTTTTTC [SEQ. ID NO. 4]  2825
```

Fig. 1B

S4 motif

| | | | | | | |
|---|---|---|---|---|---|---|
| SPIH | 326- | R A L K I L R F A K L L S L L R L L R L S R L M R | -350 | SEQ ID NO: 4 |
| Shaker | 344- | M S L A I L R V I R L V R V F R I F K L S R H S K | -368 | SEQ ID NO: 23 |
| DmEAG | 341- | S L F S A L K V V R L L R L L R L L R L V R K L D R Y L | -365 | SEQ ID NO: 24 |
| HERG | 519- | E L I G L L K T A R L L R L V R V A R K L D R Y S | -543 | SEQ ID NO: 25 |
| KAT1 | 168- | S M L R L W R L R R V S S L F A R L E K D I R F N | -192 | SEQ ID NO: 26 |
| brCNGC α | 263- | W N Y P E I R L N L R L I S R M F E F F Q R T E | -287 | SEQ ID NO: 27 |

FIG. 1C pore

| | | | |
|---|---|---|---|
| 416- | ... | | SEQ ID NO: 4 |
| 418- | ... | | SEQ ID NO: 28 |
| 441- | ... | | SEQ ID NO: 29 |
| 612- | ... | | SEQ ID NO: 30 |
| 248- | ... | | SEQ ID NO: 31 |
| 348- | ... | | SEQ ID NO: 32 |

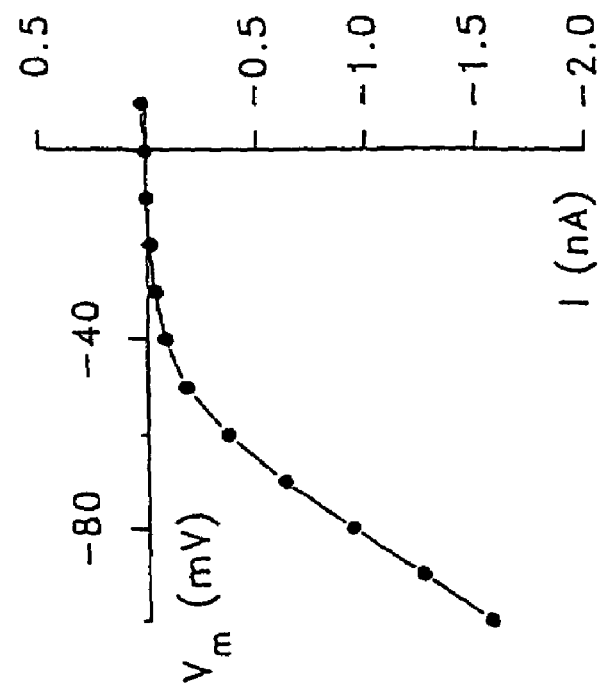
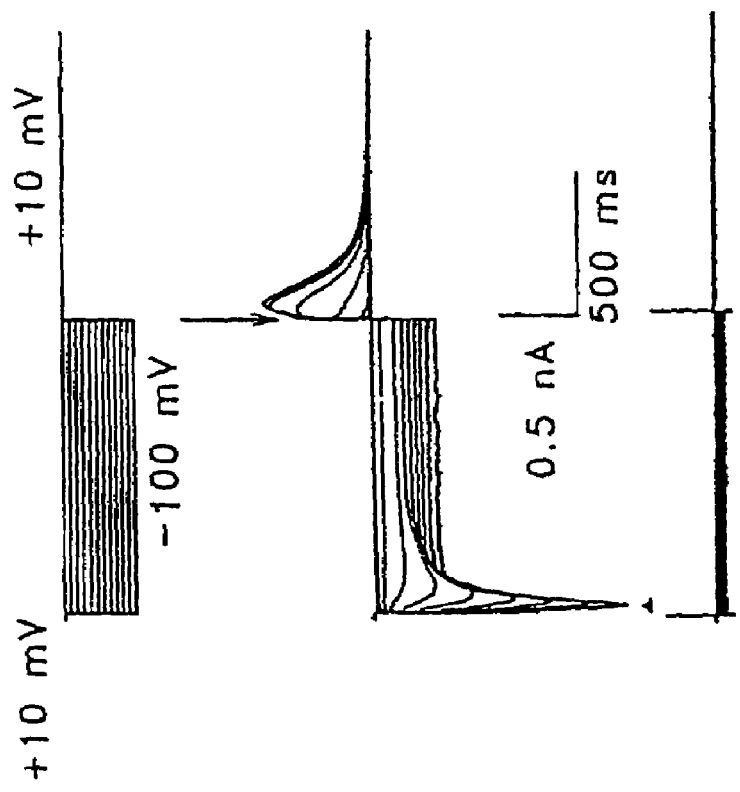
FIG. 2A
FIG. 2B

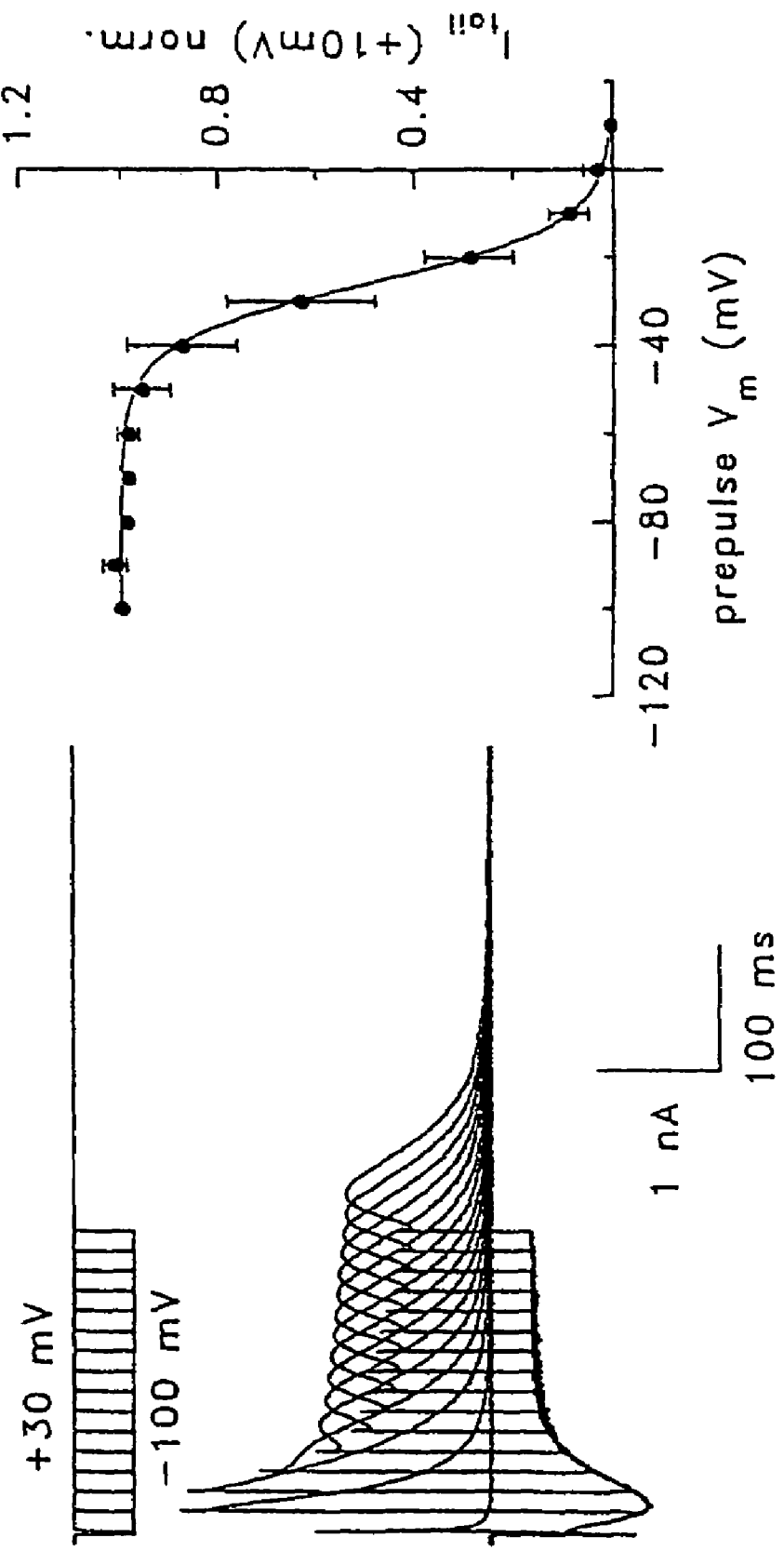

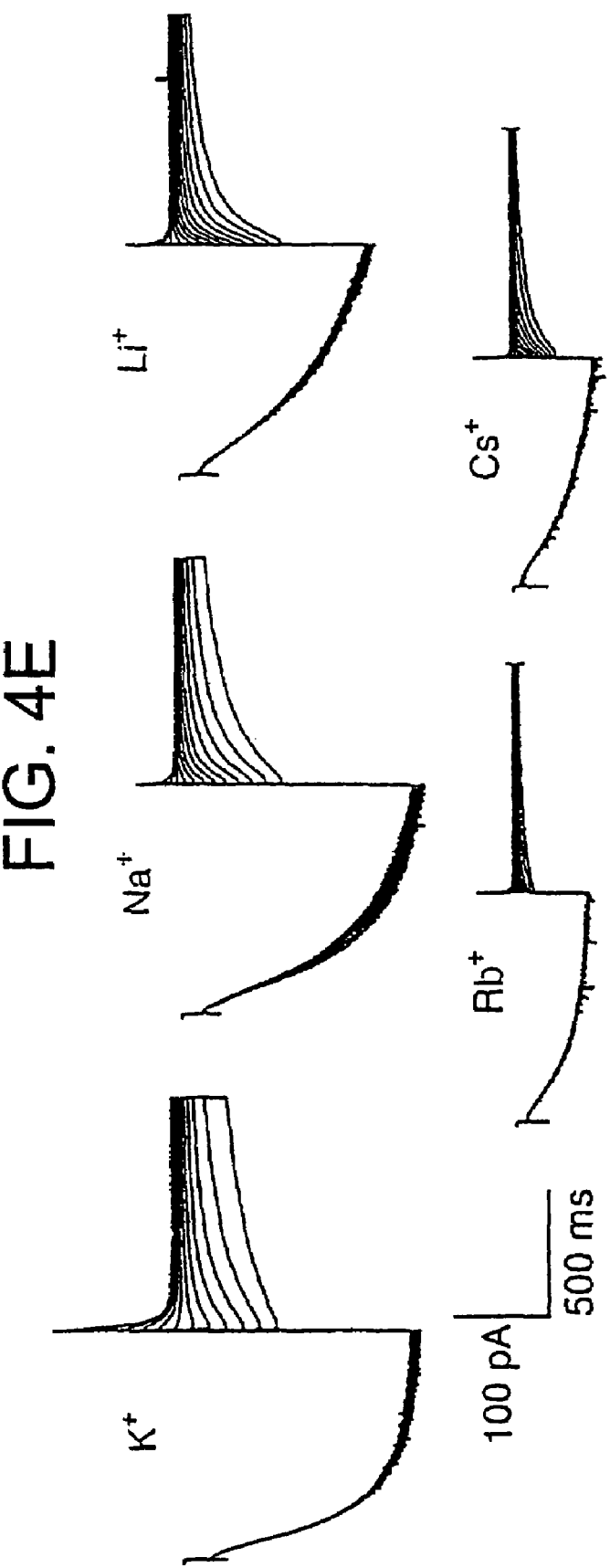

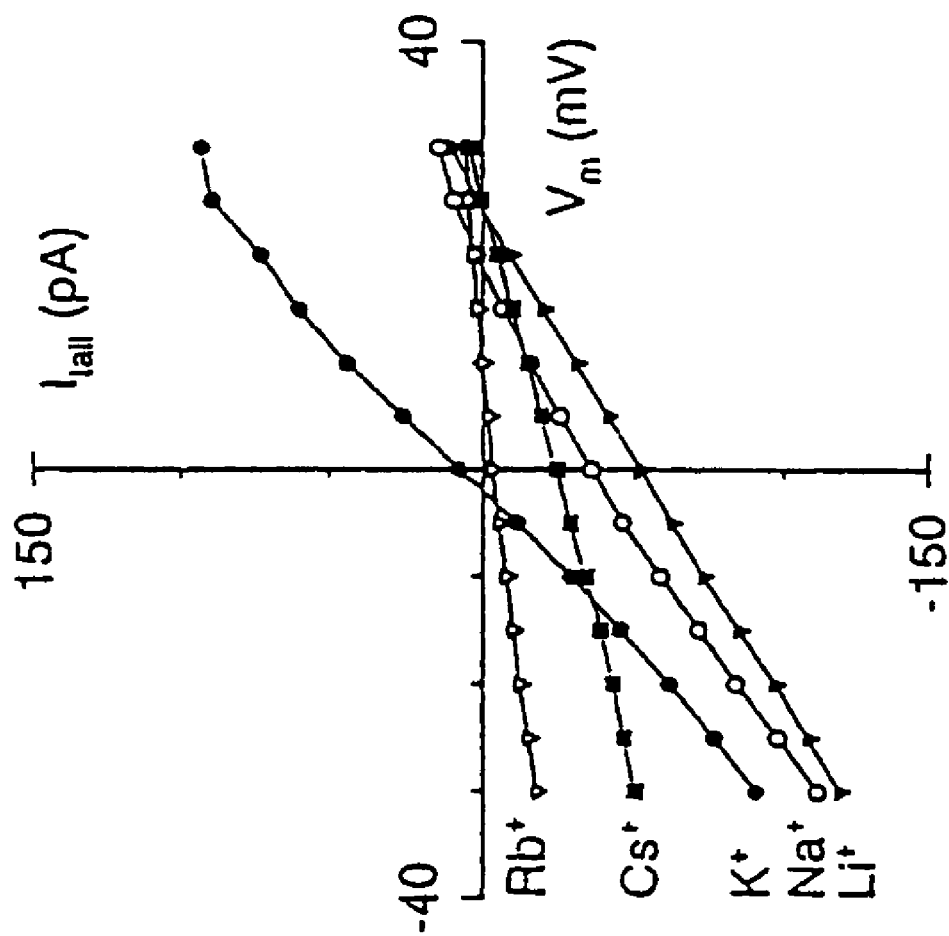

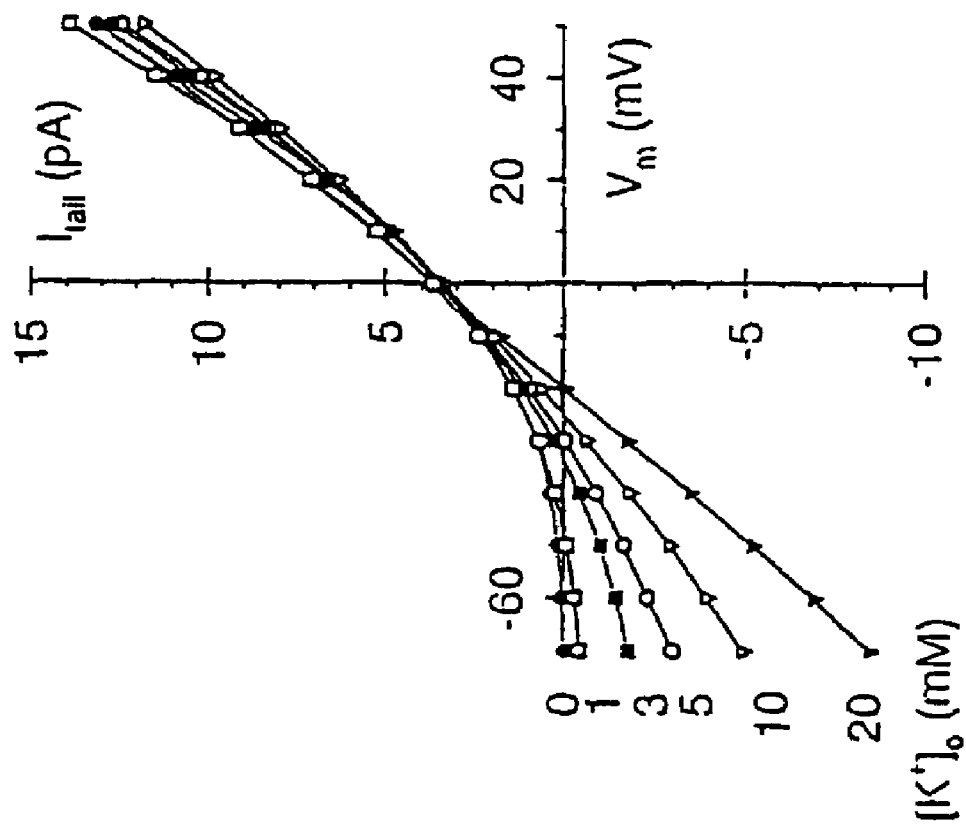

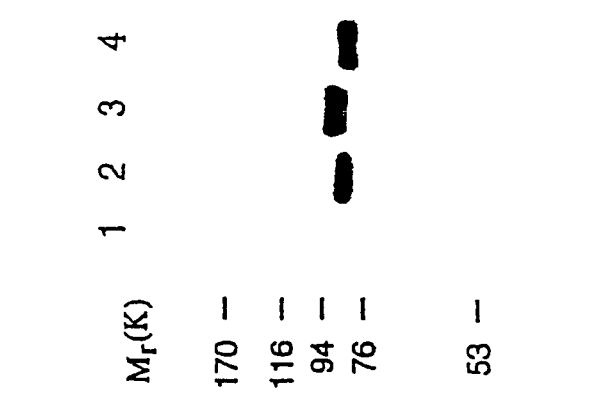
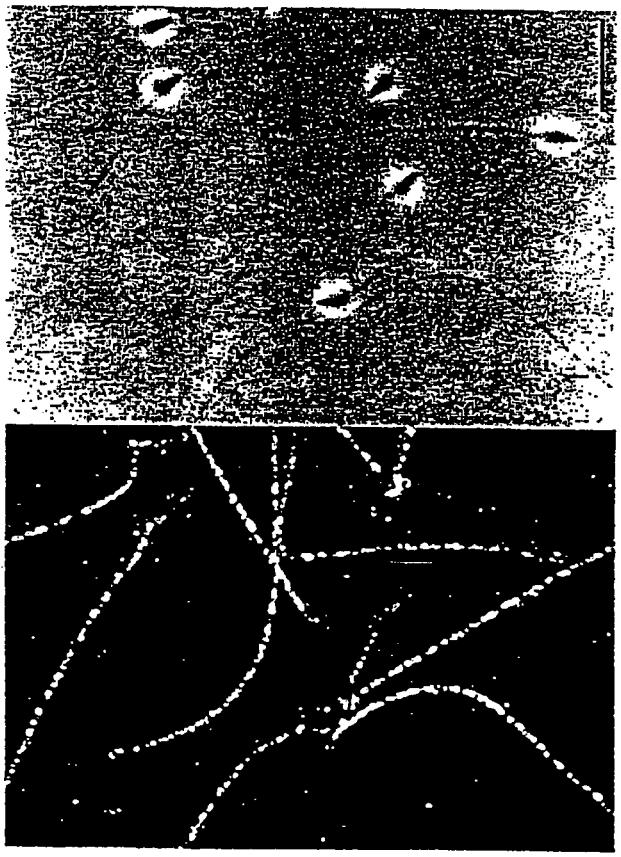
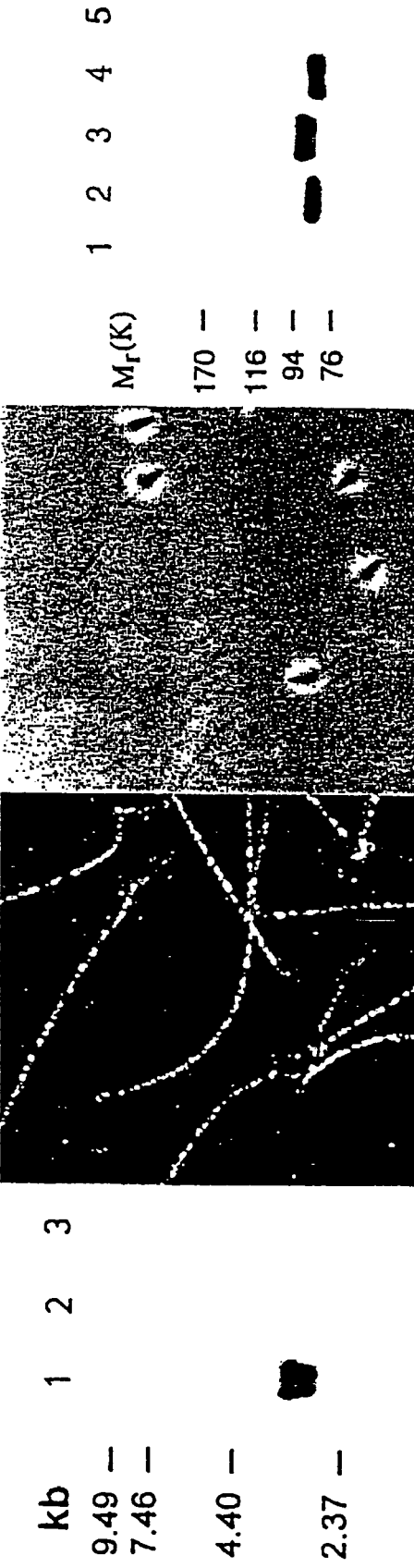
FIG. 5C
FIG. 5B
FIG. 5A

SEQUENCE LISTING

```
<160> NUMBER OF SEQ ID NOS: 20

<210> SEQ ID NO 1
<211> LENGTH: 1342
<212> TYPE: DNA
<213> ORGANISM: Homo sapiens
<220> FEATURE:
<221> NAME/KEY: MISC_FEATURE
<222> LOCATION: (1308)..(1308)
<223> OTHER INFORMATION: "n" may be any nucleotide.
<220> FEATURE:
<221> NAME/KEY: MISC_FEATURE
<222> LOCATION: (1334)..(1334)
<223> OTHER INFORMATION: "n" may be any nucleotide.

<400> SEQUENCE: 1
cgttgcgctt caccaagatc ctcagcctcc tgcggctgct gcgcctctca cgcctgatcc      60
gctacatcca tcagtgggag gagatcttcc acatgaccta tgacctggcc agcgcggtga     120
tgaggatctg caatctcatc agcatgatgc tgctgctctg ccactgggac ggctgcctgc     180
agttcctggt gccatgctg caggacttcc cgcgcaactg ctgggtgtcc atcaatggca     240
tggtgaacca ctcgtggagt gaactgtact ccttcgcact cttcaaggcc atgagccaca     300
tgctgtgcat cgggtacggc cggcaggcgc ccgagagcat gacggacatc tggctgacca     360
tgctcagcat gattgtgggt gccacctgct acgccatgtt catcggccac gccactgccc     420
tcatccagtc gctggactcc tcgcggcgcc agtaccagga gaagtacaag caggtggagc     480
agtacatgtc cttccacaag ctgccagctg acttccgcca gaagatccac gactactatg     540
agcaccgtta ccagggcaag atgtttgacg aggacagcat cctgggcgag ctcaacgggc     600
ccctgcggga ggagatcgtc aacttcaact gccgaagct ggtggcctcc atgccgctgt     660
tcgccaacgc cgacccaac ttcgtcacgg ccatgctgac caagctcaag ttcgaggtct     720
tccagccggg tgactacatc atccgcgaag gcaccatcgg gaagaagatg tacttcatcc     780
agcacggcgt ggtcagcgtg ctcactaagg gcaacaagga gatgaagctg tccgatggct     840
cctacttcgg ggagatctgc ctgctcaccc ggggccgccg cacggcgagc gtgcgggctg     900
```

```
acacctactg ccgcctctat tcgctgagcg tggacaactt caacgaggtg ctggaggagt      960
accccatgat gcggcgcgcc ttcgagacgg tggccatcga ccgcctggac cgcatcggca     1020
agaagaattc catcctcctg cacaaggtgc agcatgacct caactcgggc gtattcaaca     1080
accaggagaa cgccatcatc caggagatcg tcaagtacga ccgcgagatg gtgcagcagg     1140
ccgagctggg ctcagcgcgt gggcctcttc ccgccgccgc cgccgccgcc gcagtcacct     1200
cggccatcgc cacgctgcag caggcggcgg ccatgagctt ctgcccgcag tggcgcggcc     1260
gctcgtgggg ccgctggcgc tcggctcgcc gcgcctcgtg cgchgcyndy hcccggggsc     1320
cgcacctgch gccncctcac cc                                              1342

<210> SEQ ID NO 2
<211> LENGTH: 3112
<212> TYPE: DNA
<213> ORGANISM: Rattus rattus

<400> SEQUENCE: 2
cctggttcgt ggtggacttc atctcctcga tcccggtgga ttatatcttt cttattgtag       60
agaaaggaat ggattcggaa gtttacaaga ccgccagagc acttcggatc gtgaggttta      120
caaaaattct cagtctcttg cgtttattac gcctttcaag gttaattaga tacatacacc      180
agtgggaaga gatattccac atgacatatg atctcgccag tgcagtggtg agaatcttca      240
acctcattgg catgatgctg ctcctgtgtc actgggatgg ctgtcttcag tttctggtcc      300
ccctgctgca ggacttccca ccggattgct gggtttctct aaatgaaatg gttaatgatt      360
catgggggaa acagtattcc tacgcactct tcaaagctat gagtcacatg ctgtgcattg      420
gttatggcgc ccaggccccc gtcagcatgt ctgacctctg gattaccatg ctgagcatga      480
ttgttggggc cacctgctat gccatgtttg tcggccatgc cacagctttg atccagtctc      540
tggattcttc aaggaggcag tatcaagaga agtacaagca agtagagcaa tacatgtcat      600
tccacaagtt accagctgac atgcgccaga agatacatga ttactatgag caccgatacc      660
aaggcaagat cttcgatgag gaaaatattc tcagtgaact taatgatcct ctgagagagg      720
aaatagtcaa cttcaactgc cggaaactgg tggccaccat gcctctcttt gctaacgcgg      780
atcccaattt cgtgacggcc atgctgagca agctgagatt tgaggtgttc cagcccggag      840
actatatcat tcgagaagga gctgtgggga agaaaatgta tttcatccag catggtgtgg      900
ctggtgtcat caccaagtcc agtaaagaaa tgaagttgac agacggctct tactttggag      960
aaatatgcct gctgaccaag ggccggcgca ctgccagtgt tcgagctgat acatactgtc     1020
gcctttactc cctttcggtg acaatttca acgaggtctt ggaggaatat ccaatgatga     1080
gaagagcctt tgagacagtt gctattgacc gactagatcg gataggcaag aaaaactcta     1140
ttctcctgca gaagttccag aaggatctga acactggtgt tttcaacaac caggagaatg     1200
agatcctgaa gcagattgtg aagcatgaca gagagatggt acaagcgatc cctccaatca     1260
actatcctca aatgacagcc ctgaattgca catcttcaac caccaccccca acgtcgcgca     1320 tgaggaccca atctccacca gtctacacag cgaccagcct ctctcacagc aacctgcact     1380
cacccagccc cagcacacag acgcctcaac cctcagccat cctttcaccc tgctcctaca     1440
ccacagcagt ctgcagtcct cctatacaga gcccctggc cacgcgaact ttccattatg     1500
cctctcccac tgcatcccaa ttgtcactca tgcagcagcc tcagccgcag ctacagcaat     1560
cccaggtaca gcagactcag ccgcagccgc agccgcagcc gcagcagccg caacagcaac     1620
```

-continued

```
aacagcagca acagcagcag cagcagcagc agcaacaaca acagcagcag caacagccac    1680
agacacctgg tagttccaca ccgaaaaatg aagtgcacaa gagcactcaa gctcttcata    1740
acaccaacct gaccagagaa gtcaggcccc tctctgcctc gcagccttcg ctgccccatg    1800
aggtctccac tatgatctcc agaccgcatc ccactgtggg cgagtccctg gcctccatcc    1860
ctcaacccgt ggcaacagtc cacagcactg gccttcaggc agggagcagg agcaccgtgc    1920
cacagcgtgt caccttgttc agacagatgt cctcgggagc tatttccccc aaccgaggag    1980
tgcctccagc accccacca ccagcagctg tgcagagaga gtctccctca gtcttaaata    2040
aagacccaga tgcagaaaaa ccacgttttg cttcgaattt atgattcttg ctgattgtca    2100
aagcagaaaa gaaatactct aataaacaga atattctcag atattatttt attctatctc    2160
atgatagagc cctatagcct actctaaaaa gatattttag aagctctggc gtacatgcaa    2220
atgtaaaaac atatatacat atattattaa atatatatat atatctaaat gcccaagaga    2280
agttcaaaag acttgtataa ctttcagtgt tatgtcttcc tttctttaaa accattaaag    2340
gatttaacac attgttgtaa gatcattgat ttctaacctt ttacttaatt cctttgttat    2400
atgtgtttct ccctttatg aagagttctt gaagtcattg gaaacaaaac tctgatttag    2460
aaataaaagg caactccaat tagtttcagc atagcaccaa tcaaagcttt ctttcattaa    2520
ctgtgcctct gcatctaggt tgttaattat gtgggattca ataaagaaat cccagtttat    2580
agctctaaat tgtattttgg tgctttaaat tttgagttat gtgaaggaac acactacacg    2640
ctcagccacc ataggagact aacattgcca ctgttaaggc ttcctctaac ctcaaacatg    2700
ttcgtcaatt ttgtgaggaa aggtgaggag atatttgtct tcatgtgtta ttggacttt     2760 accaagattc agtcaatgtt agctgtaaat aacttttcca acctgaataa aagtaactat    2820
tctgtgttgt ataaaggtaa aagtcactgt ttaagaattt agttttattg cttcacttca    2880
aaagttagag ttttaaaatt tcacaaaaca taataattgt gacaactgtt caaatgtaat    2940
gcaattgctt gagacctaca atatcattta aacctgcaat attttatgca aaaattgtat    3000
gcttgaacct acaaattgct tgtattacac caaaaatcat tacttttatt ccttcttgac    3060
ataatcaagc atctgaacct agtcctggca tgcttttggg ggcaaaaaaa aa            3112
```

<210> SEQ ID NO 3
<211> LENGTH: 2606
<212> TYPE: DNA
<213> ORGANISM: Bos taurus

<400> SEQUENCE: 3

```
cgggagcccg gagcgcagcc actgagggca gcggcggcgg cgggagcgag gcgcgcagcg     60
agaagcggcg gcgaggaatc ggccgggggc ttcgaggacg ccgaggggcc ccggcggcag    120
tacggcttca tgcagcggca gttcacctcc atgctgcagc ccggggtcaa caattctcc    180 ctccgcatgt tcgggagcca gaaggcggtg gagaaggagc aggaaagggt taaaactgca    240
ggcttctgga ttatccaccc ttacagtgat ttcaggtttt attgggattt aataatgctt    300
ataatgatgg ttgaaaatct ggtcatcata ccagttggaa tcacattctt tacagaacag    360
acaacaacac catggattat tttcaatgtg gcttcagata cagttttcct tttggacttg    420
atcatgaatt tcaggactgg gactgtcaat gaagacagtt ctgaaatcat cctggacccct   480 aaagtgatca agatgaatta tttaaaaagc tggtttgtgg ttgacttcat ctcatcaatc    540
ccagtggatt atatctttct cattgtagaa aaaggaatgg attcggaagt ttacaagaca    600
gccagggcac ttcgcattgt gaggtttaca aaaattctca gtctcttgcg tttattacga    660
```

| | |
|---|---:|
| ctttcaaggt taattagata catacatcag tgggaagaga ttttccacat gacatatgat | 720 |
| cttgccagtg ctgtggtgag aattttaac ctcattggca tgatgctgct cctgtgccac | 780 |
| tgggatggct gtcttcagtt cctggtacca ctgctgcagg acttcccacc agattgctgg | 840 |
| gtgtctctaa atgagatggt taatgattct tggggaaagc agtattccta cgcgctcttc | 900 |
| aaagcgatga gtcatatgct gtgcattggc tacgagccc aagccccgt gagcatgtct | 960 |
| gacctgtgga tcaccatgct gagcatgatc gtcggggcca cctgctacgc catgtttgtt | 1020 |
| ggccacgcca cggctctaat tcagtctttg gattcctcaa gcggcaata tcaagagaag | 1080 |
| tataagcaag tggaacaata catgtcattc cataagttac cagctgatat gcgtcagaag | 1140 |
| atacatgatt attatgaaca cagataccaa ggcaaaatct ttgatgagga aaatattctc | 1200 |
| aatgaactca atgatcctct gagagaggag atagtcaact tcaactgccg aaaactagtg | 1260 |
| gctacaatgc ctcttttgc taatgcggat cctaatttcg tgaccgccat gctgagcaag | 1320 |
| ttgagatttg aggtgtttca acctggagat tatatcatac gagaaggagc tgtggctaaa | 1380 |
| aaaatgtatt tcattcaaca tggtgttgct ggtgtcatca caaatccag taagaaatg | 1440 |
| aagctgacag atggctcata ctttggagag atttgcttgc tgaccaaggg acggcgcact | 1500 |
| gccagtgttc gagctgatac atattgtcgt ctttactcac tttctgtgga caatttcaat | 1560 |
| gaggtcctgg aggaatatcc aatgatgaga agagcctttg agacggttgc cattgaccga | 1620 |
| ttagatagga tagggaagaa aaattcaatt ctccctgcaaa agttccagaa ggatctgaac | 1680 |
| acgggtgttt tcaacaatca ggagaacgag atcctgaagc agattgtgaa acacgacagg | 1740 |
| gaaatggtgc aggcaatccc tccctcaat taccctcaaa tgacagccct gaattccacc | 1800 |
| tcttcaacta ctaccccgac ctctcgcctg aggacacagt caccgccagt gtacacagcc | 1860 |
| accagtctgt ctcatagcaa cctgcactcc cccagcccca gcacccagac ccccagccg | 1920 |
| tcagccatcc tctcgccctg ctcctacacc accgctgtct gcagccctcc tgtacagagc | 1980 |
| ccgctagcca ctcgaacttt ccactatgcc tccccacgg cttcccagtt gtccctcatt | 2040 |
| cagcagcagc aggttcagca gccaccgcag ccccagcagc caccccaacc tccacagacc | 2100 |
| cccggcagct ccacaccgaa aaacgaagtg cacaagagca cgcaggcgct tcacaacacc | 2160 |
| agcctgaccc gagaagtcag gccctctcg gcctcgcagc cctcgctgcc ccacgaggtc | 2220 |
| tccaccctga tctccagacc gcatcccact gtgggcgagt ccctggcctc catccctcaa | 2280 |
| cccgtgacca cggtccacgg ctcgggcctg caggcagggg cagggcac cgtcccccag | 2340 |
| cgagtcaccc tgttccgaca gatgtcatcg ggagccatcc ccccaatcg aggagtcccc | 2400 |
| ccggcccccc ctccaccagc agccgctcat ccgagggagg cgccctcagt cttaactaca | 2460 |
| gactcagagg cagaaaagcc acgatttgct tcaaatttat gatcctgctg attgtaaagc | 2520 |
| agaaagaaat actctaacgt aactgaggac gcttctcaga tttgattta ttctatctcc | 2580 |
| tgatagatcc tctagcctac tatgaa | 2606 |

<210> SEQ ID NO 4
<211> LENGTH: 2986
<212> TYPE: DNA
<213> ORGANISM: Strongylocentrotus purpuratus

<400> SEQUENCE: 4

| | |
|---|---:|
| cgggagaata gtgcaccaag ggatgcccgt gaaatattaa ttaaacgttt ttaagaacat | 60 |
| catcaaaccc gggcccatc atgaaggaat aacaaggcct tcgaaaagta tgggaaactg | 120 |

| | |
|---|---|
| gtcggcagga catcagcatt attaattcta ggaaactcat tatggataac aaggaaacta | 180 |
| acggagagct agagcagtct gatgaggccg atccgtccgg tcaaaacctt gatgatgggg | 240 |
| aaaccgatag caaacaagaa gagaatctca tcaacgttag cccgccaaaa acaccgccag | 300 |
| gtcctcctcc tcctctaaag aatggaggaa ggggtcagaa accgcccaaa atcccaatat | 360 |
| gtcatcaaaa tggaaagctc cccaaggaag ttgaatggac agaagacaga ggcgaagaca | 420 |
| gaaaggatag tctcactctt caatcaaagc tagatcacgg ggcatacacg gatgagaaac | 480 |
| aggatcttct aacatatctt gaccgtcacg gcatcaacag tccagtcaag ctaacaccag | 540 |
| atgaaactgg agggagcagt gctttggata ttcttgggat tattgaagag agggacactg | 600 |
| gtgcactagg ctctgatccc tcatccacta tgcaggccat ggctaaacct gtaggctttc | 660 |
| tgcagaggca gctatggact gtcctccaac cttcagacaa tagactctcc atgaaacttt | 720 |
| tcggaagcaa gaaagggtta caaaaggaaa aatatcggct gaggaaggcg ggggttctta | 780 |
| tcattcatcc atgtagtcat ttcagatttt actgggatct actgatgctg tgcctgatca | 840 |
| tggcaaacgt catcctccta cccgtcgtca ttactttctt ccacaacaag gacatgagta | 900 |
| cgggttggct catctttaat tgcttctcag atacctttct cattctcgat ctcatctgca | 960 |
| actttcggac cggcatcatg aatccgaagt cggccgaaca ggtgatcctc aaccccgtc | 1020 |
| aaatcgccta tcattatctc cgttcatggt tcatcatcga tctcgtgtct tccatcccca | 1080 |
| tggactacat cttcctcctc gctggcggcc agaaccgtca cttcctcgag gtgtcccgag | 1140 |
| ccctcaagat actgcgcttt gccaagctcc tcagtcttct tcgactcctg cgtctgtcca | 1200 |
| ggctcatgcg gttcgtcagt caatgggaac aggccttcaa cgtagccaat gccgtcatcc | 1260 |
| ggatctgtaa tctagtgtgt atgatgcttc tgattggcca ttggaatggc tgccttcaat | 1320 |
| atctcgtgcc catgctgcaa gaataccccg accaatcatg ggtcgccatt aatggccttg | 1380 |
| agcacgctca ttggtgggag cagtatacat gggcactctt caaagccctt tcgcacatgc | 1440 |
| tctgtatcgg gtacggcaag ttccccccctc aaagcatcac cgatgtctgg ctaacgattg | 1500 |
| tcagtatggt gtccggtgcg acctgcttcg ccctgttcat cggacacgct accaatctca | 1560 |
| tccagtccat ggactcctcc agcaggcaat accgtgagaa gttgaaacaa gttgaagagt | 1620 |
| acatgcagta tcgcaagcta ccgtcccacc tacgaaacaa gatcctcgat tactacgagt | 1680 |
| accgataccg aggaaagatg tttgatgaga ggcatatctt tcgagaagtg tcggagagta | 1740 |
| tacgacagga tgtcgcaaac tacaattgtc gcgacctggt cgcatccgtc cctttcttcg | 1800 |
| tcggtgccga ctcaaacttc gtcacccgtg tggtgacgct gctcgaattc gaggtcttcc | 1860 |
| aacccgctga ctatgttata caggaaggta cttccggtga tcgcatgttc ttcatccagc | 1920 |
| agggcatcgt cgacatcatc atgtccgacg gcgtcatcgc cacgtcactc agtgacggct | 1980 |
| catatttttgg cgaaatctgc ctgcttaccc gtgagcgccg cgtggcatcg gtgaagtgcg | 2040 |
| agacctactg cacgctcttc tcgctctccg tccagcattt caaccaagtg ctcgacgagt | 2100 |
| ttcccgccat gaggaaaacg atggaagaga tagccgttcg tcgtctgacc cgaatcggga | 2160 |
| aggaatcgag caagctgaaa tcccgcctag agagcccgac gatcagggac actgcccctc | 2220 |
| tctttccgat cccacctgat acaccgtctt tcgtcaccga catcgaaaag aaccggttct | 2280 |
| ttggcgacga cacggacgat gtacacatca ggacccgagt cgacgtcgag cgtgttcgc | 2340 |
| atgaaaacgt catcgccatc atggatggga gtttatccga cctcaggatg gaaaacgaaa | 2400 |
| tccaagcccg taaatcgtct agcggaaaac ggaggaaatt ccagcaacaa acaaccgaac | 2460 |
| tatgacgact tgaaacaaac aatgatggac gcttacaatt tccagtgatt caatacttac | 2520 |

-continued

```
gcaatgcaga cattagcttt tgtacctgat tgtttagaat gtattgaatt tgtagatcag    2580
tccggcaaat aagaaagcat aatttggaat ttctttcatt gaggaagtac tgaaaacaat    2640
gtgatagcag ccgtagaaa tttcttgtcc attatcgagg ctatatttt cgcgctttct    2700 tacgaagtaa atgaaggat caattaaatt attgttcttt gtctcgtgcg ctttgtatct    2760
gatgccgaaa aggaatgaaa cgtgattaga acagtaatcg attgaactac agaagtcttt    2820
tcaaaatgtt gaatgtatga aggaggaggg ggaaggtttg atatatgcaa agaaatggag    2880 aaatatttt gtaaatttat ctagaatggt actattgatg ctggaaaggt gttgaagttg    2940
tccaatattg tgtcaaatca ccaactattt gacatttgtc tttttc                  2986
```

<210> SEQ ID NO 5
<211> LENGTH: 3185
<212> TYPE: DNA
<213> ORGANISM: Drosophila melanogaster

<400> SEQUENCE: 5

```
cggaatttcc tcgctgaagg gcaaggggca gagtcagagt cagggcaga gcggcagacg     60 ctgcccggcc atcgcgggtc ggtgaggagc gagagtggaa gcgggagcag ccacaccatt    120
ccggcgacgg gcaagagtcc gccggtgccg cactcgctgg cggccaagat cagcagctcg    180
gcaagcggca gcaagaactg caatttgctc agcgccagca gcaactcatg ccacaagctg    240
aacgcccacg cccaaggatc ggagcaggat cgggatcttg gatcgggatc aggatcagga    300
ccacccggac acagtcacta cgcggccgcc tcgcccaaaa gctcggtcag cagcaacggt    360
catctgaaca gtactgcct cacggacctc acgcgccgca acgcgagttc aatcgccagc    420
tgagcgcgcc cacggactac acgcaccact cctccagcaa cggatcgcag caggagggct    480
cctcggaggc caacgagggc cacgaaccgg tcggcgagtc caccatcacc gtagccagtg    540
ccggcgtatc gtatccgcat ccgtactcct atccgtatca ttacggcacc accgctcctc    600
ggccacagcg ccggccaatc tcaaggcgtc gctgcagctg cacagctttg ggagccacca    660
tccgtgtcct tatccggcaa ggcccacgtc acgtcgtgc accaacagct caaccggcg     720 ccacattcgc cggcacaagg gcaagctcgg cgatcgactg ctgagcgggg atagtgagga    780
atcggtgcgc tgctcctatt gctcggtgct gaatgcgaac gacaacgacc tgcgcatttc    840
gttcgagaac acctgcaccg attcgctggt aaccgctttc gatgatgaag ccctgctaat    900
atgcgaccaa ggaaccgaaa tggtacactt tgatgacgtg tcgttgtacg gcactccgaa    960
agaggagccc atgcccaaca taccgatcgt gtcggaaaaa gtctctgcga atttcctaaa   1020
aagtcaattg caatcatggt tccagccgac ggacaaccga ctggccatga aactgtttgg   1080
cagccgaaag gcgctggtca aggagcgcat acgtcagaaa acttccgggc actgggtcat   1140
acacccgtgc agttcattca ggttttactg ggaccttgc atgcttttat tattagtagc   1200
aaatcttatt atcctgccag tcgcaatatc attcttcaac gatgatctga gcacacgatg   1260
gattgccttc aactgcctaa gtgatactat ttttttaata gatattgtag tcaattttag   1320
aacaggaatt atgcaacaag acaacgctga acaagtaata ttggatccaa agcttatagc   1380
taaacactat ttaagaactt ggttttttct cgatttgatt tcgtcgatac cgctagatta   1440 tatatttta attttcaatc aaattatgaa attgcaggat ttctctgatt cttttcaaat   1500
attgcatgcc ggacgcgccc tgccgatcct gcgcctggcc aagctgttat ccctggtgcg   1560
actgctccgc ctttcccgcc tcgtccgcta cgtttcccaa tggaggaggg tctatttcct   1620
```

-continued

```
caatatggcc tcggtcttca tgaggatctt caatttaatt tgcatgatgc tcctgatcgg    1680
ccattggagc ggttgcttgc agttcttagt gccaatgttg cagggttttc catccaactc    1740
ctgggtctcc atcaacgagt tgcaggaatc gtactggctg gagcagtatt cgtgggcatt    1800
gttcaaggcc atgtcgcaca tgctctgcat aggctacggc agattccgc cacaatcact     1860 gacagacatg tggctgacga tgctatcgat gatatccggg gccacctgtt acgcattgtt    1920
cctcggtcac gcgaccaatc tcatccagag cttggactcc agccggcgcc agtatcgcga    1980
gaaggtcaaa caggtggagg agtacatggc ctaccgcaag ctgccacgcg acatgcggca    2040
gcgcatcacg gaatatttcg agcatcggta ccagggtaaa ttcttcgatg aagagttgat    2100
acttggcgag ttgagcgaaa aactgcgcga ggatgtcatc aactacaact gcagatccct    2160
cgtggcgtca gtgcctttt ttgctaatgc cgattcgaat ttcgtttccg acgtagttac     2220
caaactgaaa tacgaagttt tccaaccagg tgatattatc ataaaggagg gtacgatcgg    2280
tactaagatg tacttcatac aggagggcgt ggtggacatt gtcatggcca acggcgaggt    2340
tgccacctca ctttcggatg ggtcttattt cggtgagatc tgtctgctga ccaatgcgcg    2400
tcgtgtggcc agcgtgcgag ccgaaaccta ttgcagtcta ttctcgttga gcgtggatca    2460
tttcaattgc gttctggatc agtatccgct gatgcgcaag accatggaga ctgtggccgc    2520
cgagcggtta acaagatcg gcaagaatcc aaacataatg catcagaagg acgagcagct     2580
gagcaatccg gagtcgaaca cgattacggc tgtggttaat gcactggctg ccgaggcgga    2640
tgactgcaaa gatgatgaca tggatctcag ggagaattta ctgcatgggt cagagtcgag    2700
cattgctgag ccggtgcaga cgatacgtga gggtctcccg aggccacgga gcggggagtt    2760
ccgggccttg ttcgagggta acactccatg acactgagga gcagtgacaa gcggtgccct    2820
cgggcaccgg gcaaccatct gaagcagcag ttcgctggac actcactcac caagtcccac    2880
atccatactc cacacaggac taccactcac acacacacac acactgcgta tataataatt    2940
tagtaaaagg aaccccaaga cgcgataaga gtacactaaa aaaagaatca atttatggta    3000
gacactctat atatgcaatt gcgatttagt agaaaacgta ttaaaaacta aaacccaaa     3060 aaaagaagat aaaaacaatt acacaaaaaa tgtcctcaat aattattcat aatttcagct    3120
ccgctaactg tgatgacttt aatataagaa tcgaaaaaaa aattaacaaa caaacaaaaa    3180
aaaag                                                                3185
```

<210> SEQ ID NO 6
<211> LENGTH: 2922
<212> TYPE: DNA
<213> ORGANISM: Bos taurus
<220> FEATURE:
<221> NAME/KEY: MISC_FEATURE
<222> LOCATION: (1925)..(1925)
<223> OTHER INFORMATION: "n" may be any nucleotide.
<220> FEATURE:
<221> NAME/KEY: MISC_FEATURE
<222> LOCATION: (1969)..(1969)
<223> OTHER INFORMATION: "n" may be any nucleotide.
<220> FEATURE:
<221> NAME/KEY: MISC_FEATURE
<222> LOCATION: (1987)..(1988)
<223> OTHER INFORMATION: "n" may be any nucleotide.
<220> FEATURE:
<221> NAME/KEY: MISC_FEATURE
<222> LOCATION: (2432)..(2432)
<223> OTHER INFORMATION: "n" may be any nucleotide.
<220> FEATURE:
<221> NAME/KEY: MISC_FEATURE
<222> LOCATION: (2435)..(2435)
<223> OTHER INFORMATION: "n" may be any nucleotide.

```
<220> FEATURE:
<221> NAME/KEY: MISC_FEATURE
<222> LOCATION: (2491)..(2491)
<223> OTHER INFORMATION: "n" may be any nucleotide.
<220> FEATURE:
<221> NAME/KEY: MISC_FEATURE
<222> LOCATION: (2518)..(2518)
<223> OTHER INFORMATION: "n" may be any nucleotide.
<220> FEATURE:
<221> NAME/KEY: MISC_FEATURE
<222> LOCATION: (2546)..(2546)
<223> OTHER INFORMATION: "n" may be any nucleotide.
<220> FEATURE:
<221> NAME/KEY: MISC_FEATURE
<222> LOCATION: (2561)..(2561)
<223> OTHER INFORMATION: "n" may be any nucleotide.
<220> FEATURE:
<221> NAME/KEY: MISC_FEATURE
<222> LOCATION: (2572)..(2572)
<223> OTHER INFORMATION: "n" may be any nucleotide.
<220> FEATURE:
<221> NAME/KEY: MISC_FEATURE
<222> LOCATION: (2756)..(2756)
<223> OTHER INFORMATION: "n" may be any nucleotide.
<220> FEATURE:
<221> NAME/KEY: MISC_FEATURE
<222> LOCATION: (2784)..(2784)
<223> OTHER INFORMATION: "n" may be any nucleotide.

<400> SEQUENCE: 6
```

| | | | | | |
|---|---|---|---|---|---|
| cgggagcccg | gagcgcagcc | actgagggca | gcggcggcgg | cgggagcgag | gcgcgcagcg | 60 |
| agaagcggcg | gcgaggaatc | ggccggggc | ttcgaggacg | ccgaggggcc | ccggcggcag | 120 |
| tacggcttca | tgcagcggca | gttcacctcc | atgctgcagc | ccggggtcaa | caaattctcc | 180 |
| ctccgcatgt | tcgggagcca | gaaggcggtg | gagaaggagc | aggaaagggt | taaaactgca | 240 |
| ggcttctgga | ttatccaccc | ttacagtgat | ttcaggtttt | attgggattt | aataatgctt | 300 |
| ataatgatgg | ttgaaaatct | ggtcatcata | ccagttggaa | tcacattctt | tacagaacag | 360 |
| acaacaacac | catggattat | tttcaatgtg | gcttcagata | cagttttcct | tttgacttg | 420 |
| atcatgaatt | tcaggactgg | gactgtcaat | gaagacagtt | ctgaaatcat | cctggaccct | 480 |
| aaagtgatca | agatgaatta | tttaaaaagc | tggtttgtgg | ttgacttcat | ctcatcaatc | 540 |
| ccagtggatt | atatctttct | cattgtagaa | aaggaatgg | attcggaagt | ttacaagaca | 600 |
| gccagggcac | ttcgcattgt | gaggtttaca | aaaattctca | gtctcttgcg | tttattacga | 660 |
| cttttcaaggt | taattagata | catacatcag | tgggaagaga | ttttccacat | gacatatgat | 720 |
| cttgccagtg | ctgtggtgag | aattttaac | ctcattggca | tgatgctgct | cctgtgccac | 780 |
| tgggatggct | gtcttcagtt | cctggtacca | ctgctgcagg | acttcccacc | agattgctgg | 840 |
| gtgtctctaa | atgagatggt | taatgattct | tggggaaagc | agtattccta | cgcgctcttc | 900 |
| aaagcgatga | gtcatatgct | gtgcattggc | tacggagccc | aagcccccgt | gagcatgtct | 960 |
| gacctgtgga | tcaccatgct | gagcatgatc | gtcgggccca | cctgctacgc | catgtttgtt | 1020 |
| ggccacgcca | cggctctaat | tcagtctttg | gattcctcaa | ggcggcaata | tcaagagaag | 1080 |
| tataagcaag | tggaacaata | catgtcattc | cataagttac | cagctgatat | gcgtcagaag | 1140 |
| atacatgatt | attatgaaca | cagataccaa | ggcaaaatct | ttgatgagga | aaatattctc | 1200 |
| aatgaactca | atgatcctct | gagagaggag | atagtcaact | tcaactgccg | aaaactagtg | 1260 |
| gctacaatgc | ctcttttttgc | taatgcggat | cctaatttcg | tgaccgccat | gctgagcaag | 1320 |
| ttgagatttg | aggtgtttca | acctggagat | tatatcatac | gagaaggagg | ctgtggtaaa | 1380 |
| aaaatgtatt | tcattcaaca | tggtgttgct | ggtgtcatca | caaaatccag | taaagaaatg | 1440 |

-continued

```
aagctgacag atggctcata ctttggagag atttgcttgc tgaccaaggg acggcgcact      1500
gccagtgttc gagctgatac atattgtcgt ctttactcac tttctgtgga caatttcaat      1560
gaggtcctgg aggaatatcc aatgatgaga agagcctttg agacggttgc cattgaccga      1620
ttagatagga taggtactgt ttattttctt ctttacttac aattcacttt taatctagtg      1680
gttgagtata tatttgcagt cataagtccc aaatgctagt ttacagattg cttattaact      1740
agcatagaaa cagcaattag ctgtagccat atttctagaa gatctgaggc actaacttct      1800
cgtctaagta ttctaggttt gtttattcat ctctgttttt actagcttca cagtctgatt      1860
tcctcagtga taccaaaagg taaaccaat gattacaaat tctagatggc attaaaatag       1920
wwctnaaaaa tacaatagta tgagtctaca ttacaaacta tattttatna caagtttttt      1980
ttttaannTT aagggtcaac attacattta ttcttatatt aagaattgaa agaattgtg       2040 cattttactt gtcacagtag aaacgttaat gtttgtaata crrrctcaag cagaaaaagc      2100
cttaatagaa ctgcccacat agatgcttta ttttgcaaac atcaacttat tttaaaatct      2160
ttcctgctct caaattaaaa tattgatata taaggcctta ctagttatac tagtttaaac      2220
gtctgaataa ttgccatgta aaaattagat cagattggct tgctgttaac ttcccaagat      2280
atgctggaac attctgatgt cagaaggtgg tatgcattca ttttccacac ccaaattctc      2340
ctccccgacc agacccttct ctgctcccctt tcccagctta actctactag ccttcatagt     2400
tcaatttaaa catcatttcc ctgtagaaac cnatngacct tccactcctc cttaatrrta      2460
tgagcaccct ggatatgttc tnccataccc ctgggatgtt cctccatcac agtacagntt      2520
ttattattta aattgctcta gagatnctaa gctttatgaa tnaagagatc angtctaatt      2580
cactattaca ttcacagtac cwwgtacaca atgaatattg ttgaagagag ttagggaggg      2640
atgaaggaat caatgaactc aaaggagatg gggttgggat cactgaaaag taaacaaaga     2700
ggtacttcaa ctgcttcatt cttattaaag gtaaggactt ttgattgatg ttacantttat    2760 gttagctttt cttctgcact ttancatctt tcttttcctc tatattagta ggacagaaga     2820
ctgcataagg atctagggtt tggttaggac aagtaaaggt agtatttggg cattaccatt     2880
atggacacaa caaggcttcc aggtggataa caataataac gg                        2922
```

<210> SEQ ID NO 7
<211> LENGTH: 1820
<212> TYPE: DNA
<213> ORGANISM: Bos taurus

<400> SEQUENCE: 7

```
cggcggacga ggcgggcagc gaggaggcgg gcccggcggg ggagtcgcgc ggcagccagg       60
ccagcttcat gcagcgccag ttcggcgcgc tcctgcagcc gggcgtcaac aagttctcgt      120
tgcggatgtt cggcagtcag aaggccgtgg agcgcgacga ggagcgcgtt aagtcagcgg      180
gggcctggat catccaccct tacagcgact tcaggttcta ctgggacttc accatgctgc      240
tcttcatggt gggaaaacctc atcatcatcc ccgtgggcat caccttcttc aaggacgaga      300
ccacggcccc atggattgtg ttcaatgttg tctcggacac attcttcctc atggacctgg      360
tgctgaactt ccgcacgggc attgtgatcg aggacaacac ggagatcatc ctggaccccg      420
agaagatcaa gaagaagtac ctgcgcacgt ggttcgtggt ggacttcgta tcctccatcc      480
ccgtggtaag ctacatcttc ctcatcgtgg agaaaggcat cgactctgag gtctacaaga      540
cggcccgcgc cctgccgatc gagccgttca ccaagatcct cagcctgctg cgcctgctcc      600
gcttgtcgcg cctcatccgc tacatccatc agtgggagga gatcttccac atgacctacg      660
```

-continued

| | |
|---|---|
| acctggcgag cgccgtcatg cgcatctgca acctcatcag catgatgctg ctcctctgcc | 720 |
| actgggatgg ctgcctgcag ttcctggtgc ccatgcttca ggacttccca cgcaactgct | 780 |
| gggtctccat caacggcatg gtgaaccact catggagcga gctctactcc ttcgcgctgt | 840 |
| tcaaggccat gagccacatg ctgtgcatcg gtacgggcg gcaggcgcca gaaagcatga | 900 |
| cggacatctg gctgaccatg ctgagcatga tcgtgggtgc cacctgctac gccatgttca | 960 |
| ttggccacgc caccgccctc atccagtcgc tggactcctc aaggcgccag taccaggaga | 1020 |
| agtacaagca agtggagcag tacatgtcct tccacaagct gccagccgac ttccgccaga | 1080 |
| agatccacga ctactacgag caccgctacc agggcaagat gttcgacgag gacagcatcc | 1140 |
| tcggcgagct caaggcgggc ctgcgggagg agatcgtcaa cttcaactgc cggaagctgg | 1200 |
| tggcctccat gccactgttc gccaatgctg accccaactt cgtcacgggc catctgacca | 1260 |
| agctcaagtt tgaggtcttc cagccaggcg actacatcat ccgtgagggc accattggca | 1320 |
| agaagatgta cttcatccaa cacggcgtgg tcagtgtgct taccttgggc aacaaggaga | 1380 |
| tgaagttgtc tgatggctcc tactttgggg agatctgcct gctgacgcgg ggccggcgca | 1440 |
| cggcgagcgt ccgggccgac acctactgcc gcctctactc gctgagtgtg gacaacttca | 1500 |
| atgaggtgct ggaggagtac cccatgatga ggcgggcctt tgagacagtc gccattgacc | 1560 |
| gcctggatcg cattggcaag aagaactcga tcctgctaca caaggtgcag cacgacctca | 1620 |
| actctggcgt gtttaacaac caggagaacg ccatcatcca ggagattgtc aagtatgacc | 1680 |
| gcgagatggt gcagcaggct gagctgggcc agcgtgtcgg cctcttcccg ccaccaccgc | 1740 |
| cacctccaca gggcacctca gccattgcca cgctgcagca gccgtggcca tgagcttctg | 1800 |
| tccacaagtc gcacgccccc | 1820 |

<210> SEQ ID NO 8
<211> LENGTH: 101
<212> TYPE: DNA
<213> ORGANISM: Rattus rattus
<220> FEATURE:
<221> NAME/KEY: MISC_FEATURE
<222> LOCATION: (101)..(101)
<223> OTHER INFORMATION: "n" may be any nucleotide.
<400> SEQUENCE: 8

| | |
|---|---|
| ctacatcatc cgagagggga ccatcgggaa gaagatgtac ttcatccagc acggggtgg t | 60 |
| gagcgtgcta accaggggca acaaggagga taagctgtca n | 101 |

<210> SEQ ID NO 9
<211> LENGTH: 558
<212> TYPE: DNA
<213> ORGANISM: Rattus rattus

<400> SEQUENCE: 9

| | |
|---|---|
| tctggtggtg cgtgagggct ccgtgggcag gaagatgtac ttcatccagc atggcgtgct | 60 |
| cagtgtgttg gcacggggcg ctcgggacac tcgcctcact gacggatcct actttgggga | 120 |
| gatctgcctg ctgactcgag gtcggagaac agccagtgta agggctgaca cctactgtcg | 180 |
| cctctactca ctcagcgtgg accacttcaa tgcagtgctt gaggagctcc cgatgatgcg | 240 |
| cagggctttt gagactgtgg ccatggaccg gcttcggcgc atcggtgagg cctgtctgcc | 300 |
| ctgtctgctc tgggccctgc ctgagcctca tctcattttc atagcaagga acctaccct | 360 |
| agtgtttctt ctccacaccc caacctaccc agtaccagca ggctattagc tctgtttctc | 420 |
| gctagtctta cccctagaaa gaaatagcca tggagctgtc tccccaaacc ctcattccct | 480 |
| gtgtcctctc gggtaccagt acttaacctc accgttttg ataccacctt ccagtttctg | 540 |

| ttgccaagca ttctctcc | 558 |

<210> SEQ ID NO 10
<211> LENGTH: 2886
<212> TYPE: DNA
<213> ORGANISM: Homo sapiens
<220> FEATURE:
<221> NAME/KEY: MISC_FEATURE
<222> LOCATION: (1119)..(1120)
<223> OTHER INFORMATION: "n" may be any nucleotide.
<220> FEATURE:
<221> NAME/KEY: MISC_FEATURE
<222> LOCATION: (1126)..(1126)
<223> OTHER INFORMATION: "n" may be any nucleotide.
<220> FEATURE:
<221> NAME/KEY: MISC_FEATURE
<222> LOCATION: (1412)..(1412)
<223> OTHER INFORMATION: "n" may be any nucleotide.
<220> FEATURE:
<221> NAME/KEY: MISC_FEATURE
<222> LOCATION: (1464)..(1464)
<223> OTHER INFORMATION: "n" may be any nucleotide.
<220> FEATURE:
<221> NAME/KEY: MISC_FEATURE
<222> LOCATION: (1684)..(1684)
<223> OTHER INFORMATION: "n" may be any nucleotide.
<220> FEATURE:
<221> NAME/KEY: MISC_FEATURE
<222> LOCATION: (2357)..(2357)
<223> OTHER INFORMATION: "n" may be any nucleotide.
<220> FEATURE:
<221> NAME/KEY: MISC_FEATURE
<222> LOCATION: (2760)..(2761)
<223> OTHER INFORMATION: "n" may be any nucleotide.

<400> SEQUENCE: 10

| gaattcgcgg ccgcgtcgac ggccagcttc atgcagcgcc agttcggcgc gctcctgcag | 60 |
| ccgggcgtca acaagttctc gctgcggatg ttcggcagcc agaaggccgt ggagcgcgag | 120 |
| caggagcgcg tcaagtcggc gggggcctgg atcatccacc cgtacagcga cttcaggttc | 180 |
| tactgggact tcaccatgct gctgttcatg gtgggaaacc tcatcatcat cccagtgggc | 240 |
| atcaccttct tcaaggatga gaccactgcc ccgtggatcg tgttcaacgt ggtctcggac | 300 |
| accttcttcc tcatggacct ggtgttgaac ttccgcaccg gcattgtgat cgaggacaac | 360 |
| acggagatca tcctggaccc cgagaagatc aagaagaagt atctgcgcac gtggttcgtg | 420 |
| gtggacttcg tgtcctccat ccccgtggac tacatcttcc ttattgtgga aagggcatt | 480 |
| gactccgagg tctacaagac ggcacgcgcc ctgcgcatcg tgcgcttcac caagatcctc | 540 |
| agcctcctgc ggctgctgcg cctctcacgc tgatccgct acatccatca gtgggaggag | 600 |
| atcttccaca tgacctatga cctggccagc gcggtgatga ggatctgcaa tctcatcagc | 660 |
| atgatgctgc tgctctgcca ctgggacggc tgcctgcagt cctggtgcc tatgctgcag | 720 |
| gacttcccgc gcaactgctg ggtgtccatc aatggcatgg tgaaccactc gtggagtgaa | 780 |
| ctgtactcct tcgcactctt caaggccatg agccacatgc tgtgcatcgg gtacggccgg | 840 |
| caggcgcccg agagcatgac ggacatctgg ctgaccatgc tcagcatgat tgtgggtgcc | 900 |
| acctcgtacg ccatgttcat cggccacgcc actgccctca tccagtcgct ggactcctcg | 960 |
| cggcgccagt accaggagaa gtacaagcag gtggaacagt acatgtcctt ccacaagctg | 1020 |
| ccagctgact ccgcagaa gatccacgac tactatgagc accgttacca gggcaagatg | 1080 |
| tttgacgagg acagcatcct gggcgagctc aacgggccnn tgcggnagga gatcgtcaac | 1140 |
| ttcaactgcc ggaagctggt ggcctccatg ccgctgttcg ccaacgccga ccccaacttc | 1200 |
| gtcacggcca tgctgaccaa gctcaagttc gaggtcttcc agccgggtga ctacatcatc | 1260 |

| | |
|---|---|
| cgcgaaggca ccatcgggaa gaagatgtac ttcatccagc acggcgtggt cagcgtgctc | 1320 |
| actaagggca acaaggagat gaagctgtcc gatggctcct acttcgggga gatctgcctg | 1380 |
| ctcacccggg gccgccgcac ggcagcgtgc gngctgacac ctactgccgc ctctattcgc | 1440 |
| tgagcgtgga caacttcaac gagntgctgg aggagtaccc catgatgcgg cgcgccttcg | 1500 |
| agacggtggc catcgaccgc ctggaccgca tcggtgagcg ggccggggc gtggccgggg | 1560 |
| cgggtgccct ggcggggag gggcgtggcc aaggcatcag gagagtggct tggacagtgg | 1620 |
| caggggaag ggcgtggctg tggcatcagg ggcacggttg gggcagagac gtggccaagg | 1680 |
| catncaggag tgtggccatg gcagcagggg cgtggctggg gcaggggcag cggctggccg | 1740 |
| ctcctaggac ccctttgggt ctagaggctg attttctgac ctattgtcct acttcagcca | 1800 |
| gaggcagcct gtttcccaag ggagggaatg cacaggtgt ttgcggttgt gccgaatgct | 1860 |
| cggtgagcac ctgctgtgtg ctgggggtgc aggggacaga cccggggcc cactcagact | 1920 |
| cccagggagg cttatggact ggtgatgaaa tcacacacga ctgggctgtg tgccagcagg | 1980 |
| gcaggtgggg ccggtgggct tccctgagtt gggaatgcag agtggagacc agggtaaggg | 2040 |
| atgccatgtg gaaacgggga ggaagatgtg ttcgtggagt ggacacagca catcccaagg | 2100 |
| ccctgaggtg gaaagaggc ctagagtcca gagagccagg gaggcctgga ggaggttggg | 2160 |
| gaagaagggg aggccagaca cacagggccc agtgggcggc agggagagtt tagactaaat | 2220 |
| caggagcatc agggagccat ggagggttct aggtgggcgg aggacctggt cagattgtat | 2280 |
| ccgccaaggc gggccgtgtc caggaggag acggtgacct ggcctctcag gggggcagtc | 2340 |
| tctggggcag ggagggncag agccctgatg actggatgta ggcgccagag agatggcggc | 2400 |
| tcatgctgct gttcgtggga atgggaatga agaccatggc tgaaacgcag acaggtgcg | 2460 |
| acggagtggt gtcagggagc tccctggtgt acagtaggaa gctctccaca acttgctcta | 2520 |
| tacagtgagt atgcaacccg ttcctgagta tcaggtgctt aggttataac ttctgtatac | 2580 |
| agcaggtgct cagcacaggc tgtgtacagg caggtgtttt cggtatgcct gtggcacact | 2640 |
| ggaggcagtc attacataat cagcgtatac aggtggtaca catgcatact tggtgcacag | 2700 |
| tgatacctgc tccatgtaca cagcaggcat taaatacctg tttactgcca ggcgcggtgn | 2760 |
| ntcacgcctg tagtcccagc actttcggag gccaaggtgg gtggatcacg aggtcaggag | 2820 |
| attgagacca tcctggctaa catggtgaaa ccccgtctct actaaaaaaa aaaaaaaaa | 2880 |
| aaaaaa | 2886 |

<210> SEQ ID NO 11
<211> LENGTH: 2029
<212> TYPE: DNA
<213> ORGANISM: Homo sapiens
<220> FEATURE:
<221> NAME/KEY: MISC_FEATURE
<222> LOCATION: (4)..(4)
<223> OTHER INFORMATION: "n" may be any nucleotide.
<220> FEATURE:
<221> NAME/KEY: MISC_FEATURE
<222> LOCATION: (536)..(536)
<223> OTHER INFORMATION: "n" may be any nucleotide.
<220> FEATURE:
<221> NAME/KEY: MISC_FEATURE
<222> LOCATION: (564)..(564)
<223> OTHER INFORMATION: "n" may be any nucleotide.
<220> FEATURE:
<221> NAME/KEY: MISC_FEATURE
<222> LOCATION: (621)..(621)
<223> OTHER INFORMATION: "n" may be any nucleotide.
<220> FEATURE:

```
<221> NAME/KEY: MISC_FEATURE
<222> LOCATION: (650)..(650)
<223> OTHER INFORMATION: "n" may be any nucleotide.
<220> FEATURE:
<221> NAME/KEY: MISC_FEATURE
<222> LOCATION: (653)..(653)
<223> OTHER INFORMATION: "n" may be any nucleotide.
<220> FEATURE:
<221> NAME/KEY: MISC_FEATURE
<222> LOCATION: (661)..(661)
<223> OTHER INFORMATION: "n" may be any nucleotide.
<220> FEATURE:
<221> NAME/KEY: MISC_FEATURE
<222> LOCATION: (664)..(664)
<223> OTHER INFORMATION: "n" may be any nucleotide.
<220> FEATURE:
<221> NAME/KEY: MISC_FEATURE
<222> LOCATION: (667)..(668)
<223> OTHER INFORMATION: "n" may be any nucleotide.
<220> FEATURE:
<221> NAME/KEY: MISC_FEATURE
<222> LOCATION: (675)..(675)
<223> OTHER INFORMATION: "n" may be any nucleotide.
<220> FEATURE:
<221> NAME/KEY: MISC_FEATURE
<222> LOCATION: (682)..(682)
<223> OTHER INFORMATION: "n" may be any nucleotide.
<220> FEATURE:
<221> NAME/KEY: MISC_FEATURE
<222> LOCATION: (689)..(690)
<223> OTHER INFORMATION: "n" may be any nucleotide.
<220> FEATURE:
<221> NAME/KEY: MISC_FEATURE
<222> LOCATION: (698)..(698)
<223> OTHER INFORMATION: "n" may be any nucleotide.
<220> FEATURE:
<221> NAME/KEY: MISC_FEATURE
<222> LOCATION: (714)..(714)
<223> OTHER INFORMATION: "n" may be any nucleotide.
<220> FEATURE:
<221> NAME/KEY: MISC_FEATURE
<222> LOCATION: (719)..(719)
<223> OTHER INFORMATION: "n" may be any nucleotide.
<220> FEATURE:
<221> NAME/KEY: MISC_FEATURE
<222> LOCATION: (733)..(733)
<223> OTHER INFORMATION: "n" may be any nucleotide.
<220> FEATURE:
<221> NAME/KEY: MISC_FEATURE
<222> LOCATION: (742)..(742)
<223> OTHER INFORMATION: "n" may be any nucleotide.
<220> FEATURE:
<221> NAME/KEY: MISC_FEATURE
<222> LOCATION: (746)..(746)
<223> OTHER INFORMATION: "n" may be any nucleotide.
<220> FEATURE:
<221> NAME/KEY: MISC_FEATURE
<222> LOCATION: (1290)..(1290)
<223> OTHER INFORMATION: "n" may be any nucleotide.
<220> FEATURE:
<221> NAME/KEY: MISC_FEATURE
<222> LOCATION: (1293)..(1293)
<223> OTHER INFORMATION: "n" may be any nucleotide.
<220> FEATURE:
<221> NAME/KEY: MISC_FEATURE
<222> LOCATION: (1306)..(1306)
<223> OTHER INFORMATION: "n" may be any nucleotide.
<220> FEATURE:
<221> NAME/KEY: MISC_FEATURE
<222> LOCATION: (1326)..(1326)
<223> OTHER INFORMATION: "n" may be any nucleotide.
<220> FEATURE:
<221> NAME/KEY: MISC_FEATURE
<222> LOCATION: (1340)..(1340)
<223> OTHER INFORMATION: "n" may be any nucleotide.
<220> FEATURE:
<221> NAME/KEY: MISC_FEATURE
<222> LOCATION: (1349)..(1349)
<223> OTHER INFORMATION: "n" may be any nucleotide.
```

```
<220> FEATURE:
<221> NAME/KEY: MISC_FEATURE
<222> LOCATION: (1358)..(1358)
<223> OTHER INFORMATION: "n" may be any nucleotide.
<220> FEATURE:
<221> NAME/KEY: MISC_FEATURE
<222> LOCATION: (1387)..(1387)
<223> OTHER INFORMATION: "n" may be any nucleotide.
<220> FEATURE:
<221> NAME/KEY: MISC_FEATURE
<222> LOCATION: (1389)..(1389)
<223> OTHER INFORMATION: "n" may be any nucleotide.
<220> FEATURE:
<221> NAME/KEY: MISC_FEATURE
<222> LOCATION: (1405)..(1405)
<223> OTHER INFORMATION: "n" may be any nucleotide.
<220> FEATURE:
<221> NAME/KEY: MISC_FEATURE
<222> LOCATION: (1408)..(1410)
<223> OTHER INFORMATION: "n" may be any nucleotide.
<220> FEATURE:
<221> NAME/KEY: MISC_FEATURE
<222> LOCATION: (1451)..(1451)
<223> OTHER INFORMATION: "n" may be any nucleotide.
<220> FEATURE:
<221> NAME/KEY: MISC_FEATURE
<222> LOCATION: (1467)..(1467)
<223> OTHER INFORMATION: "n" may be any nucleotide.
<220> FEATURE:
<221> NAME/KEY: MISC_FEATURE
<222> LOCATION: (1983)..(1983)
<223> OTHER INFORMATION: "n" may be any nucleotide.
<220> FEATURE:
<221> NAME/KEY: MISC_FEATURE
<222> LOCATION: (2009)..(2009)
<223> OTHER INFORMATION: "n" may be any nucleotide.

<400> SEQUENCE: 11
gcgngccgcg tcgacgtggc ctccatgcca ctgtttgcca atgcggaccc caacttcgtg      60
acgtccatgc tgaccaagct gcgttttgag gtcttccagc ctggggacta catcatccgg     120
gaaggcacca ttggcaagaa gatgtacttc atccagcatg gcgtggtcag cgtgctcacc     180
aagggcaaca aggagaccaa gctggccgac ggctcctact ttggagagat ctgcctgctg     240 acccgggggcc ggcgcacagc cagcgtgagg gccgacacct actgccgcct ctactcgctg     300
agcgtggaca acttcaatga ggtgctggag gagtacccca tgatgcgaag ggccttcgag     360
accgtggcgc tggaccgcct ggaccgcatt ggcaagaaga actccatcct cctccacaaa     420
gtccagcacg acctcaactc cggcgtcttc aactaccagg agaatgagat catccagcag     480
attgtgcagc atgaccggga gatggcccac tgcgcgcacc cgtccaggc tgctgnctct     540 gccaccccaa cccccacgcc cgtnatctgg accccgctga tccaggcacc actgcaggct     600
gccgctgcca ccacttctgt ngccatagcc ctcacccacc cccytcgcn tgnctgytgc     660 natnttnncg scctncccce anggatctnn gggctggnca amctcggtgc cggnmagang     720
ccaaggcacc tgnaacggct gnagtncctg atccctttctg cgctggtccg cctcgccgc      780 cagcagcccg tcccaggtgg acacaccgtc ttcatcctcc ttccacatcc aacagctggc     840
tggattctct gccccgctg gactgagccc actcctgccc tcatccagct cctccccacc     900
ccccggggcc tgtggctccc cctcggctcc cacaccatca gctgcgtagc cgccaccacc     960
atagccgggt ttggccactt ccacaaggcg ctgggtggct ccctgtcctc ctccgactct    1020
cccctgctca ccccgctgca gccaggcgcc cgctccccgc aggctgccca gccatctccc    1080
gcgccacccg gggccggggg aggcctggga ctcccggagc acttcctgcc accccaccc     1140 tcatccagat ccccgtcatc tagcccccggg cagctggggcc agcctccgg ggagttgtcc    1200
```

-continued

| | |
|---|---|
| ctaggtctgg ccactggccc actgagcacg ccagagacac ccccacggca gcctgagccg | 1260 |
| ccgtcccttg tggcaggggc ctctgggggn ggnttcccst gtaggncttt actccccgag | 1320 |
| gaggtntcag cccccstggn ccacagccna gsccccnaa gaaccttccc gagtgccccg | 1380 |
| ccccggncnt ctggctccca crgantcnnn cttryycctg ccacctgcat ccagccccc | 1440 |
| accaccccag ntcccccagc gccgggncac accccgctc accccgcc gcctcaccca | 1500 |
| ggacctcaag ctcatctccg cgtctcagcc agccctgcct caggacgggg cgcagactct | 1560 |
| ccgcagagcc tccccgcact cctcagggga gtccatggct gccttccgc tcttccccag | 1620 |
| ggctgggggt ggcagcgggg gcagtgggag cagcggggc ctcggtcccc ctgggaggcc | 1680 |
| ctatggtgcc atccccggcc agcacgtcac tctgcctcgg aagacatcct caggttcttt | 1740 |
| gccacccct ctgtctttgt ttggggcaag agccacctct tctgggggc ccctctgac | 1800 |
| tgctggaccc cagagggaac ctggggccag gcctgagcca gtgcgctcca aactgccgtc | 1860 |
| caatctatga gctgggccct tccttccctc ttctttcttc ttttctctcc cttccttctt | 1920 |
| ccttcaggtt taactgtgat taggagatat accaataaca gtaataatta tttaaaaaac | 1980 |
| cancasacac cagaaaaaca aaagacrrnc agaaagtcga cgcggccgc | 2029 |

<210> SEQ ID NO 12
<211> LENGTH: 2984
<212> TYPE: DNA
<213> ORGANISM: Bos taurus

<400> SEQUENCE: 12

| | |
|---|---|
| gggcaccagc cgcgccggag cccggagcgc agccactgag ggcagcggcg gcggcgggag | 60 |
| cgaggcgcgc agcgagaagc ggcgcggcg ggaagcagaa gccgccgccg ccgccgccgc | 120 |
| cgccgcgacg ggcagccggg ctcggcggcc gccggatcgg gcccctgccc cctccgcctc | 180 |
| gtgtccccgg cgccgggcgg ccggcgagtc tggagcccgc gccgtcgccg gccgcgtccc | 240 |
| ccgggcatgg aaggaggcgg caagcccaac tcctcgtcca acagccggga cgatggcaac | 300 |
| agcgtcttcc ccaccaaggc gcccgcgacg ggcgcgggc cggccgcggc cgagaagcgc | 360 |
| ctgggcaccc cgccggggg cggcgggacc ggcgcgaagg agcacggcaa ctcagtgtgc | 420 |
| ttcaaggtgg acgcggcgg cggcggcggc gaggaatcgg ccgggggctt cgaggacgcc | 480 |
| gaggggcccc ggcggcagta cggcttcatg cagcggcagt tcacctccat gctgcagccc | 540 |
| gggtcaaca aattctccct ccgcatgttc gggagccaga aggcggtgga aaggagcag | 600 |
| gaaagggtta aaactgcagg cttctggatt atccacccctt acagtgattt caggttttat | 660 |
| tgggatttaa taatgcttat aatgatggtt ggaaatctgg tcatcatacc agttggaatc | 720 |
| acattcttta cagaacagac aacaaccaca tggattattt tcaatgtggc ttcagataca | 780 |
| gttttccttt tggacttgat catgaatttc aggactggga ctgtcaatga agacagttct | 840 |
| gaaatcatcc tggaccctaa agtgatcaag atgaattatt taaaaagctg gtttgtggtt | 900 |
| gacttcatct catcaatccc agtggattat atctttctca ttgtagaaaa aggaatggat | 960 |
| tcggaagttt acaagacagc cagggcactt cgcattgtga ggtttacaaa aattctcagt | 1020 |
| ctcttgcgtt tattacgact ttcaaggtta attagataca tacatcagtg ggaagagatt | 1080 |
| ttccacatga catatgatct tgccagtgct gtggtgagaa tttttaacct cattggcatg | 1140 |
| atgctgctcc tgtgccactg ggatggctgt cttcagttcc tggtaccact gctgcaggac | 1200 |
| ttcccaccag attgctgggt gtctctaaat gagatggtta atgattcttg ggaaagcag | 1260 |
| tattcctacg cgctcttcaa agcgatgagt catatgctgt gcattggcta cggagcccaa | 1320 |

```
gcccccgtga gcatgtctga cctgtggatc accatgctga gcatgatcgt cggggccacc    1380
tgctacgcca tgtttgttgg ccacgccacg gctctaattc agtctttgga ttcctcaagg    1440
cggcaatatc aagagaagta taagcaagtg aacaataca tgtcattcca taagttacca    1500
gctgatatgc gtcagaagat acatgattat tatgaacaca gataccaagg caaaatcttt    1560
gatgaggaaa atattctcaa tgaactcaat gatcctctga gagaggagat agtcaacttc    1620
aactgccgaa actagtggc tacaatgcct cttttttgcta atgcggatcc taatttcgtg    1680
accgccatgc tgagcaagtt gagatttgag gtgtttcaac ctggagatta tatcatacga    1740
gaaggagctg tgggtaaaaa aatgtatttc attcaacatg gtgttgctgg tgtcatcaca    1800
aaatccagta agaaatgaa gctgacagat ggctcatact ttggagagat ttgcttgctg    1860
accaagggac ggcgcactgc cagtgttcga gctgatacat attgtcgtct ttactcactt    1920
tctgtggaca atttcaatga ggtcctggag gaatatccaa tgatgagaag agcctttgag    1980
acggttgcca ttgaccgatt agataggata gggaagaaaa attcaattct cctgcaaaag    2040
ttccagaagg atctgaacac gggtgttttc aacaatcagg agaacgagat cctgaagcag    2100
attgtgaaac acgacaggga aatggtgcag gcaatccctc ccctcaatta ccctcaaatg    2160
acagccctga attccacctc ttcaactact ccccgacct ctcgcctgag gacacagtca    2220
ccgccagtgt acacagccac cagtctgtct catagcaacc tgcactcccc cagccccagc    2280
acccagaccc cccagccgtc agccatcctc tcgccctgct cctacaccac cgctgtctgc    2340
agccctcctg tacagagccc gctagccact cgaactttcc actatgcctc ccccacggct    2400
tcccagttgt ccctcattca gcagcagcag gttcagcagc accgcagcc ccagcagcca    2460 ccccaacctc cacagacccc cggcagctcc acaccgaaaa acgaagtgca caagagcacg    2520
caggcgcttc acaacaccag cctgaccga gaagtcaggc ccctctcggc ctcgcagccc    2580
tcgctgcccc acgaggtctc caccctgatc tccagaccgc atcccactgt gggcgagtcc    2640
ctggcctcca tccctcaacc cgtgaccacg tccacggct cgggcctgca ggcaggggc    2700 aggggcaccg tccccagcg agtcaccctg ttccgacaga tgtcatcggg agccatcccc    2760
cccaatcgag gagtcccccc ggcccccct ccaccagcag ccgctcatcc gagggaggcg    2820
ccctcagtct taactacaga ctcagaggca gaaaagccac gatttgcttc aaatttatga    2880
tcctgctgat tgtaaagcag aaagaaatac tctaacgtaa ctgaggacgc ttctcagatt    2940
tgattttatt ctatctcctg atagatcctc tagcctacta tgaa                   2984
```

<210> SEQ ID NO 13
<211> LENGTH: 794
<212> TYPE: DNA
<213> ORGANISM: Rattus rattus

<400> SEQUENCE: 13

```
tgcctgcagt tcctggtgcc catgctgcaa gacttcccca gcgactgctg gtgtccatca     60
acaacatggt gaaccactcg tggagcgaac tctattcgtt cgcgctcttc aaggccatga    120
gccacatgct ctgtattggc tacgggcggc aggtcccga gagcatgacg gacatctggc    180
tcaccatgct cagcatgatc gtgggcgcca cctgctacgc tatgttcatt ggcacgccaa    240
cggcgcttat ccagtccctg gactcgtcac ggcgccagta ccaggagaag tacaagcaag    300
tggagcagta catgtccttc cacaaactgc cggctgactt ccgccagaag atccacgatt    360
actatgaaca ccggtaccag gggaagatgt ttgacgagga cagcatcctg ggggaactca    420
```

| | | |
|---|---|---|
| acggcccact gcgtgaggag attgtgaact tcaactgccg gaagctggtg gcttccatgc | 480 |
| cgttgtttgc caacgcagac cccaacttcg tcaccgccat gctgacaaag ctcaaatttg | 540 |
| aggtcttcca gcctggagac tacatcatcc gagaggggac catcgggaag aagatgtact | 600 |
| tcatccagca cggggtggtg agcgtgctca ccaagggcaa caaggagatg aagctgtcag | 660 |
| atggctccta ttttgggag atctgcctgc tcacgagggg ccggcgcaca gccagtgtgc | 720 |
| gggctgacac ctactgtcgc ctctactcac tgagcgtgga caacttcaac gaggtgctgg | 780 |
| aggagtaccc catg | 794 |

<210> SEQ ID NO 14
<211> LENGTH: 649
<212> TYPE: DNA
<213> ORGANISM: Rattus rattus

<400> SEQUENCE: 14

| | | |
|---|---|---|
| tccagcatgg gctgctcagt gtgttggcac ggggcgctcg ggacactcgc ctcactgacg | 60 |
| gatcctactt tggggagatc tgcttgctga ctcgaggtcg agaacagcc agtgtaaggg | 120 |
| ctgacaccta ctgtcgcctc tactcactca gcgtggacca cttcaatgca gtgcttgagg | 180 |
| agctcccgat gatgcgcagg gcttttgaga ctgtggccat ggaccggctt cggcgcatcg | 240 |
| gcaaaaagaa ttcgatattg cagcggaaac gctctgagcc gagtccaggc agcagcagtc | 300 |
| gtggcgtcat ggagcagcat ttggtacaac acgacagaga catggctcgt ggtattcggg | 360 |
| gtctggctcc gggcacagga gcccgcctca gtggaaagcc agttctgtgg gaaccactgg | 420 |
| tacacgcacc tcttcaggca gctgctgtga cctccaacgt ggccatagcc ttgactcatc | 480 |
| agcgaggccc tctgcccctc tccctgatt ctccagccac cctcctggct cgatctgcta | 540 |
| gacgctcagc aggctcccca gcctccccac tggtgcctgt tcgagcaggt cctctgctgg | 600 |
| cccgggac ctgggcgtcc acttctcatc ttcctgccca cgggccctc | 649 |

<210> SEQ ID NO 15
<211> LENGTH: 4751
<212> TYPE: DNA
<213> ORGANISM: Homo sapiens

<400> SEQUENCE: 15

| | | |
|---|---|---|
| tcgacaaaaa tgccagggaa aggcgagccc agagcttggt gatggagaaa ttgggaagcc | 60 |
| accccccacc cttcaatctt aggatgggga attcgcaact gaagccggag cttcagactt | 120 |
| ggggcgcact cccagcttag cccaggaaag agatttaagg gcgcagcagt gtggatacct | 180 |
| ctcaccccgg ccccgaaggt ctagcgaggg tctaacctgg gccccttgcc aggcccgccc | 240 |
| cccgcccctt tccagccccc ggcccgtgcg ccgctgcccc tttaagaagc ccaggtaggc | 300 |
| aggcccggct gctggagccg ctcctatggc aacccgcgag ctgcggcggc ttcatgaata | 360 |
| ttccggggcg cgggagcccg agcgctgccg gagggcgctt cggggaggc ggccgctgat | 420 |
| gtaagcccgg cgggtcgctg ggctccgctc ggttgcggcg ggagcccgg acgggccgg | 480 |
| acgggccggg gcagaggagg cgaggcgagc tcgcgggtgg ccagccacaa agcccgggcg | 540 |
| gcgagacaga cggacagcca gccctcccgc gggacgcacg cccgggaccc gcgcgggccg | 600 |
| tgcgctctgc actccggagc ggttccctga gcgccgcggc cgcagagcct tccggccgg | 660 |
| cgcccattgt tccccgcggg ggcggggcgc ctggagccgg gcggcgcgcc gccctgaac | 720 |
| gccagaggga gggagggagg caagaaggga gcgcggggtc cccgcgccca gccgggcccg | 780 |
| ggaggaggtg tagcgcggcg agcccgggga ctcggagcgg gactaggatc ctccccgcgg | 840 |

```
cgcgcagcct gcccaagcat gggcgcctga ggctgccccc acgccggcgg caaaggacgc      900
gtccccacgg gcggactgac cggcgggcgg acctggagcc cgtccgcggc gccgcgctcc      960 tgccccggc  ccgtccgac  cccggcccct ggcgccatgg acaagctgcc gccgtccatg     1020
cgcaagcggc tctacagcct cccgcagcag gtggggccca aggcgtggat catggacgag     1080
gaagaggacg ccgaggagga gggggccggg ggccgcaag  accccagccg caggagcatc     1140
cggctgcggc cactgccctc gccctccccc tcggcggccg cgggtggcac ggagtcccgg     1200
agctcggccc tcggggcagc ggacagcgaa gggccgcccc gcggcgcggg caagtccagc     1260
acgaacggcg actgcaggcg cttccgcggg agcctggcct cgctgggcag ccggggcggc     1320
ggcacgggcg gcacggggag cggcagcagt cacggacacc tgcatgactc gcggaggag     1380 cggcggctca tcgccgaggg cgacgcgtcc cccggcgagg acaggacgcc cccaggcctg     1440
gcggccgagc ccgagcgccc cggcgcctcg gcgcagcccg cagcctcgcc gccgccgccc     1500
cagcagccac cgcagccggc ctccgcctcc tgcgagcagc cctcggtgga caccgctatc     1560
aaagtggagg gaggcgcggc tgccggcgac cagatcctcc cggaggccga ggtgcgcctg     1620
ggccaggccg gcttcatgca cgccagttc  ggggccatgc tccaacccgg ggtcaacaaa     1680
ttctccctaa ggatgttcgg cagccagaaa gccgtggagc gcgaacagga gagggtcaag     1740
tcggccggat tttggattat ccaccctac  agtgacttca gattttactg ggacctgacc     1800
atgctgctgc tgatggtggg aaacctgatt atcattcctg tgggcatcac cttcttcaag     1860
gatgagaaca ccacaccctg gattgtcttc aatgtggtgt cagacacatt cttcctcatc     1920
gacttggtcc tcaacttccg cacagggatc gtggtggagg acaacacaga gatcatcctg     1980
gacccgcagc ggattaaaat gaagtacctg aaaagctggt tcatggtaga tttcatttcc     2040
tccatccccg tggactacat cttcctcatt gtggagacac gcatcgactc ggaggtctac     2100
aagactgccg ggccctgcg  cattgtccgc ttcacgaaga tcctcagcct cttacgcctg     2160
ttacgcctct cccgcctcat tcgatatatt caccagtggg aagagatctt ccacatgacc     2220
tacgacctgg ccagcgccgt ggtgcgcatc gtgaacctca tcggcatgat gctcctgctc     2280
tgccactggg acggctgcct gcagttcctg gtacccatgc tacaggactt ccctgacgac     2340
tgctgggtgt ccatcaacaa catggtgaac aactcctggg ggaagcagta tcctacgcg      2400 ctcttcaagg ccatgagcca catgctgtgc atcggctacg gcggcaggc  gcccgtgggc     2460 atgtccgacg tctggctcac catgctcagc atgatcgtgg gtgccacctg ctacgccatg     2520
ttcattggcc acgccactgc cctcatccag tccctggact cctcccggcg ccagtaccag     2580
gaaaagtaca gcaggtgga  gcagtacatg tcctttcaca agctcccgcc cgacacccgg     2640
cagcgcatcc acgactacta cgagcaccgc taccagggca agatgttcga cgaggagagc     2700
atcctgggcg agctaagcga gcccctgcgg gaggagatca tcaactttaa ctgtcggaag     2760
ctggtggcct ccatgccact gtttgccaat gcggaccca  acttcgtgac gtccatgctg     2820
accaagctgc gtttcgaggt cttccagcct ggggactaca tcatccggga aggcaccatt     2880
ggcaagaaga tgtacttcat ccagcatggc gtggtcagcg tgctcaccaa gggcaacaag     2940
gagaccaagc tggccgacgg ctcctacttt ggagagatct gcctgctgac ccggggccgg     3000
cgcacagcca gcgtgagggc cgacacctac tgccgcctct actcgctgag cgtggacaac     3060
ttcaatgagg tgctggagga gtaccccatg atgcgaaggg ccttcgagac cgtggcgctg     3120
gaccgcctgg accgcattgg caagaagaac tccatcctcc tccacaaagt ccagcacgac     3180
```

-continued

```
ctcaactccg gcgtcttcaa ctaccaggag aatgagatca tccagcagat tgtgcagcat      3240
gaccgggaga tggcccactg cgcgcaccgc gtccaggctg ctgcctctgc caccccaacc      3300
cccacgcccg tcatctggac cccgctgatc caggcaccac tgcaggctgc cgctgccacc      3360
acttctgtgg ccatagccct cacccaccac cctcgcctgc ctgctgccat cttccgccct      3420
cccccaggat ctgggctggg caacctcggt gccgggcaga cgccaaggca cctgaaacgg      3480
ctgcagtccc tgatcccttc tgcgctgggc tccgcctcgc ccgccagcag cccgtcccag      3540
gtggacacac catcttcatc ctccttccac atccaacagc tggctggatt ctctgccccc      3600
gctggactga gcccactcct gccctcatcc agctcctccc cacccccgg ggcctgtggc       3660 tccccctcgg ctcccacacc atcagctggc gtagccgcca ccaccatagc cgggtttggc      3720
cacttccaca aggcgctggg tggctccctg tcctcctccg actctcccct gctcaccccg      3780
ctgcagccag gcgcccgctc cccgcaggct gcccagccat ctcccgcgcc accgggggcc     3840
cggggaggcc tgggactccc ggagcacttc ctgccacccc cacctcatc cagatccccg       3900 tcatctagcc ccgggcagct gggccagcct cccggggagt tgtccctagg tctggccact      3960
ggcccactga gcacgccaga gacaccccca cggcagcctg agccgccgtc ccttgtggca      4020
ggggcctctg gggggcttc ccctgtaggc tttactcccc gaggaggtct cagccccct       4080 ggccacagcc caggcccccc aagaaccttc ccgagtgccc cgccccgggc ctctggctcc      4140
cacggatcct tgctcctgcc acctgcatcc agcccccac caccccaggt ccccagcgc       4200 cggggcacac ccccgctcac ccccggccgc ctcacccagg acctcaagct catctccgcg     4260
tctcagccag ccctgcctca ggacggggcg cagactctcc gcagagcctc cccgcactcc      4320
tcaggggagt ccatggctgc cttcccgctc ttccccaggg ctgggggtgg cagcggggggc     4380 agtgggagca gcgggggcct cggtccccct gggaggccct atggtgccat ccccggccag      4440
cacgtcactc tgcctcggaa gacatcctca ggttctttgc caccccctct gtctttgttt      4500
ggggcaagag ccacctcttc tggggggccc cctctgactg ctggaccca gagggaacct       4560 ggggccaggc ctgagccagt gcgctccaaa ctgccgtcca atctatgagc tgggcccttc     4620
cttccctctt cttctcttt ttctctccct tccttcttcc ttcaggttta actgtgatta      4680
ggagatatac caataacagt aataattatt taaaaaacca cacacaccag aaaaacaaaa     4740
gacagcagaa a                                                          4751
```

<210> SEQ ID NO 16
<211> LENGTH: 29
<212> TYPE: DNA
<213> ORGANISM: Artificial Sequence
<220> FEATURE:
<223> OTHER INFORMATION: Degenerated Primer
<220> FEATURE:
<221> NAME/KEY: MISC_FEATURE
<222> LOCATION: (15)..(15)
<223> OTHER INFORMATION: "n" may be any nucleotide.
<220> FEATURE:
<221> NAME/KEY: MISC_FEATURE
<222> LOCATION: (24)..(24)
<223> OTHER INFORMATION: "n" may be any nucleotide.
<220> FEATURE:
<221> NAME/KEY: MISC_FEATURE
<222> LOCATION: (27)..(27)
<223> OTHER INFORMATION: "n" may be any nucleotide.

<400> SEQUENCE: 16

```
ctgactgcag argtnttyca rccnggnga                                         29
```

-continued

```
<210> SEQ ID NO 17
<211> LENGTH: 28
<212> TYPE: DNA
<213> ORGANISM: Artificial Sequence
<220> FEATURE:
<223> OTHER INFORMATION: Degenerated Primer
<220> FEATURE:
<221> NAME/KEY: MISC_FEATURE
<222> LOCATION: (11)..(11)
<223> OTHER INFORMATION: "n" may be any nucleotide.
<220> FEATURE:
<221> NAME/KEY: MISC_FEATURE
<222> LOCATION: (20)..(20)
<223> OTHER INFORMATION: "n" may be any nucleotide.
<220> FEATURE:
<221> NAME/KEY: MISC_FEATURE
<222> LOCATION: (23)..(23)
<223> OTHER INFORMATION: "n" may be any nucleotide.

<400> SEQUENCE: 17
atcggaattc nccraartan ganccrtc                                        28

<210> SEQ ID NO 18
<211> LENGTH: 767
<212> TYPE: PRT
<213> ORGANISM: Strongylocentrotus purpuratus

<400> SEQUENCE: 18
```

Met Asp Asn Lys Glu Thr Asn Gly Glu Leu Glu Gln Ser Asp Glu Ala
 1               5                  10                  15

Asp Pro Ser Gly Gln Asn Leu Asp Asp Gly Glu Thr Asp Ser Lys Gln
            20                  25                  30

Glu Glu Asn Leu Ile Asn Val Ser Pro Pro Lys Thr Pro Pro Gly Pro
        35                  40                  45

Pro Pro Leu Lys Asn Gly Gly Arg Gly Gln Lys Pro Pro Lys Ile
    50                  55                  60

Pro Ile Cys His Gln Asn Gly Lys Leu Pro Lys Glu Val Glu Trp Thr
 65                  70                  75                  80

Glu Asp Arg Gly Glu Asp Arg Lys Asp Ser Leu Thr Leu Gln Ser Lys
                85                  90                  95

Leu Asp His Gly Ala Tyr Thr Asp Glu Lys Gln Asp Leu Leu Thr Tyr
            100                 105                 110

Leu Asp Arg His Gly Ile Asn Ser Pro Val Lys Leu Thr Pro Asp Glu
        115                 120                 125

Thr Gly Gly Ser Ser Ala Leu Asp Ile Leu Gly Ile Ile Glu Glu Arg
    130                 135                 140

Asp Thr Gly Ala Leu Gly Ser Asp Pro Ser Ser Thr Met Gln Ala Met
145                 150                 155                 160

Ala Lys Pro Val Gly Phe Leu Gln Arg Gln Leu Trp Thr Val Leu Gln
                165                 170                 175

Pro Ser Asp Asn Arg Leu Ser Met Lys Leu Phe Gly Ser Lys Lys Gly
            180                 185                 190

Leu Gln Lys Glu Lys Tyr Arg Leu Arg Lys Ala Gly Val Leu Ile Ile
        195                 200                 205

His Pro Cys Ser His Phe Arg Phe Tyr Trp Asp Leu Leu Met Leu Cys
    210                 215                 220

Leu Ile Met Ala Asn Val Ile Leu Leu Pro Val Val Ile Thr Phe Phe
225                 230                 235                 240

His Asn Lys Asp Met Ser Thr Gly Trp Leu Ile Phe Asn Cys Phe Ser
                245                 250                 255

-continued

```
Asp Thr Phe Phe Ile Leu Asp Leu Ile Cys Asn Phe Arg Thr Gly Ile
            260                 265                 270

Met Asn Pro Lys Ser Ala Glu Gln Val Ile Leu Asn Pro Arg Gln Ile
        275                 280                 285

Ala Tyr His Tyr Leu Arg Ser Trp Phe Ile Ile Asp Leu Val Ser Ser
    290                 295                 300

Ile Pro Met Asp Tyr Ile Phe Leu Leu Ala Gly Gly Gln Asn Arg His
305                 310                 315                 320

Phe Leu Glu Val Ser Arg Ala Leu Lys Ile Leu Arg Phe Ala Lys Leu
                325                 330                 335

Leu Ser Leu Leu Arg Leu Leu Arg Leu Ser Arg Leu Met Arg Phe Val
            340                 345                 350

Ser Gln Trp Glu Gln Ala Phe Asn Val Ala Asn Ala Val Ile Arg Ile
        355                 360                 365

Cys Asn Leu Val Cys Met Met Leu Leu Ile Gly His Trp Asn Gly Cys
    370                 375                 380

Leu Gln Tyr Leu Val Pro Met Leu Gln Glu Tyr Pro Asp Gln Ser Trp
385                 390                 395                 400

Val Ala Ile Asn Gly Leu Glu His Ala His Trp Trp Glu Gln Tyr Thr
                405                 410                 415

Trp Ala Leu Phe Lys Ala Leu Ser His Met Leu Cys Ile Gly Tyr Gly
            420                 425                 430

Lys Phe Pro Pro Gln Ser Ile Thr Asp Val Trp Leu Thr Ile Val Ser
        435                 440                 445

Met Val Ser Gly Ala Thr Cys Phe Ala Leu Phe Ile Gly His Ala Thr
    450                 455                 460

Asn Leu Ile Gln Ser Met Asp Ser Ser Arg Gln Tyr Arg Glu Lys
465                 470                 475                 480

Leu Lys Gln Val Glu Glu Tyr Met Gln Tyr Arg Lys Leu Pro Ser His
                485                 490                 495

Leu Arg Asn Lys Ile Leu Asp Tyr Tyr Glu Tyr Arg Tyr Arg Gly Lys
            500                 505                 510

Met Phe Asp Glu Arg His Ile Phe Arg Glu Val Ser Glu Ser Ile Arg
        515                 520                 525

Gln Asp Val Ala Asn Tyr Asn Cys Arg Asp Leu Val Ala Ser Val Pro
    530                 535                 540

Phe Phe Val Gly Ala Asp Ser Asn Phe Val Thr Arg Val Thr Leu
545                 550                 555                 560

Leu Glu Phe Glu Val Phe Gln Pro Ala Asp Tyr Val Ile Gln Glu Gly
                565                 570                 575

Thr Phe Gly Asp Arg Met Phe Phe Ile Gln Gln Gly Ile Val Asp Ile
            580                 585                 590

Ile Met Ser Asp Gly Val Ile Ala Thr Ser Leu Ser Asp Gly Ser Tyr
        595                 600                 605

Phe Gly Glu Ile Cys Leu Leu Thr Arg Glu Arg Val Ala Ser Val
    610                 615                 620

Lys Cys Glu Thr Tyr Cys Thr Leu Phe Ser Leu Ser Val Gln His Phe
625                 630                 635                 640

Asn Gln Val Leu Asp Glu Phe Pro Ala Met Arg Lys Thr Met Glu Glu
                645                 650                 655

Ile Ala Val Arg Arg Leu Thr Arg Ile Gly Lys Glu Ser Ser Lys Leu
            660                 665                 670

Lys Ser Arg Leu Glu Ser Pro Thr Ile Arg Asp Thr Ala Pro Leu Phe
```

-continued

```
            675                 680                 685
Pro Ile Pro Pro Asp Thr Pro Ser Phe Val Thr Asp Ile Glu Lys Asn
    690                 695                 700

Arg Phe Phe Gly Asp Asp Thr Asp Asp Val His Ile Arg Thr Arg Val
705                 710                 715                 720

Asp Val Glu Arg Gly Ser His Glu Asn Val Ile Ala Ile Met Asp Gly
                725                 730                 735

Ser Leu Ser Asp Leu Arg Met Glu Asn Glu Ile Gln Ala Arg Lys Ser
                740                 745                 750

Ser Ser Gly Lys Arg Arg Lys Phe Gln Gln Gln Thr Thr Glu Leu
                755                 760                 765

<210> SEQ ID NO 19
<211> LENGTH: 23
<212> TYPE: PRT
<213> ORGANISM: Artificial
<220> FEATURE:
<223> OTHER INFORMATION: Synthetic

<400> SEQUENCE: 19

Thr Trp Ala Leu Phe Lys Ala Leu Ser His Met Leu Cys Ile Gly Tyr
1               5                   10                  15

Gly Lys Phe Pro Pro Gln Ser
            20

<210> SEQ ID NO 20
<211> LENGTH: 23
<212> TYPE: PRT
<213> ORGANISM: Artificial
<220> FEATURE:
<223> OTHER INFORMATION: Synthetic

<400> SEQUENCE: 20

Pro Asp Ala Phe Trp Trp Ala Val Val Thr Met Thr Thr Val Gly Tyr
1               5                   10                  15

Gly Asp Met Thr Pro Val Gly
            20
```

SEQUENCES OF AN $I_h$ ION CHANNEL AND USE THEREOF

CROSS-REFERENCE TO RELATED APPLICATIONS

This patent application is a divisional of copending U.S. patent application Ser. No. 09/640,582, filed August 17, 2000.

The present invention relates to a nucleic acid, preferably a DNA, comprising at least part of the sequence of an $I_h$ ion channel. Said sequence may e.g. be derived from a human DNA, a rat DNA, a bovine DNA, a *Drosophila melanogaster* DNA or a sea urchin DNA. Furthermore, the present invention relates to an mRNA molecule which contains the corresponding sequences. The invention further relates to a polypeptide or protein comprising the corresponding derived amino acid sequence.

Furthermore, the invention relates to the use of one or more of the above-mentioned sequences in a screening and/or diagnosing method and to the kits required therefor.

Lastly, the invention relates to the use of one or more of the above-mentioned sequences for the treatment and/or prophylaxis of cardiovascular disorders and sleep disturbances.

The many different functions of the nerve system are substantially determined by finely adjusted interactions between the intrinsic characteristics of the neurons and the synaptic connections. The electrophysiological characteristics inherent to the neurons and synapses are, in turn, determined by the localization and density of the voltage- and ligand-controlled ion channels which regulate the flow of ion currents across the neuronal plasma membrane and which are controlled by a great number of transmitter substances and intracellular messenger systems (Hille, 1992).

With regard to the specific activity expected of the neuronal elements, it is not astonishing that neurons have a great repertory of ion channels, including the classic channels that produce voltage-dependent sodium ($Na^+$) and potassium ($K^+$) currents during an action potential (Hodgkin and Huxley, 1952) and also a number of unusual ion conductances (Unas, 1988).

An unusual intrinsic mechanism which had originally been discovered by Ito and colleagues (Araki et al., 1962; Ito and Oshima, 1965) in motoneurons of cats turned out to be a slow relaxation of the potential change induced by hyperpolarizing current, resulting in a non-ohmic behavior of the current/voltage (I/V) relationship in hyperpolarizing direction. The underlying time-dependent membrane current was first characterized in photoreceptors of the rods as cesium ($Cs^+$-sensitive inward current which is triggered by hyperpolarization and may depolarize the membrane. This leads to the typical sequence of an initial transient hyperpolarization by exposure, followed by a slow depolarization (Attwell and Wilson, 1980; Bader et al., 1982; Bader et al., 1979; Fain et al., 1978).

The current in the photoreceptors was designated as $I_h$ because it is activated by hyperpolarization. At about the same time a similar ion current was discovered in the heart, in the pacemaker cells of the sinus node and in the Purkinje fibers of the mammalian heart (Brown and Di Francesco, 1980; Brown et al., 1979; Di Francesco, 1981 a; Di Francesco, 1981b; Yanagihara and Irisawa, 1980), and it became clear that the slow inward current is accompanied by sodium and potassium ions. This current was called "funny" current ($I_f$) to emphasize its unusual behavior, i.e., the fact that an inward current is concerned which is activated by hyperpolarization and, oddly enough, was similar to the previously described $K^+$ conductance $I_{K2}$. There is a growing interest in said current because it participates, for instance, in the generation and control of spontaneous activity of the heart.

Further evidence of the presence of a corresponding current in central neurons was found, and it was mentioned by Halliwell and Adams (1982) for the first time. They observed a slow inward current, which was designated as "queer" current ($I_q$), in pyramidal cells of the hippocampus after hyperpolarization. Subsequently, currents with similar characteristics were found in a great number of neuronal and non-neuronal cells, and said hyperpolarization-activated current was finally recognized as an omnipresent phenomenon in cells of the nerve system. The designation as "$I_h$" is now accepted as a term for describing said current.

Although it was first assumed that the activity of the respective $I_h$ channels is not modulated, more and more data show that the $I_h$ channels are important targets for neurotransmitters and messenger systems, which emphasizes their important physiological role in the control of cellular electrical activities.

In the meantime it has become known that $I_h$ significantly contributes to the rest potential, limits an excessive hyperpolarization, determines the form of action patterns (firing patterns) and takes part in the generation of rhythmic oscillations of the membrane potential. $I_h$ currents have a few special characteristics that distinguish the same from other voltage-controlled ion channels. Like voltage-controlled $Na^+$, $Ca^{2+}$ and specific $K^+$ currents, they have a steep voltage-dependence curve and activate with a sigmoidal time course; they are however activated by hyperpolarization and deactivate by sigmoidal kinetics.

The activation in negative potentials and the blockage by $Cs^+$ ions reminds of inwardly rectifying $K^+$ channels. However, many characteristics of $I_h$ clearly differ from that $K^+$ channel family: The activation kinetics is slower, the activation range is more positive and is independent of the extracellular $K^+$ concentration, conductance is substantially resistant to extracellular $Ba^{2+}$ ions and the $I_h$ channels are permeable not only to $K^+$ ions, but also to $Na^+$ ions. In contrast to other cation channels, such as ligand-controlled cation channels, the $I_h$ channels are very selective for $Na^+$ and $K^+$ ions and have a steep voltage-dependent control.

Of particular importance to the present research work is the participation of the $I_h$ channels in the pacemaker function in the cardiac muscle. The pacemaker activity in the heart is due to specialized myocytes that are located in specific regions of the heart (sinus venosus) and are characterized by their ability to beat spontaneously even if separated from the rest of the cardiac muscle. In pacemaker cells of the sinus node in mammals, the spontaneous activity follows from a typical phase of their action potential, the slow diastolic depolarization. During said phase, which corresponds to the diastole of the cardiac contraction cycle, the membrane depolarizes again at a slow pace after termination of the action potential until the threshold value for the generation of a new action potential is reached. Thus the diastolic depolarization is responsible for the initiation of the rhythmic behavior and characterizes action potentials of the sinus node and other spontaneously active cardiocytes.

Apart from the generation of a rhythmic activity, the diastolic (or pacemaker) depolarization takes part in the control of the heartbeat frequency by autonomous neurotransmitters. It is known that the stimulation of the sympathic and parasympathic nerve system leads to an acceleration and deceleration of the heartbeat.

It has become known in the meantime that the $I_h$ channels take part in this pacemaker function. The $I_h$ current of the sinus node is an unspecific cation current, normally accompanied by Na⁺ and K⁺, which after hyperpolarization slowly activates in a voltage range encompassing that of the diastolic depolarization. The $I_h$ features are well suited for producing a depolarization process as a reaction to a hyperpolarization in a voltage range in which the $I_h$ channel is activated.

So far, however, it has not been possible to identify sequences of genes coding for $I_h$ ion channels. Furthermore, channel protein has so far not been available in a sufficient amount for characterizing the same biochemically. Finally, the pharmacological characterization of $I_h$ channels has so far been extremely difficult because the $I_h$ currents were identified on whole cells, which additionally exhibit K⁺- and Na⁺-selective conductivities, and were experimentally isolated from the other currents.

It has therefore been the object of the present invention to indicate the nucleic acid, to show its possible applications, and to provide the protein in a functional state and in a sufficient amount for biochemical analyses and pharmaceutical applications.

Said object is achieved by the subject matter of the independent claims. Advantageous developments are indicated in the dependent claims.

The terms used hereinafter shall have the following meanings:

"$I_h$ ion channel" is here to stand for those ion channels that (1) open by hyperpolarization and are closed at more positive voltage values ($V_m \geq 10$ mV); (2) whose activation and deactivation take place with a relatively slow sigmoidal time course; (3) conduct not only K⁺ ions, but also Na⁺ ions; (4) are almost entirely blocked by 0.1-3 mM extracellular Cs⁺ and (5) are directly modulated by cyclic nucleotides, in particular cyclo AMP and cyclo GMP.

"Stringent conditions" means hybridization with 0.1-5× SSC, preferably 1-2×SSC, at 60-70° C., preferably 65° C.

"Conditions of low stringency" means hybridization at 0.1-5×SSC, preferably 1-2×SSC at 50-60° C., preferably at 55° C.

"Parts" of the $I_h$ ion channel means a section of the protein sequence suited as antigenic determinant, for example, a section of at least 6 amino acids. Sections that occur in the form of domains, such as the sections S1, S2, etc. as indicated in FIG. 1A, are also regarded as parts. This encompasses sections of the ion channel that derive from the DNA sequences indicated in SEQ ID NO: 1 to 15 using the IUPAC code, namely by way of amino acid exchanges, deletions and additions, while maintaining the biological function.

"Part" thereof in connection with the nucleic acid means a fragment having a length of at least 6 nucleotides, preferably 12 nucleotides, particularly preferably a length of 18 nucleotides. The part is suited for hybridizing via oligonucleotide hybridization specifically (selectively) with the corresponding total sequence. Thus a "part" of the nucleic acid is a section from the sequences according to SEQ ID NO: 1 to 15 that is suited for selectively hybridizing with one of the said sequences.

"Selectively" (specifically) means that under suitable hybridization conditions a nucleic acid only hybridizes with one nucleic acid as is indicated by one of the sequences according to SEQ ID NO: 1 to 15, whereas it does not hybridize with another nucleic acid of the respective host organism with which it is normally associated.

"Homology" as is here used is calculated as follows: The amino acids are counted in the sequences or sequence sections to be compared that are either identical or similar at the respective position. This number is divided by the total number of the amino acid residues and multiplied by 100. This yields a percentage of the sequence similarity or homology. This is illustrated by the sample given below:

```
TWALFKALSHMLCIGYGKFPPQS     [SEQ ID NO: 19]

PDAFWWAVVTMTTVGYGDMTPVG     [SEQ ID NO: 20]
```

The total number of the positions to be compared with one another is 23 residues; there are 7 identically and 6 similarity occupied amino acid positions. That is why the homology (7+6)/23×100=56.5%. An exchange of similar amino acids is also designated as a conservative exchange (cf. Dayhoff et al., 1978).

The above isolated or purified nucleic acid molecules also can be characterized in terms of "percentage of sequence identity." In this regard, a given nucleic acid molecule as described above can be compared to a nucleic acid molecule encoding a corresponding gene (i.e., the reference sequence) by optimally aligning the nucleic acid sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleic acid base occurs in both sequences, i.e., the number of matched positions, dividing the number of matched positions by the total number of positions in the window of comparison, and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information, Bethesda, Md.), or by inspection. Sequences are typically compared using BESTFIT or BlastN with default parameters.

"Substantial sequence identity" means that at least 75%, preferably at least 80%, more preferably at least 90%, and most preferably at least 95% of the sequence of a given nucleic acid molecule is identical to a given reference sequence. Typically, two polypeptides are considered to be substantially similar if at least 40%, preferably at least 60%, more preferably at least 90%, and most preferably at least 95% of the amino acids of which the polypeptides are comprised are identical to or represent conservative substitutions of the amino acids of a given reference sequence.

One of ordinary skill in the art will appreciate, however, that two polynucleotide sequences can be substantially different at the nucleic acid level, yet encode substantially similar, if not identical, amino acid sequences, due to the degeneracy of the genetic code. The present invention is intended to encompass such polynucleotide sequences.

According to claim 1 there is provided a nucleic acid which comprises at least a part of the sequence of an $I_h$ ion channel. The nucleic acid complementary thereto is also regarded as an inventive embodiment. Said nucleic acid may preferably be derived from a human DNA and is then in particular characterized by the sequences according to SEQ ID NO: 1, SEQ ID NO: 10, SEQ ID NO: 11, and SEQ ID NO: 15.

Advantageously, the sequence may also be derived from a rat DNA and is then in particular characterized by SEQ ID NO: 2, SEQ ID NO: 8, SEQ ID NO: 9, and SEQ ID NO: 14.

In a further preferred embodiment, the sequence may be derived from a bovine DNA and is then characterized by the sequences according to SEQ ID NO: 3, SEQ ID NO: 6, SEQ ID NO: 7, and SEQ ID NO: 12.

Furthermore, the sequence may preferably be derived from a sea urchin DNA, and it is then preferably characterized by the sequence SEQ ID NO: 4.

Furthermore, the DNA may preferably be derived from *Drosophila melanogaster*. The complete sequence is then in accordance with SEQ ID NO: 5.

A particularly preferred embodiment comprises sequences that exhibit a homology of at least 80% to one of SEQ ID NO: 1 to 15. In a further preferred embodiment the sequence exhibits a homology of at least 90% to one of the sequences designated SEQ ID NO: 1 to 15.

It hybridizes in a particularly preferred manner under low stringent conditions and even more preferably under conditions of high stringency with one of the sequences designated by SEQ ID NO: 1 to 15.

The present invention covers modifications of the sequences according to SEQ ID NO: 1 to 15 which result e.g. from the degeneration of the genetic code, deletions, insertions, inversions and further mutations, the biological property of the encoded channel protein or part thereof being preferably maintained.

Furthermore, the invention relates to an mRNA molecule comprising a sequence corresponding to one of the above-described sequences. Accordingly the invention covers a polypeptide which is encoded by the above-mentioned nucleic acid.

A nucleic acid molecule as described above can be cloned into any suitable vector. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987); Birren et al., Genome Analysis: A Laboratory Manual Series, Volume 1, Analyzing DNA, Cold Spring Harbor Laboratory Press, Cold Spring Harbor, N.Y. (1997); Birren et al., Genome Analysis: A Laboratory Manual Series, Volume 2, Detecting Genes, Cold Spring Harbor Laboratory Press, Cold Spring Harbor, N.Y. (1998); Birren et al., Genome Analysis: A Laboratory Manual Series, Volume 3, Cloning Systems, Cold Spring Harbor Laboratory Press, Cold Spring Harbor, N.Y. (1999); Birren et al., Genome Analysis: A Laboratory Manual Series, Volume 4, Mapping Genomes, Cold Spring Harbor Laboratory Press, Cold Spring Harbor, N.Y. (1999); and Sambrook et al., Molecular Cloning: A Laboratory Manual, 2nd edition, Cold Spring Harbor Laboratory Press, Cold Spring Harbor, N.Y. (1989)). Desirably, the vector comprises regulatory sequences, such as transcription and translation initiation and termination codons, which are specific to the type of host into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, 2 mµ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC, series the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAM-neo (Clonetech).

An expression vector can comprise a native or nonnative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule as described above with a promoter is also within the skill in the art.

Thus, in view of the above, the present invention also provides a host cell comprising an isolated or purified nucleic acid molecule or a vector as described above. Examples of host cells include, but are not limited to, a human cell, a human cell line, *E. coli, B. subtilis, P. aerugenosa, S. cerevisiae*, and *N. crassa*. Other examples include *E. coli* TB-1, TG-2, DH5α, XL-Blue MRF' (Stratagene), SA2821 and Y1090.

The above-described sequences can be used for a screening method or also a diagnosing method. In a screening method, it is possible owing to the identification of the sequence of the $I_h$ channel to test the effect of substances on ion channels using said sequences.

Such a screening method may e.g. comprise the following steps:
  producing homogeneous channel preparations, for example, by expression of the above-mentioned nucleic acid in a suitable host, such as oocytes, mammalian cells, etc.,
  testing of substances on said channel preparations.

It can here be determined by measuring the channel activity under the action or in the absence of test substances which substances are suited for influencing the channels.

The invention also relates to a kit for performing such a screening method which comprises at least one of the above-described nucleic acids or polypeptides.

The sequences can also be used for a diagnosing method, in particular for recognizing cardiovascular disorders.

In said diagnosing method the nucleic acid of the patient is preferably contacted with a sequence section of one of the above-described DNAs and/or RNAs, whereby a signal is obtained that is indicative of the presence and/or absence of an ion-channel nucleic acid sequence. Mutations in the ion channels of the patient can also be detected by selecting suitable samples, e.g. short oligonucleotides, which in turn is of help to the differential diagnosis.

Furthermore, the present invention refers to a kit for carrying out such a diagnosing method comprising one of the above-described sequences.

Furthermore, it is possible to use the above-described sequences for the treatment and/or prophylaxis of cardiovascular disorders and disturbances of consciousness as well as pain states. In a preferred embodiment, cardiovascular disorders that are due to a faulty control of the sinus node can be treated or recognized at an early stage. Furthermore, disturbances of consciousness that are due to a malfunction of cortico-thalamic neurons are preferably recognized. For instance, within the scope of gene therapy, a fully operable ion channel as encoded by the nucleic acids described herein are introduced into a patient to replace a channel that is no longer operative.

Accordingly, the present invention provides a method of prophylactically or therapeutically treating a mammal for a cardiovascular disorder, in particular a cardiovascular disorder that is due to a faulty control of the sinus node. The method comprises administering to a mammal (i) a vector comprising and expressing a prophylactically or therapeutically effective amount of an above-described nucleic acid or (ii) a prophylactically or therapeutically effective amount of an above-described polypeptide, whereupon the mammal is treated for the cardiovascular disorder.

The present invention further provides a method of prophylactically or therapeutically treating a mammal for a disturbance of consciousness, in particular a disturbance of consciousness that is due to a malfunction in thalamic neurons. The method comprises administering to a mammal (i) a vector comprising and expressing a prophylactically or therapeutically effective amount of an above-described nucleic acid or (ii) a prophylactically or therapeutically effective amount of an above-described polypeptide, whereupon the mammal is treated for the disturbance of consciousness.

Still further provided by the present invention is a method of prophylactically or therapeutically treating a mammal for a pain state. The method comprises administering to a mammal (i) a vector comprising and expressing a prophylactically or therapeutically effective amount of an above-described nucleic acid or (ii) a prophylactically or therapeutically effective amount of an above-described polypeptide, whereupon the mammal is treated for the pain state.

Lastly, the invention relates to a pharmaceutical composition which comprises one or more of the above-described nucleic acids or the above-described polypeptide. Such a pharmaceutical composition can be used for treating cardiovascular disorders, in particular those that are due to a faulty control of the sine node, as well as disturbances of consciousness, in particular those caused by a malfunction in cortico-thalamic neurons.

Therefore, the present invention also provides a composition comprising an above-described isolated or purified nucleic acid (or vector comprising the nucleic acid) or an above-described polypeptide and a carrier therefor. Carriers, such as pharmaceutically acceptable carriers, are well-known in the art, and are readily available. The choice of carrier will be determined in part by the particular route of administration and whether a nucleic acid molecule or a polypeptide molecule is being administered. Accordingly, there is a wide variety of suitable formulations for use in the context of the present invention, and the invention expressly provide a pharmaceutical composition that comprises an active agent of the invention and a pharmaceutically acceptable carrier therefor. The following methods and carriers are merely exemplary and are in no way limiting.

Formulations suitable for oral administration can consist of (a) liquid solutions, such as an effective amount of the compound dissolved in diluent, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth. Pastilles can comprise the active ingredient in an inert base, such as gelatin and glycerin, or sucrose and acacia, emulsions, gels, and the like containing, in addition to the active ingredient, such excipients/carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Further suitable formulations are found in *Remington's Pharmaceutical Sciences,* 17th ed., (Mack Publishing Company, Philadelphia, Pa.: 1985), and methods of drug delivery are reviewed in, for example, Langer, *Science,* 249, 1527-1533 (1990).

Generally, when an above-described polypeptide is administered to an animal, such as a mammal, in particular a human, it is preferable that the polypeptide is administered in a dose of from about 1 to about 1,000 micrograms of the polypeptide per kg of the body weight of the host per day when given parenterally. However, this dosage range is merely preferred, and higher or lower doses may be chosen in appropriate circumstances. For instance, the actual dose and schedule can vary depending on whether the composition is administered in combination with other pharmaceutical compositions, or depending on interindividual differences in pharmacokinetics, drug disposition, and metabolism. One skilled in the art easily can make any necessary adjustments in accordance with the necessities of the particular situation.

If desired, the half-life of the polypeptide can be increased by conjugation to soluble macromolecules, such as polysaccharides, or synthetic polymers, such as polyethylene glycol, as described, for instance, in U.S. Pat. Nos. 5,116,964, 5,336, 603, and 5,428,130. Alternately, the polypeptides can be "protected" in vesicles composed of substances such as proteins, lipids (for example, liposomes), carbohydrates, or synthetic polymers. If liposomes are employed, liposome delivery can be carried out as described in U.S. Pat. No. 5,468,481, or using liposomes having increased transfer capacity and/or reduced toxicity in vivo (see, e.g., PCT patent application WO 95/21259 and the references cited therein). Furthermore, polypeptides can be administered in conjunction with adenovirus (preferably replication-deficient adenovirus) to allow the intracellular uptake of the polypeptides by adenoviral-mediated uptake of bystander molecules (e.g., as described in PCT patent application WO 95/21259). Similarly, a conjugate, such as one comprising a targeting moiety, or a fusion of a an above-described polypeptide to an antibody (or an antigenically reactive fragment thereof) that recognizes a cell surface antigen; etc. can be employed to deliver the resultant fusion protein to a specific target cell or tissue (e.g., as described in U.S. Pat. No. 5,314,995).

Those of ordinary skill in the art can easily make a determination of the vector to be administered to an animal, such as a mammal, in particular a human. The dosage will depend upon the particular method of administration, including any vector or promoter utilized. For purposes of considering the dose in terms of particle units (pu), also referred to as viral particles, it can be assumed that there are 100 particles/pfu (e.g., $1\times10^{12}$ pfu is equivalent to $1\times10^{14}$ pu). An amount of recombinant virus, recombinant DNA vector or RNA genome sufficient to achieve a tissue concentration of about $10^2$ to about $10^{12}$ particles per ml is preferred, especially of about $10^6$ to about $10^{10}$ particles per ml. In certain applications, multiple daily doses are preferred. Moreover, the number of doses will vary depending on the means of delivery and the particular recombinant virus, recombinant DNA vector or RNA genome administered.

Further provided by the present invention is a hybridoma cell line that produces a monoclonal antibody that is specific for an above-described isolated or purified polypeptide molecule. Methods of making hybridomas are known in the art (see, e.g., Harlow et al., *Antibodies: A Laboratory Manual*, Cold Spring Harbor Laboratory Press, Cold Spring Harbor, N.Y. (1988); Harlow et al., *Using Antibodies: A Laboratory Manual*, Cold Spring Harbor Laboratory Press, Cold Spring Harbor, N.Y. (1999)). Thus, the present invention also provides the monoclonal antibody produced by the hybridoma cell line. Similarly, the present invention provides a polyclonal antiserum raised against an above-described isolated or purified polypeptide molecule. Methods of raising polyclonal antiserum against a polypeptide molecule are also known in the art (see, e.g., Harlow et al. (1988), supra; Harlow et al. (1999), supra).

BRIEF DESCRIPTION OF THE FIGURES

FIG. 1A shows the nucleic-acid and the derived protein sequence of the channel from sea urchin *Strongylocentrotus purpuratus* (SPHI channel).

FIG. 1B shows the S4 motif of said channel protein, as compared with other known channel sequences;

FIG. 1C shows the pore motif of said sequence as compared with other sequences of other channels;

FIG. 2A shows the inward current having a complex waveform, which is triggered by the hyperpolarizing voltage steps from a holding voltage of +10 mV to more negative test values;

FIG. 2B shows the equilibrium current/voltage (I/V) relationship determined at the end of a hyperpolarizing voltage pulse;

FIG. 2E shows that the time course of the "tail" currents depends on the time of the change in voltage;

FIG. 2F shows the voltage dependence of the relative probability that the channel is open, $P_o$, which was determined from the amplitude of tail currents at +10 mV, similar to those illustrated in FIG. 2A;

FIG. 4E shows the ion selectivity of SPIH channels on inside-out patches, in the case of which 100 mM of the bath $K^+$ were replaced by corresponding concentrations of $Rb^+$, $Na^+$, $Li^+$, or $Cs^+$;

FIG. 4F shows the I/V relationship under the various ionic conditions shown in part E;

FIG. 4H shows the I/V relationship of the currents from part G at different $K^+$ concentrations;

FIG. 5A shows a Northern Blot of the channel messenger RNA with a major transcript of about 3.3 kb and a minor transcript of 2.9 kb;

FIG. 5B is a light-microscopic photograph of sperms from *S. purpuratus* (right picture) and the corresponding immunohistochemical staining with an antibody which specifically recognizes the SPIH channel (left picture).

FIG. 5C shows a corresponding Western Blot analysis.

A typical representative of an ion channel protein according to the invention is the channel from sea urchin (SPIH). The channel activity of HEK 293 cells, which had been transfected with the pcSPHI construct (FIG. 6), was examined with the help of the patch-clamp method in the whole-cell configuration. Hyperpolarizing voltage steps showed an inward current with a complex waveform (cf. FIG. 2A). A fast current component that was not time-resolved was followed by a time-dependent current that developed with a delay and, after the maximum had been reached, decreased into smaller amplitudes when the test voltage was $V_m \leqq -30$ mV (FIG. 2A). After $V_m$ had been set back to +10 mV, "tail" currents developed that also showed a complex time course. The steady-state relationship between current/voltage (I/V), at the end of the hyperpolarizing voltage pulse (arrow in FIG. 2A), showed a strong inward rectification (FIG. 2B). The "instantaneous" I/V relationship was determined from the amplitude of the tail currents using a different protocol for the voltage steps (FIG. 2C). The "instantaneous" I/V relationship was slightly outwardly rectifying with a reversal voltage, $V_{rev}$, of −30 mV (FIG. 2D). The I/V relationship became approximately linear at higher $[K^+]_o$ because the inward sodium current was significantly amplified by $[K^+]_o$ (see FIG. 4H). The conclusion can be drawn that the currents are strongly inwardly rectifying because the SPIH channel at positive voltages is either closed or inactivated. The voltage dependence of the open probability, Po (FIG. 2F), was determined from the amplitude of the tail currents at +10 mV (FIG. 2A). The voltage, $V_{1/2}$, at which a half-maximal current was observed, was at −26.1 mV (7 experiments). Thus the SPIH channel is inactive at voltages ≧+10 mV and is opened by hyperpolarization. This voltage dependence reminds of hyperpolarization-activated currents ($I_h$) which occur in different cells (DiFrancesco, 1990, 1993; Pape, 1996). Because of its unusual properties, the $I_h$ has also been designated as a "queer or "funny" current (Iq and If). The channel according to the invention is (1) activated at hyperpolarizing voltages; (2) directly modulated by cyclic nucleotides; (3) blocked by millimolar concentrations of extracellular Cs2+, (4) it is cation-selective at a $P_{Na}/P_K$ of ~0.2 to 0.4; and (5) the inward sodium currents are sensitive to $[K^+]_o$. The following experiments demonstrate that said features are also found in the heterologously expressed SPIH channel.

With 1 mM cAMP in the pipette solution, hyperpolarization produced large currents which developed with a delay and slowly reached a steady state (FIG. 3A).The sigmoidal time course of the current (see FIG. 3A, box) is characteristic of the time course of vertebrate $I_h$ currents. 1 mM cGMP in the pipette also changed the SPIH-induced currents. The voltage dependence of $P_o$ was determined with the help of whole-cell tail currents (FIG. 3B). A fit to the Boltzmann equation yielded $V_{1/2}$=−50.8 mV. The dialysis of the cell with the pipette solution took several minutes; thus transient effects of cAMP might impair the test. A technique was therefore employed using the rapid photorelease of cAMP or cGMP from "caged" derivatives (cf. Adams and Tsien, 1993; Hagen et al., 1996). The cells were dialyzed with 100 pm "caged" cAMP and the SPIH channels were activated by changing the $V_m$ from +10 mV to −70 mV; a short flash of UV light then effected a rapid increase in the amplitude of the SPIH-induced inward current (FIG. 3C). The hyperpolarization-activated currents before the flash resembled control currents (FIG. 3C, trace 1), while amplitude and time course of the currents after the UV flash (FIG. 3C, trace 2) were similar to those recorded in the presence of cAMP (FIG. 3E). With 100 μM "caged" cGMP in the pipette, UV flashes of similar duration and similar intensity did not change the SPIH-induced currents. A binding motif for cyclic nucleotides suggests that cAMP could directly enhance the channel activity without the participation of a phosphorylation mechanism. To verify this hypothesis the SPIH currents were measured on excised membrane patches without (FIG. 3D) and with cAMP (FIG. 3E). cAMP (1 mM) enhanced the amplitudes of the voltage-activated currents by up to 20-fold. The increase in current by cAMP was reversible and did not require $Mg^{2+}$/ATP. The superfusion of the excised membrane patches with solutions containing different cAMP concentrations enhanced the SPIH currents in a dose-dependent way. The dependence of the current on the cAMP concentration can be described by a simple binding isotherm with a $K_{1/2}$ of 0.74 uM and a Hill coefficient which does not significantly differ from one (FIG. 3F). In the separated membrane patches, $V_{1/2}$ in the presence of cAMP was about 35 mV more negative than $V_{1/2}$ measured in the whole-cell configuration (FIG. 3B). This observation might suggest that an endogenous factor provided by the HEK293 cell also determines $V_{1/2}$. cGMP concentrations of up to 1 mM did not change the amplitude of the SPIH currents. The conclusion can be drawn from this experiment that cAMP, but not cGMP, can modulate the SPIH channel activity. Thus, in contrast to CNG channels (Finn et al., 1996) SPIH is under the double control of voltage and cAMP. Blockage of the SPIH channels by extracellular $Cs^+$ was examined on "outside-out" membranes with the voltage protocol of FIG. 2C. $Cs^+$ blocked the SPIH channel in a concentration- and voltage-dependent manner. In the presence of 10 mM $Cs^+$ the inward currents disappeared completely, whereas outward tail currents were still present (cf. FIGS. 4A and 4B). The I/V relationship in the presence of from 0 to 10 mM $Cs^+$ is shown in FIG. 4C. The standardized current $I/I_{max}$ (at −70 mV) was plotted against $[Cs^+]$ (FIG. 4D). The data were fitted with an inhibitory constant $K_i$ of 245 μM and a Hill coefficient of n=1.2. The ion selectivity of the SPIH channel was determined with inside-out membranes. The bath solutions always contained 0.1 mM cAMP to increase the amplitude of the currents. 100 mM K'r in the bath were replaced by $Rb^+$, $Na^+$, $Li^+$ or $Cs^+$ (FIG. 4E). The permeability ratios $P_K:P_{Rb}:P_{Na}:P_{Li}:P_{Cs}$ were calculated as 1:0.7:0.26:0.15:0.06. The ion selectivity of SPIH concurs well with the ion selectivity of various vertebrate $I_h$ channels (Pape, 1996; Wollmuth and Hille, 1992). When the extracellular medium only contained $Na^+$, the inward currents were eliminated almost entirely, whereas the amplitudes of the outward currents did not change significantly (FIG. 4G). Elevation of $[K^+]_o$ to 5 and 20 mM dramatically increased the inward currents. These results demonstrate that the SPIH channel conducts little, if any, sodium in the absence of potassium ions.

Figure 1D:
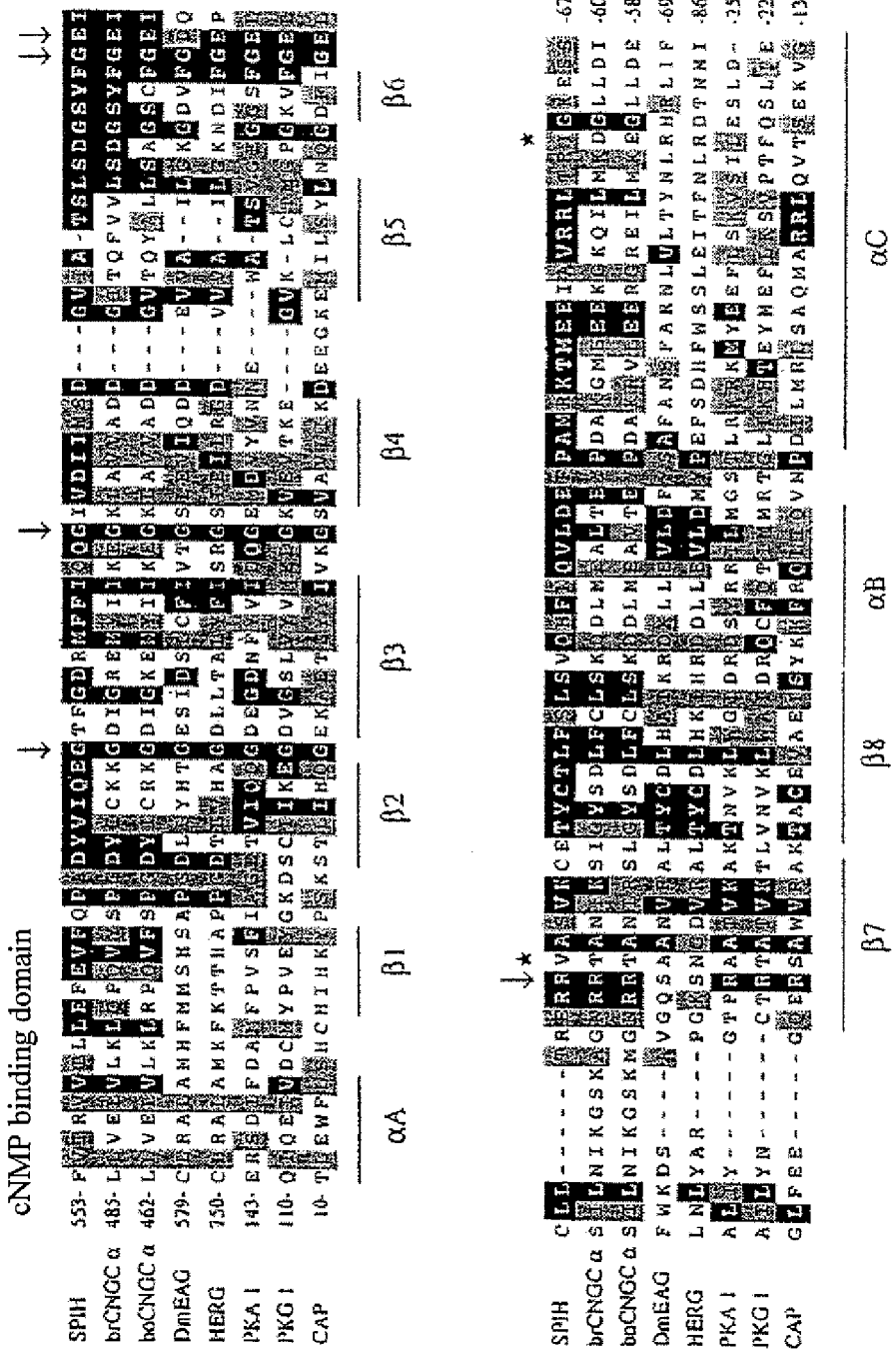
FIG. 1D shows the cNMP-binding domain of the cDNA of the $I_h$ ion channel as compared with other sequences of ion channels.

The expression of messenger RNA of the channel protein was analyzed by means of Northern Blots. A major transcript of around 3.3 kb and a minor transcript of 2.9 kb were detected in poly(A)$^+$RNA of male, but not female, gonads (FIG. 5A). The size of the transcripts concurs well with the size of the cloned cDNA (3 kb). The SPIH-specific probe did not hybridize with poly(A)$^+$RNA isolated from the intestine of sea urchin (FIG. 5A). The exclusive expression of SPIH mRNA in male gonads suggests that the channel is expressed in sperms. This hypothesis was tested with purified antibodies FPc44K and FPc45K directed against a fusion protein of the C-terminal domain of the channel polypeptide (residues 662-767). The antibodies were used for Western Blot analyses (FIG. 5C) and immunocytochemistry (FIG. 5B). Both antibodies recognized a main band of $M_r$~92K in Western Blots of flagellar membranes which had been purified from sea urchin sperm (FIG. 5C, lane 3). Membranes which had been purified from the sperm head were not recognized by the antibodies (FIG. 5C, lane 5). This result was confirmed by immunocytochemistry with individual sperms. The antibody FPc45K almost exclusively stained the sperm flagellum (FIG. 5B); the weak staining of some head structures presumably represents unspecific cross reactivity of the antibody. A band of $M_r$~88K was observed in Western Blots of membranes of transfected HEK293 cells (FIG. 5C, lane 2). The $M_r$ of the channel polypeptide, expressed in HEK293 cells, is almost identical with the $M_r$ value as is to be expected of the derived amino acid sequence (87.9K). In membranes of non-transfected HEK293 cells, no 88K polypeptide was detected by the antibody (FIG. 5C, lane 1). The treatment of flagellar membranes with alkaline phosphatase lowered the $M_r$ of the native polypeptide from ~92 K to 88K. Since native and heterologously expressed polypeptides were of a similar size, the cloned cDNA carries the complete coding sequence of SPIH.

The small decrease in $M_r$ under dephosphorylating conditions demonstrates that the native polypeptide in phosphorylated form is present with a slightly reduced electrophoretic mobility. In most dephosphorylation experiments the shift from 92K to 88K was not complete, and at least two intermediate bands were observed. This result suggests that the channel polypeptide should be phosphorylated several times. The SPIH sequence carries sequence motifs for the phosphorylation by PKA, PKG, PKC and tyrosine kinase (see FIG. 1A). The electrophysiological properties unequivocally identify SPIH as a member of the $I_h$ channel family. However, we also noticed characteristic differences between SPIH and vertebrate $I_h$ channels. First, in the absence of cAMP the SPIH current is transient, whereas in the presence of cAMP the time course is similar to that in vertebrate $I_h$ channels. Second, the large augmentation of the SPIH current by cAMP primarily arises from an increase in the maximum current while cAMP modulates the cardiac $I_h$ channel such that $V_{1/2}$ is shifted towards more positive values (Di Francesco, 1993) without influencing the maximum amplitudes (see, however, Ingram and Williams, 1996; Accili et al., 1997). Finally, the cardiac $I_h$ is also modulated by micromolar cGMP concentrations (Di-Francesco and Tortora, 1991), whereas SPIH does not exhibit said effect. The SPIH channel is very similar to both the voltage-controlled $K^+$ channels and the CNG cation channels. That is why the $I_h$ channels form a class of their own within the superfamily of the voltage-controlled channels. SPIH has a characteristic motif of a voltage sensor (S4) like the $K^+$, $Na^+$ and $Ca^{2+}$ channels that are opened by depolarization. Although there is no a priori reason to rule out the S4 motif as a voltage sensor in a hyperpolarization-activated channel, the mechanism of an activation as in HERG-$K^+$ channels (Trudeau et al., 1995; Smith et al., 1996) is more likely. It has been demonstrated with respect to the strong inward rectification of HERG that it is the result of the inactivation which closes the channels at positive voltages, but the channels recover rapidly from the inactivation at negative voltages. In HERG channels the inactivation is much faster than the activation and is therefore not visible kinetically (Smith et al., 1996). Together with the CNG channels SPIH possesses a cyclic nucleotide-binding region, and its properties are modulated by cAMP. cAMP probably intensifies the SPIH activity by binding to the highly conserved cyclic nucleotide-binding region. In CNG channels, it has been demonstrated with respect to the high selectivity for cGMP that said selectivity is accompanied by a Thr residue (T363 in the a-subunit of the rod photoreceptor; Altenhofen et al., 1991) and an Asp residue (D604 in rCNGa; Varnum et al., 1995). The SPIH has Val and Ile residues at the corresponding positions; it is presumed that these positions also control the ligand selectivity in SPIH. The physiological importance of the $I_h$ channels in flagellar membranes of sperm could be explained as follows: the stimulation of S. purpuratus sperm with the chemotactic peptide "speract" causes a hyperpolarization (Lee and Garbers, 1986; Garbers, 1989), of which it is assumed that it is due to the opening of a $K^+$ channel (Babcock et al., 1992). At higher peptide concentrations the hyperpolarization is followed by a depolarization (Babcock et al, 1992). Two (or more) ion channel types with different selectivity and pharmacology could contribute to the "speract"-induced depolarization (see Darszon et al, 1996). One of said channels has a weak $K^+$ selectivity ($P_{Na}/P_K=0.2$) and an extremely low $P_o$ (at $V_m=0$ mV) which is considerably enhanced by cAMP, but not by cGMP (Labarca et al., 1996). These observations suggest that said channel is actually SPIH. The "speract"-induced hyperpolarization could initiate the SPIH channel activity which then could even be augmented by a simultaneous increase in the cAMP level (Hansbrough et al., 1980) with the help of a voltage-dependent adenylate cyclase (Beltrán et al, 1996). At the given ionic composition of sea water and a PNa/Pk of 0.2 to 0.4 the opening of the SPIH channel and the subsequent $Na^+$ influx could effect the "speract"-induced depolarization. It can also reasonably be assumed that the $I_h$ channels, for instance in cardiac cells or thalamic neurons, take part in the generation of oscillations of the membrane voltage, thereby causing the oscillation of $Ca^{2+}$ in the flagellum (Suarez et al, 1993). The change in $[Ca^{2+}]$, could change the flagellar beating, thereby contributing to the chemotactic response.

EXAMPLES

Methods

Isolation of the cDNA clones

With two degenerated primers (# 1764 and # 1772) a PCR was carried out on single-strand cDNA (from sea urchin gonads, Drosophila melanogaster, bovine retina, olfactory tissue of the rat) or on cDNA libraries (from human thalamus or heart). A 100 µl PCR batch had the following composition: 3-10 ng of first-strand cDNA and about $10^5$ Pfu of the cDNA libraries, respectively, 1.6 ug of the degenerated primer each, 1×PCR buffer, 2 mM dNTP, 1 U PrimeZyme (Biometra). The PCR batch was first denatured at 94° C. for 2 min and then incubated for 45 cycles in the following manner:

denaturation: 94° C., 45 sec hybridization: 48° C., 45 sec polymerization: 72° C., 40 sec The sequences of the degenerated primers are (in 5'→3' direction):

```
                                        SEQ ID NO: 16
#1764:  CTGACTGCAGARGTNTTYCARCCNGGNGA

SEQ ID NO: 17
#1772:  ATCGGAATTCNCCRAARTANGANCCRTC
```

The PCR fragments amplified with the primers # 1764 and # 1772 were radiolabeled and used as probes for screening cDNA libraries under high stringency for the complete cDNAs. The partial clone HHIH (SEQ ID NO: 11) was isolated by low-stringency hybridization. The hybridization conditions were as follows:

|  | high stringency | low stringency |
|---|---|---|
| pre-hybridization | 5 x SSC[(1)], 5 x Denhardt's[(2)], 0.1% SDS, 0.1 mg/ml herring sperm DNA, 1-2 h, 65° C. | 5 x SSC[(1)], 5 x Denhardt's[(2)], 0.1 % SDS, 0.1 mg/ml herring sperm DNA, 1-2 h, 55° C. |
| hybridization | prehybridization solution with 50-100 ng $^{32}$P-labeled DNA (1-$10^6$ cpm/ml), 12-14 h, 65° C. | prehybridization solution with 50-100 ng $^{32}$P-labeled DNA (1 x $10^6$ cpm/ml), 12-14 h, 65° C. |
| washing | 1 x SSC(1), 0.1% SDS 2 × 30 min, 65° C. | 2 x SSC(1), 0.1% SDS 2 × 30 min, 55" C. |

[(1)]1 x SSC 150 mM NaCl, 15 mM Na citrate, pH 7.0
[(2)]1 x Denhardt's Ficoll, polyvinylpyrrolidone, bovine serum albumin (0.2 g/l each)

The positive phages were isolated and the cDNA was converted by "in vivo excision" (in case of λZAPII phages) into pBluescriptSK derivatives. The cDNA was excised with EcoRI from λgt11 phages and subcloned into pBluescriptSK plasmid DNA. The DNA was sequenced with the dideoxy-mediated chain termination technique (Sanger et al., 1997).

Northern and Western Blots

Poly(A)+RNA, isolated from different sea urchin tissues, was analyzed by Northern blotting. Each lane contained about 10 ug poly(A)+RNA. The blot was hybridized with a $^{32}$P-labeled 1074 bp cDNA fragment (nucleotide positions) at 42° C., 5×SSC and 50% formamide. A C-terminal region of the SPIH polypeptide was expressed as a fusion construct with the maltose binding protein. The purified fusion protein was used for producing the polyclonal antibodies FPc44K and FPc45K; the antibodies were purified from rabbit serum by affinity chromatography using the fusion protein. Sperm flagella were separated from the head according to Darszon et al. (1994). Purified flagella and head membranes were homogenized in a solution buffer containing 150 mM NaCl, 1 mM MgCl2, 20 mM Hepes at pH 7.5, 0.1 mM EGTA and 0.5% Triton X-100, followed by a centrifugation at 40,000 rpm for 60 minutes. This process was repeated two times. Transfected HEK293 cells were homogenized in a lysis buffer (10 mM Hepes, 1 mM DTT and 1 mM EDTA at pH 7.4), 5×freeze-dried (in liquid N2) and finally centrifuged at 55,000 rpm for 10 minutes. The membrane pellet was dissolved in the solution buffer. Flagellar membrane proteins were dephosphorylated with a unit of alkaline phosphatase in solution buffer at 30° C. for 30 to 60 min. The membrane proteins were separated by SDS-PAGE, transferred to Immobilon membranes and labeled with the polyclonal antibodies. The immunoreactivity was made visible by the ECL detection kit (Amersham). Immunocytochemistry on an individual sperm was carried out as described above (Weiner 1997).

Electrophysiology cDNA coding the SPIH polypeptide was transiently expressed in HEK293 cells, as described earlier (Baumann et al, 1994). SPIH-controlled currents were recorded with the patch-clamp method in the whole-cell configuration and cell-free membrane patches. The composition of various bath and pipette solutions is indicated in the legends of the figures (see below). The channels were activated by stepping the membrane voltage from +10 mV to various negative voltage values. Leakage currents were subtracted using a P/8 protocol. The voltage dependence of the probability that the channel is open was determined from tail currents at +10 mV. The blockade of the SPIH channel by Cs2+ was analyzed with outside-out membrane patches in the presence of 1 mM cAPM in a pipette solution. The solutions in the bath contained 0.03 to 10 mM CsCl. Relative ion permeabilities were calculated from the respective shift of $V_{rev}$, which was measured on cell-free inside-out membrane patches, when 100 mM K+ in the bath had been replaced by Na+, Li+, Rb+ or Cs+. Experiments with "caged" cAMP or "caged" cGMP were carried out as described earlier (Hagen et al. 1996).

The results of said experiments are now described in more detail.

FIG. 1A shows the nucleic acid sequence and the derived amino acid sequence of the $I_h$ channel of sea urchin (SPIH). Nucleotides are numbered in 5'→3' direction, +1 corresponding to the first nucleotide of the start codon (ATG) of the open reading frame. Nucleotides that are 5'-located from nucleotide +1 are designated by negative figures. The derived amino acid sequence (one-letter code) is indicated under the nucleic acid sequence and is also numbered. The start codon (ATG), the corresponding methionine and the stop codon (TGA; pos. 2302-2304) are printed in bold. Stop codons in the same reading frame before the start codon are underlined. The polyadenylation signal at position 2501-2507 is boxed. The position of the transmembranal segments S1-S6, of the pore-forming region and of the binding site for cyclic nucleotides (cNMP binding site) is marked by bars above the nucleic acid sequence. The limits of said regions are defined by sequence comparison with other voltage-dependent K+ channels, EAG-K+ channels and CNG channels. Consensus sequences for phosphorylation by cAMP/cGMP-dependent kinases are marked by triangles (A). Consensus sequences for phosphorylation by protein kinase C are marked by circles (●) and that by tyrosine kinase by an asterisk (*). The SPIH sequence (SEQ ID NO: 4) codes for a protein of 767 amino acids with a calculated molecular weight of 87,937 Da.

FIG. 1B shows a comparison of the voltage-sensor (S4) motifs of the $I_h$ channel of sea urchin and other channels. Regularly spaced Arg or Lys residues are boxed. Other positively charged residues are in bold. Shaker (Pongs et al., 1988), K+ channel encoded by the Drosophila Shaker gene (SEQ ID NO: 21); DmEAG (Warmke et al, 1997), Drosophila EAG channel (SEQ ID NO: 22); HERG, human EAG-related gene (Warmke and Ganetzky, 1994) (SEQ ID NO: 23); KAT1 (Anderson et al, 1992), K+ channel of Arabidopsis thaliana) (SEQ ID NO: 24); brCNGCa (Kaupp et al, 1989), alpha-subunit of the cyclic nueleotide-controlled channel from bovine rod photoreceptors (SEQ ID NO: 25).

FIG. 1C shows the pore motif of SPIH with the pore motifs of other members of the superfamily of the voltage- and cyclic nueleotide-controlled ion channels: The residues which are identical or similar to the corresponding amino acids in SPIH are highlighted by a black or grey background. The sequences disclosed include (a) the K+ channel encoded by the Drosophila Shaker gene (SEQ ID NO: 26), (b) the Drosophila EAG channel (SEQ ID NO: 27), (c) the human EAG-related gene (SEQ ID NO: 28), (d) the K+ channel of Arabidopsis thaliana (SEQ ID NO: 29), and (e) the alpha-subunit of the cyclic nucleotide-controlled channel from bovine rod photoreceptors (SEQ ID NO: 30).

FIG. 1D shows a sequence comparison of cNMP binding domains. boCNGCalpha, the alpha-subunit of the CNG channel of bovine olfactory neurons (Ludwig et al., 1990) (SEQ ID NO: 31); brCNGCa (Kaupp et al, 1989), alpha-subunit of the cyclic nucleotide-controlled channel from bovine rod photoreceptors (SEQ ID NO: 32), the Drosophila EAG channel (SEQ ID NO: 33); the human EAG-related gene (SEQ ID NO: 34); PKA1, the cAMP binding site 1 of the protein kinase A (Titant et al, 1984) (SEQ ID NO: 35); the cGMP binding site 1 of the protein kinase G (Takio et al, 1984) (SEQ ID NO: 36); CAP, the catabolite activator protein (Aiba et aL, 1982) (SEQ ID NO: 37). Residues that are highly conserved in cyclic nucleotide-binding motifs are indicated by arrows; residues that determine the ligand selectivity in brCNGCa are indicated by an asterisk. Secondary-structure predictions derived from the cAMP binding domain of CAP are shown as bars below the sequence.

FIG. 2 shows the electrophysiological characterization of the SPIH channel.

FIG. 2A shows the current, which was recorded by transfected HEK293 cells in the whole-cell configuration. The current was activated by stepping the voltage from a holding value at +10 mV to various test values of −100 mV to +10 mV in increments of 10 mV. Tail currents were recorded by stepping the voltage of the test value back to +10 mV. The HEK293 cells were flushed with a bath solution containing the following (mM):

135 NaCl, 5 KCl, 1.8 CaCl2, 2.8 MgCl2 and 5 Hepes-NaOH at pH 7.4; the pipette solution contained the following substances (mM): 126 KCl, 10 Hepes-KOH, 10 EGTA at pH 7.4.

In FIG. 2B, there is plotted the voltage-current (I/V) relationship measured under equilibrium conditions at the time indicated by the arrowhead in FIG. 2A.

Figure 2C:
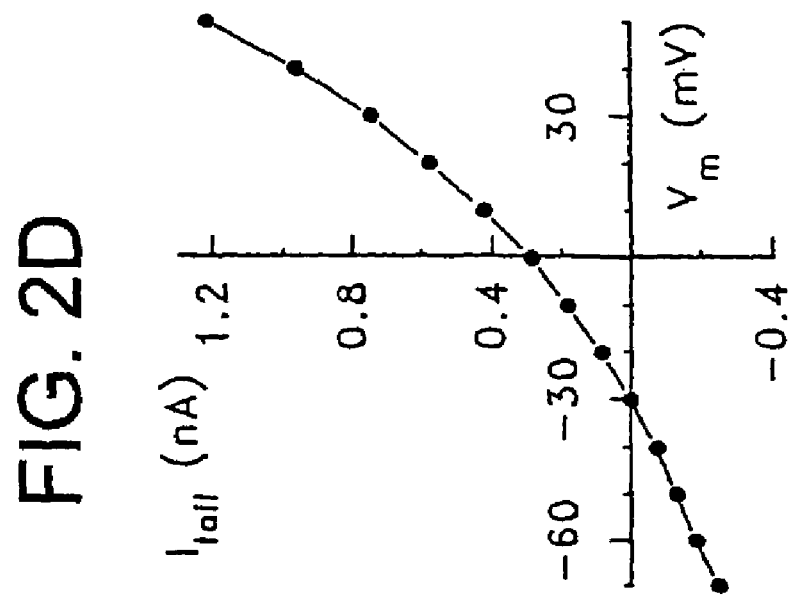
FIG. 2C shows the measuring protocol for the determination of the "instantaneous" I/V relationship from the amplitude of the tail currents.

FIG. 2C shows the measurement protocol with which the "instantaneous" I/V relationship was determined; the voltage was first stepped from a holding value of 0 mV to −70 mV, followed by steps to test values in the range of from +50 mV to −70 mV in 10 mV increments.

Figure 2D:
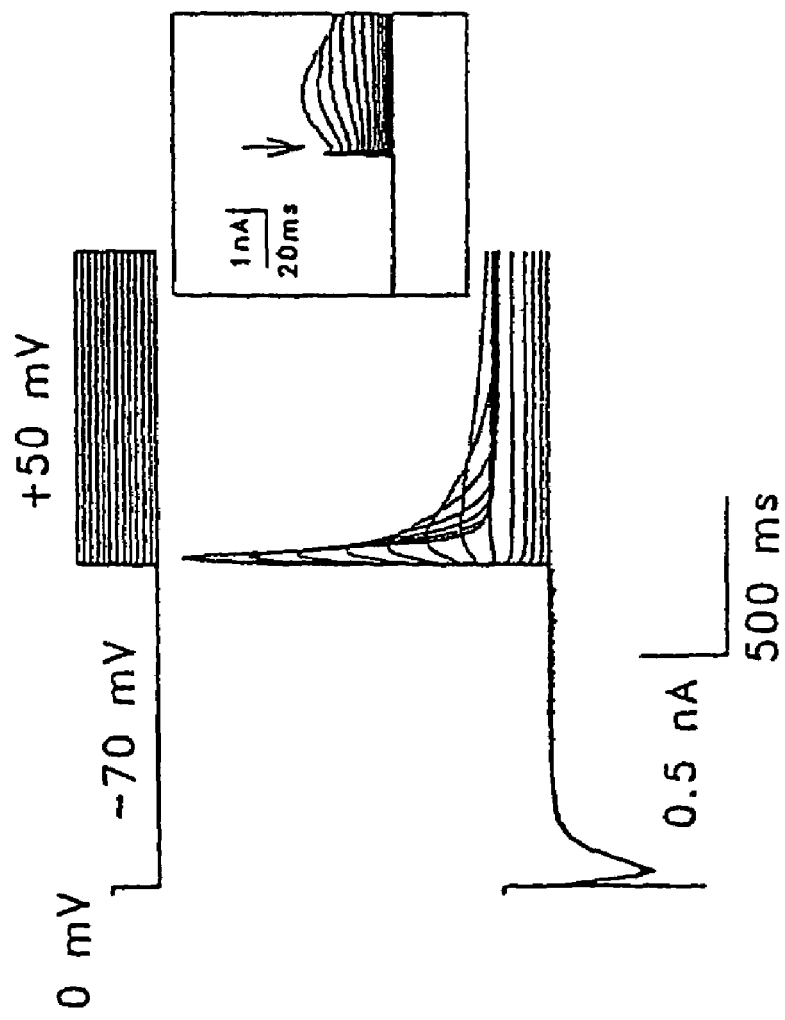
FIG. 2D shows the "instantaneous" I/V relationship which is slightly outwardly rectifying, at a reversal voltage $V_{rev}$ of −30 mV.

FIG. 2D then shows the plot of the "instantaneous" I/V relationship measured at the time indicated by the arrow in FIG. 2C (inset).

FIG. 2E shows that the time course of the "tail" currents depends on the time at which the voltage is reset to +30 mV.

FIG. 2F shows the voltage dependence of the relative open probability, Po, of the channel. The tail current amplitudes (arrow in part a) were normalized to the maximum current. The midpoint voltage, $V_{1/2}$, was −26.1 mV. The effective charge amount, Q, which is flowing during channel switching, is 3.5 elementary charges. It was achieved from a fit of the Boltzmann function to the data: Mean of 7 experiments.

FIG. 3 indicates the modulation of SPIH channels by cyclic nucleotides.

Figure 3B:
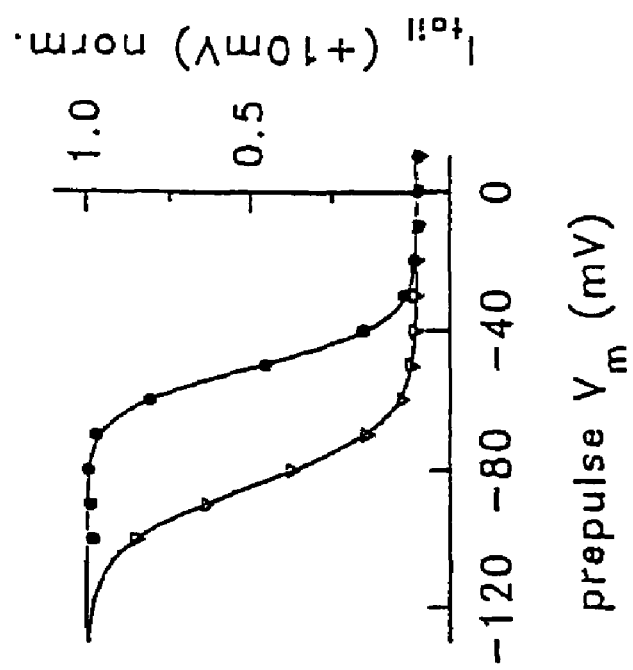
FIG. 3B shows the voltage dependence of $P_o$, determined from normalized whole-cell "tail" currents and "tail" currents of inside-out patches.
Figure 3A:
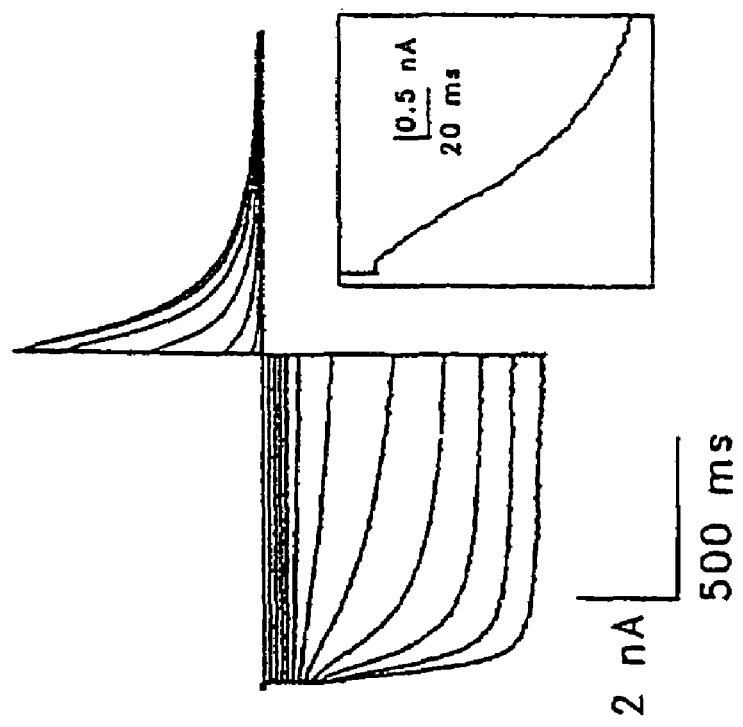
FIG. 3A shows the induction of large whole-cell currents by hyperpolarization in the presence of 1 mM cAMP, which currents developed with a delay and slowly reached an equilibrium.

FIG. 3A shows the whole-cell SPIN current in the presence of 1 mM cAMP. The voltage-step protocol is the same as in FIG. 2A. The bath contained (mM): 135 NaCl, 5 KCl, 1.8 CaCl2, 2.8 MgCl2 and 5 Hepes-NaOH at pH 7.4; the pipette solution contained (mM): 126 KCl, 10 Hepes-KOH, 10 EGTA at pH 7.4, and 1 mM cAMP. The inset shows a magnification by way of which the sigmoidal time course can be seen particularly well.

FIG. 3B shows the voltage dependence of the relative Po, derived from normalized whole-cell tail currents at +10 mV (●) and of tail currents recorded by inside-out patches (▲). A continuous line represents a fit of the Boltzmann equation to the data. $V_{1/2}$ for the whole-cell currents of part A was −50.8 mV and for the inside-out-patch currents of part E it was −84.7 mV; the Q values were 3.8 and 2.7, respectively.

Figure 3D:
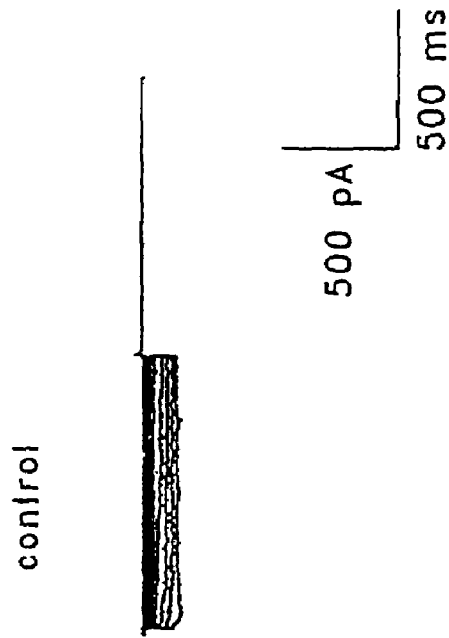
FIG. 3D shows SPIH currents of cell-free membrane pieces without cAMP.
Figure 3C:
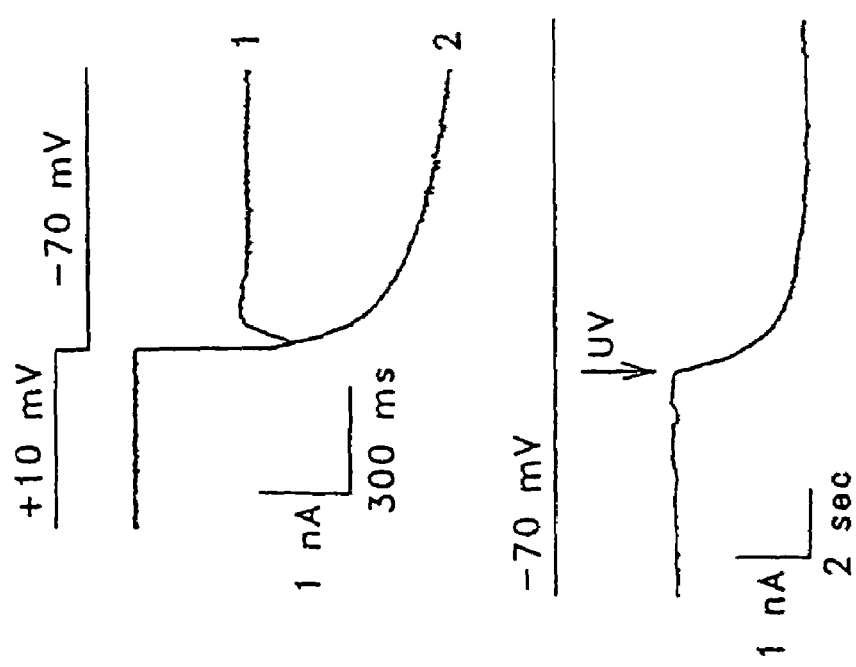
FIG. 3C shows the rapid rise in amplitude of the inward current after short UV exposure.

FIG. 3C shows the modulation of whole-cell SPIH currents by the photolysis of "caged" cAMP. The pipette solution contained 100 uM "caged" cAMP. The SPIH current was activated by voltage jumps from +10 mV to −70 mV before the UV flash was induced (trace 1) and after three consecutive UV flashes (trace 2). The time course of the flash-induced increase in current at −70 mV is shown below.

FIGS. 3D and E show voltage-activated SPIH currents in inside-out membrane patches without cAMP (D) and in the presence of 1 mM cAMP (E) in the bath. The voltage step protocol was carried out in the way as shown in FIG. 2A. The pipettes and bath solutions contained (mM): 126 KCl, 10 Hepes-KOH, 10 EGTA at pH 7.4 and 1 mM cAMP (bath).

Figure 3F:
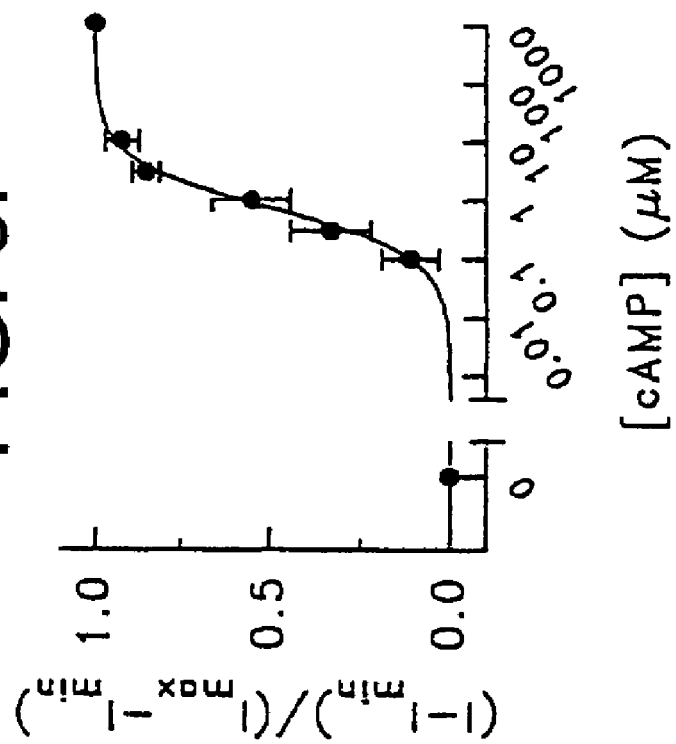
FIG. 3F shows the dependence of the current on the cAMP concentration which can be described by a simple binding isotherm with $K_{1/2}$ of 0.74 µM and a Hill coefficient which does not clearly differ from one.
Figure 3E:
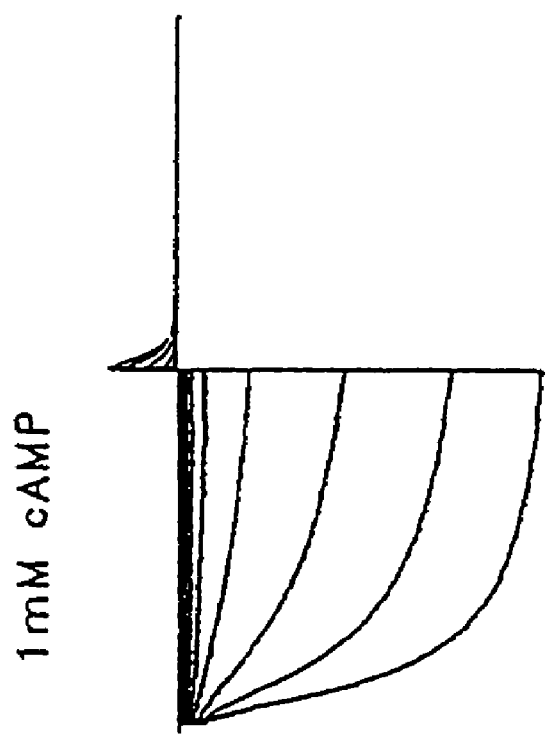
FIG. 3E shows the same as FIG. 3D, but with cAMP.

FIG. 3F discloses the dependence of the SPIH current amplitude on the cAMP concentration; the cAMP concentrations were as follows (μM): 0.1; 0.3; 1; 3; 10 and 1000. A continuous line shows a fit of the Hill equation to the data; $K_{1/2}$=0.74 uM; n=1.05; mean of 10 experiments.

FIG. 4 shows several pharmacological properties of the SPIH channel.

Figure 4A:
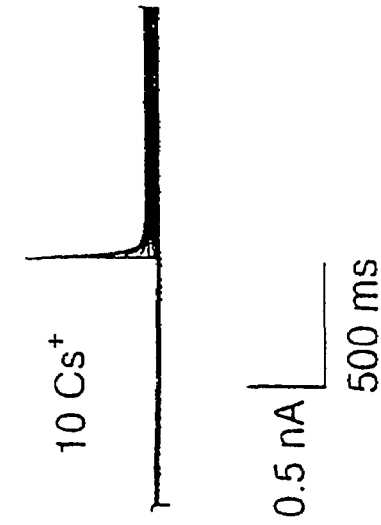
FIG. 4A shows the blockade of the SPIH channels by $Cs^+$ (control).
Figure 4B:
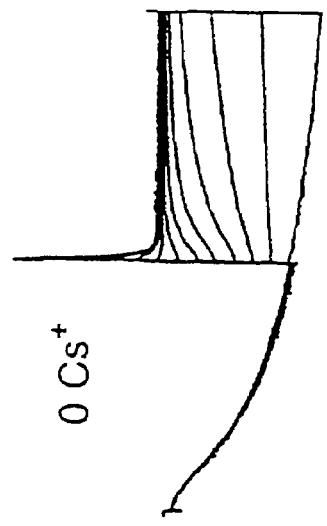
FIG. 4B shows the blockade of the SPIH channels by 10 mM $Cs^+$.
Figure 4C:
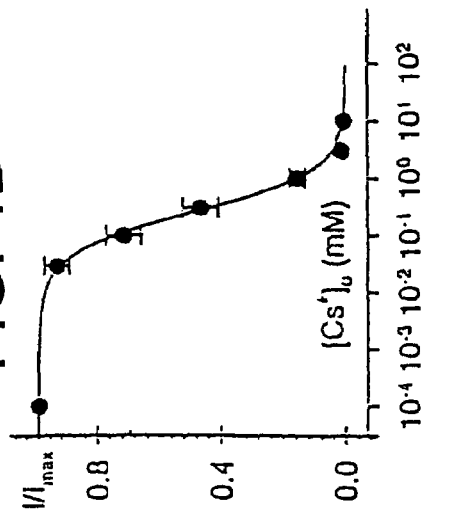
FIG. 4C shows the I/V relationship in the presence of 0 to 10 mM $Cs^+$.

FIGS. 4A and B show voltage-activated SPIH currents, recorded by outside-out membrane patches without (A) and with 10 mM $Cs^+$ (B) in the bath; the pipette solution contained the following (mM): 124 KCl, 10 Hepes-KOH, 10 EGTA at pH 7.4 and 1 mM cAMP; the bath solution contained (mM): 126 KCl, 10 Hepes-KOH, 10 EGTA at pH 7.4 and the illustrated concentrations of CsCl.

FIG. 4C shows again the I/V relationship in the presence of 0 to 10 mM $Cs^+$ in the bath.

Figure 4D:
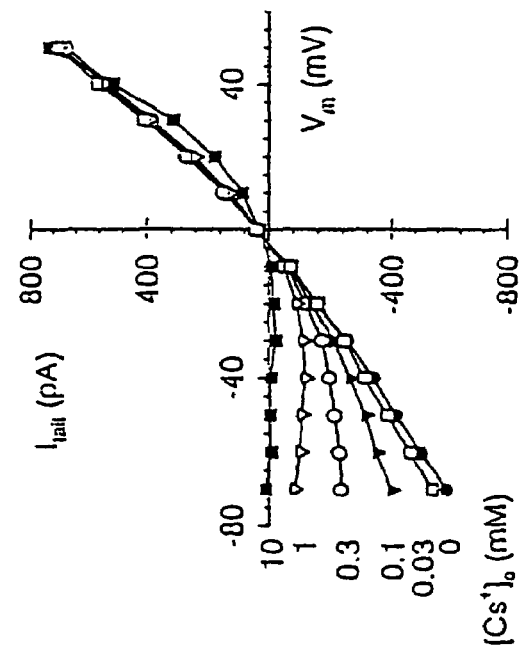
FIG. 4D shows a plot of standardized current $I/I_{max}$ (at −70 mV) against $Cs^+$

FIG. 4D discloses the dependence of the normalized current at −70 mV on [$Cs^+$]. The continuous line shows a fit of the Hill equation to said data; $K_i$=245 μM, Hill coefficient 1.2 (mean of 1-6 experiments).

FIG. 4E shows the ion selectivity of the SPIH channel. $V_{rev}$ was determined on inside-out patches by stepping the holding voltage (−70 mV) to test values between −30 mV and +30 mV in 5 mV increments. The pipette solution contained the following (mM): 150 KCl, 10 Hepes-NMDG, 10 EGTA at pH 7.4; the bath solution was composed as follows (mM):

50 KCl, 100 XCl, 10 Hepes-NMDG, 10 EGTA at pH 7.4 and 0.1 cAMP.

FIG. 4F shows the I/V relationship of the currents shown in part E. $V_{rev}$ was 16.9 mV (Na+, 20.6 mV ($Li^+$, 5.6 mV ($Rb^+$), and 24.6 mV ($Cs^+$; mean of 3 to 10 experiments. The relative ion permeabilities PX/?K were calculated according to the equation $Px/PK=\{[K^+]_o-[K^+]_j \exp(zF\ V_{rev}/RT)\}/[X+]$, $\exp(zF\ V_{rev}/RT)$.

Figure 4G:
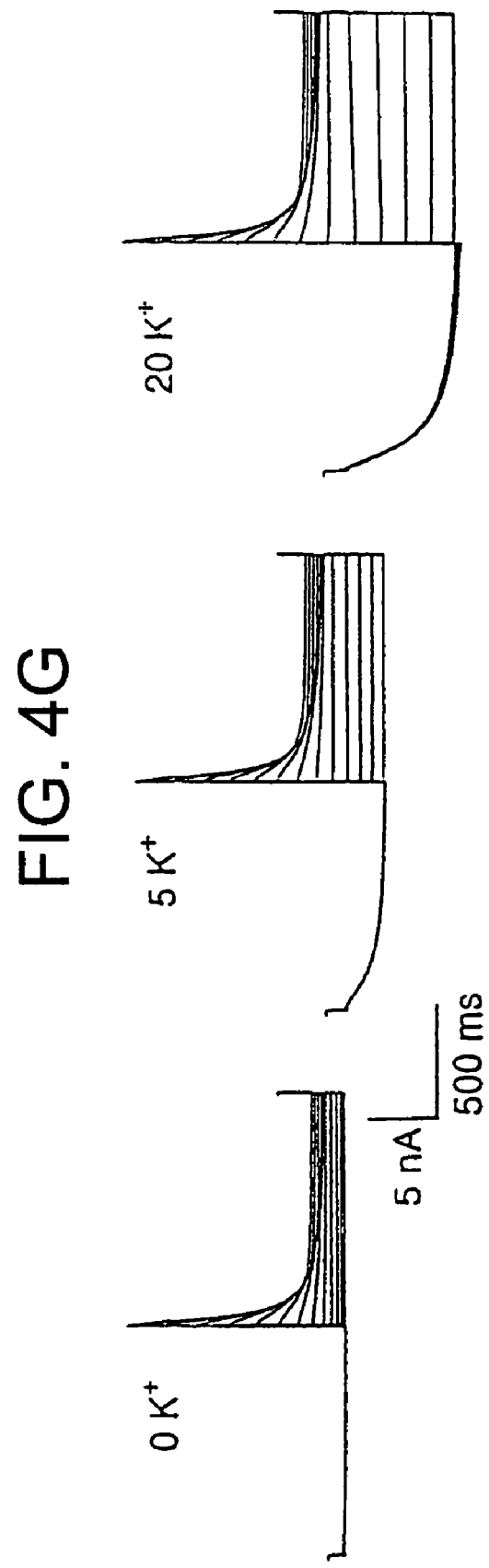
FIG. 4G shows that the inward currents were interrupted almost entirely, whereas the amplitudes of the outward currents did not change when the extracellular medium just contained Na"*"
Figure 6:
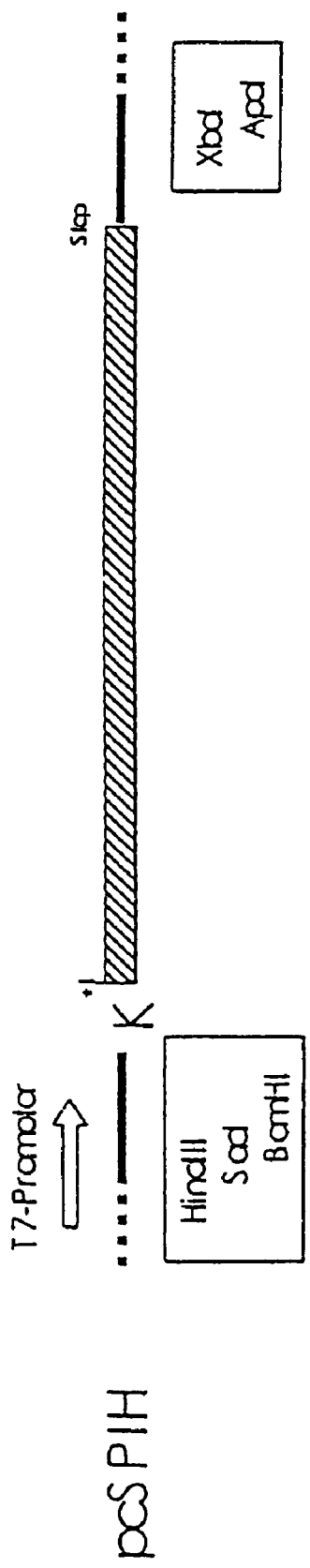
FIG. 6 is a schematic illustration showing the pc SPIH construct that was used for the heterologous expression of SPIH in HEK 293 cells. The cDNA region is illustrated as a hatched bar; the adjoining regions of the plasmid vector (pcDNA I) as bold lines. The orientation of the cDNA in the plasmid vector can be inferred from the position of the promoter for the T7 polymerase and the restriction sites in the multiple cloning region. The inserted Kozak sequence is designated by K.

FIG. 4G shows the $K^+$ dependence of whole-cell inward $Na^+$ currents in the presence of 0.5 mM and 20 mM $K^+$ in extracellular medium.

FIG. 4H shows the "instantaneous" I/V relationship in the presence of 0, 1, 3, 5, 10, and 20 mM K" in the bath.

The pipette solution was the same as in part B, the bath solution as in FIG. 1A with the indicated $K^+$ concentrations; the ion intensities were adjusted to the same value by the respective NMDG concentrations.

FIG. 5 shows the expression pattern of SPIH.

FIG. 5A is a Northern Blot analysis of the tissue distribution of SPIH transcripts in mRNA of male gonads (lane 1), female gonads (lane 2) and intestinal cells (lane 3); 10 μl poly(A)+RNA each.

FIG. 5B is a Western Blot analysis of membranes of mock-transfected HEK293 cells (lane 1; 2.5 ug protein), HEK293 cells which were transfected with SPIH cDNA (lane 2; 2.5 ug protein), purified flagella from sperm of *S. purpuratus* (lane 3; 6 ug protein), dephosphorylated flagellar membranes (lane 4; 6 ug protein) and sperm heads (lane 5; 15 ug protein).

Reference table of the DNA sequences described in the text by SEQ ID numbers

| SEQ ID NO: | DNA sequence |
|---|---|
| 1 | Partial sequence of the $I_h$ channel from human thalamus tissue |
| 2 | partial sequence of an $I_h$ channel from olfactory rat tissue |
| 3 | partial sequence of an $I_h$ channel from retinal bovine tissue |
| 4 | complete sequence of the $I_h$ channel from sea urchin sperm |
| 5 | complete sequence of the $I_h$ channel from *Drosophila melanogaster* |
| 6 | partial sequence of an $I_h$ channel from retinal bovine tissue |
| 7 | partial sequence of an $I_h$ channel from retinal bovine tissue |
| 8 | partial sequence of an $I_h$ channel from olfactory rat tissue |
| 9 | partial sequence of an $I_h$ channel from olfactory rat tissue |
| 10 | partial sequence of an $I_h$ channel from human thalamus tissue |
| 11 | partial sequence of an $I_h$ channel from human heart tissue |
| 12 | complete sequence of an $I_h$ channel from retinal bovine tissue |
| 13 | partial sequence of an $I_h$ channel from olfactory rat tissue |
| 14 | partial sequence of an $I_h$ channel from olfactory rat tissue |
| 15 | complete sequence of an $I_h$ channel from human heart tissue |

Literature

Accili, E. A., Redaelli, G. and DiFrancesco, D.: Differential control of the hyperpolarization-activated current (i) by cAMP gating and phosphatase inhibition in rabbit sino-atrial node myocytes. J. Physiol. 500 (1997) 643-651.

Adams, S. R. and Tsien, R. Y.: Controlling cell chemistry with caged compounds. Annu. Rev. Physiol. 55 (1993) 755-784.

Aiba, H., Fujimoto, S. and Ozaki, N.: Molecular cloning and nucleotide sequencing of the gene for E. coli/cAMP receptor protein. Nucleic Acids Res. 10 (1982) 1345-1361.

Altenhofen, W., Ludwig, J., Eismann, E., Kraus, W., Bonigk, W. and Kaupp, U. B.: Control of ligand specificity in cyclic nucleotide-gated channels from rod photoreceptors and olfactory epithelium. Proc. Natl. Acad. Sci. USA 88 (1991) 9868-9872.

Anderson, J. A., Huprikar, S. S., Kochian, L V., Lucas, W. J. and Gaber, R. F.: Functional expression of a probable *Arabidopsis thaliana* potassium channel in *Saccharomyces cerevisiae*. Proc. Natl. Acad. Sci. USA 89 (1992) 3736-3740.

Araki, T., Ito, M. and Oshima, T.: Potential changes produced by application of current steps in motoneurones. Nature 191 (1962) 1104-1105.

Attwell, D. and Wilson, M.: Behavior of the rod network in the tiger salamander retina mediated by membrane properties of individual rods. J. Physiol. 309 (1980) 287-315.

Babcock, D. F., Bosma, M. M., Battaglia, D. E. and Darszon, A.: Early persistent activation of sperm K channels by the egg peptide speract. Proc. Natl. Acad. Sci. USA 89(1992)6001-6005.

Bader, C. R., MacLeish, P. R. and Schwartz, E. A.; A voltage-clamp study of the light response in solitary rods of the tiger salamander. J. Physiol. 296 (1979) 1-26.

Bader, C. R., Bertrand, D. and Schwartz, E. A.: Voltage-activated and calcium-activated currents studied in solitary rod inner segments from the salamander retina. J. Physiol. 331 (1982)253-284.

Baumann, A., Frings, S., Godde, M., Seifert, R. and Kaupp, U. B.: Primary structure and functional expression of a *Drosophila* cyclic nucleotide-gated channel present in eyes and antennae. EMBO J. 13 (1994) 5040-5050.

Beltran, C., Zapata, O. and Darszon, A.: Membrane potential regulates sea urchin sperm adenylylcyclase. Biochemistry 35 (1996) 7591-7598.

Brown, H. F. and DiFrancesco, D.: Voltage clamp investigations of current underlying pacemaker activity in rabbit-sino-atrial note. J. Physiol. 308 (1980) 221-251.

Brown, H. F., DiFrancesco, D. and Noble, S. J.: How does adrenaline accelerate the heart? Nature 280 (1979) 235-236.

Darszon, A., Labarca, P., Beltran, C., Garcfa-Soto, J. and Lievano, A.: Sea urchin sperm: An ion channel reconstitution study case. Methods: A Companion to Methods in Enzymology 6 (1994) 37-50.

Darszon, A., Lievano, A. and Beltran, C.: Ion channels: Key elements in gamete signaling. In Current Topics in Developmental Biology, Vol. 44. Academic Press, San Diego, 1996, pp. 117-167.

Dayhoff, M. O., Schwartz, R. M., Orcutt, B. C. (1978) in: Atlas of protein sequence and structure, Band 5, Suppl. 3, Hrsg.: Dayhoff, M. O., National Biomedical Research Foundation, Silver Spring, Md., S. 345-352.

DiFrancesco, D.: A new interpretation of the pace-maker current in calf Purkinje fibres. J. Physiol. 314 (1981 a) 359-376.

DiFrancesco, D.: A study of the ionic nature of the pace-maker current in calf Purkinje fibres. J. Physiol. 314 (1981b) 277-293.

DiFrancesco, D.: The hyperpolarization-activated current, i, and cardiac pacemaking. In Rosen, M. R., Janse, M. J. and Wit, A. L (Eds.), Cardiac Electrophysiology: a Textbook. Futura, New York, 1990, pp. 117-132.

DiFrancesco, D.: Pacemaker mechanisms in cardiac tissue. Annu. Rev. Physiol. 55 (1993)455-472.

DiFrancesco, D. and Tortora, P.: Direct activation of cardiac pacemaker channels by intracellular cyclic AMP. Nature 351 (1991) 145-147.

Fain, G. L, Quandt, F. N., Bastian, B. L and Gerschenfeld, H. M.: Contribution of a caesium-sensitive conductance increase to the rod photoresponse. Nature 272 (1978) 467-469.

Finn, J. T., Grunwald, M. E. and Yau, K.-W.: Cyclic nucleotide-gated ion channels: An extended family with diverse functions. Annu. Rev. Physiol. 58 (1996) 395-426.

Garbers, D. L: Molecular basis of fertilization. Annu. Rev. Biochem. 58 (1989) 719-742.

Garbers, D. L.: Guanylyl cyclase receptors and their endocrine, paracrine, and autocrine ligands. Cell 71 (1992) 1-4.

Hagen, V., Dzeja, C., Frings, S., Bendig, J., Krause, E. and Kaupp, U. B.: Caged compounds of hydrolysis-resistant analogues of cAMP and cGMP: Synthesis and application to cyclic nucleotide-gated channels. Biochemistry 35 (1996) 7762-7771.

Halliwell, J. V. and Adams, P. R.: Voltage-clamp analysis of muscarinic excitation in hippocampal neurons. Brain Res. 250 (1982) 71-92.

Hansbrough, J. R., Kopf, G. S. and Garbers, D. L; The stimulation of sperm metabolism by a factor associated with eggs and by 8-bromo-guanosine 3',5'-monophosphate. Biochim. Biophys. Acta 630 (1980) 82-91.

Hille, B.: Ionic channels of excitable membranes. Sinauer Associates Inc., Sunderland, 1992.

Hodgkin, A. L. and Huxley, A. F.: A quantitative description of membrane current and its application to conduction and excitation in nerve. J. Physiol. 117 (1952) 500-544.

Ingram, S. L. and Williams, J. T: Modulation of the hyperpolarization-activated current (I) by cyclic nucleotides in guinea-pig primary afferent neurons. J. Physiol. 492 (1996) 97-106.

Ito, M. and Oshima, T.: Electrical behavior of the motoneurone membrane during intracellularly applied current steps. J. Physiol. 180 (1965) 607-635.

Kaupp, U. B., Niidome, T., Tanabe, T., Terada, S., Bonigk, W., Stuhmer, W., Cook, N. J., Kangawa, K., Matsuo, H., Hirose, T., Miyata, T. and Numa, S.: Primary structure and functional expression from complementary DNA of the rod photoreceptor cyclic GMP-gated channel. Nature 342 (1989) 762-766.

Labarca, P., Santi, C., Zapata, O., Morales, E., Beltran, C., Lievano, A. and Darszon, A.: A cAMP regulated K-selective channel from the sea urchin sperm plasma membrane. Develop. Biol. 174(1996)271-280.

Lee, H. C. and Garbers, D. L.: Modulation of the voltage-sensitive Na—/H— exchange in sea urchin spermatozoa through membrane potential changes induced by the egg peptide speract. J. Biol. Chem. 261 (1986) 16026-16032.

Llinas, R. R.: The intrinsic electrophysiological properties of mammalian neurons; insights into central nervous system function. Science 242 (1988) 1654-1664.

Ludwig, J., Margalit, T., Eismann, E., Lancet, D. and Kaupp, U. B.: Primary structure of cAMP-gated channel from bovine olfactory epithelium. FEBS Lett. 270 (1990) 24-29.

Pape, H.-C.: Queer current and pacemaker: The hyperpolarization-activated cation current in neurons. Annu. Rev. Physiol. 58 (1996) 299-327.

Pongs, O., Kecskemethy, N., Muller, R., Krah-Jentgens, I., Baumann, A., Kiltz, H. H., Canal, I., Llamazares, S. and Ferrus, A.: Shaker encodes a family of putative potassium channel proteins in the nervous system of *Drosophila*. EMBO J. 7 (1988) 1087-1096.

Sanger, F., Nicklen, S. and Coulson, A. R.: DNA sequencing with chain-terminating inhibitors. Proc. Natl. Acad. Sci. USA 74 (1977) 5463-5467.

Smith, P. L, Baukrowitz, T. and Yellen, G.: The inward rectification mechanism of the HERG cardiac potassium channel. Nature 379 (1996) 833-836.

Suarez, S. S., Varosi, S. M. and Dai, X.: Intracellular calcium increases with hyperactivation in intact, moving hamster sperm and oscillates with the flagellar beat cycle. Proc. Natl. Acad. Sci. USA 90 (1993) 4660-4664.

Takio, K., Wade, R. D., Smith, S. B., Krebs, E. G., Walsh, K. A. and Titani, K.: Guanosine cyclic 3',5'-phosphate dependent protein kinase, a chimeric protein homologous with two separate protein families. Biochemistry 23 (1984) 4207-4218.

Titani, K., Sasagawa, T., Ericsson, L H., Kumar, S., Smith, S. B., Krebs, E. G. and Walsh, K. A.: Amino acid sequence of the regulatory subunit of bovine type I adenosine cyclic 3',5'-phosphate dependent protein kinase. Biochemistry 23 (1984) 4193-4199.

Trudeau, M. C., Warmke, J. W., Ganetzky, B. and Robertson, G. A.: HERG, a human inward rectifier in the voltage-gated potassium channel family. Science 269 (1995) 92-95.

Vamum, M. D., Black, K. D. and Zagotta, W. N.: Molecular mechanism for ligand discrimination of cyclic nucleotide-gated channels. Neuron 15 (1995) 619-625.

Warmke, J., Drysdale, R. and Ganetzky, B.; A distinct potassium channel polypeptide encoded by the *Drosophila* eag locus. Science 252 (1991) 1560-1562.

Warmke, J. W. and Ganetzky, B.; A family of potassium channel genes related to eag in *Drosophila* and mammals. Proc. Natl. Acad. Sci. USA 91 (1994) 3438-3442.

Weiner, J.: Molekularbiologische, immunologische und funktionelle Charaktersierung von β-Untereinheiten des zyklisch Nukleotid-gesteuerten Ionenkanals aus dem Rinderhoden. Dissertation (1996) Universitat Dusseldorf Wollmuth, L. P. and Hille, B.: Ionic selectivity of $I_h$ channels of rod photoreceptors in tiger salamanders. J. Gen. Physiol. 100 (1992) 749-765.

Yanagihara, K. and Irisawa, H.; Inward current activated during hyperpolarization in the rabbit sino atrial node cell. Pflügers Arch. 385 (1980) 11-19.

The invention claimed is:

1. An isolated or purified polypeptide encoded by a nucleic acid comprising the nucleotide sequence of SEQ ID NO: 15.

\* \* \* \* \*